US009901738B2

(12) United States Patent
Mathur et al.

(10) Patent No.: US 9,901,738 B2
(45) Date of Patent: Feb. 27, 2018

(54) METHODS AND APPARATUSES FOR REMODELING TISSUE OF OR ADJACENT TO A BODY PASSAGE

(71) Applicant: Vessix Vascular, Inc., Laguna Hills, CA (US)

(72) Inventors: Prabodh Mathur, Laguna Niguel, CA (US); Shahram Moaddeb, Irvine, CA (US)

(73) Assignee: Vessix Vascular, Inc., Laguna Hills, CA (US)

( * ) Notice: Subject to any disclaimer, the term of this patent is extended or adjusted under 35 U.S.C. 154(b) by 0 days.

(21) Appl. No.: 14/984,808

(22) Filed: Dec. 30, 2015

(65) Prior Publication Data
US 2016/0106984 A1    Apr. 21, 2016

Related U.S. Application Data

(63) Continuation of application No. 13/760,846, filed on Feb. 6, 2013, now Pat. No. 9,402,684, which is a (Continued)

(51) Int. Cl.
*A61B 18/14*   (2006.01)
*A61B 18/00*   (2006.01)
(Continued)

(52) U.S. Cl.
CPC ...... *A61N 1/36117* (2013.01); *A61B 18/1492* (2013.01); *A61B 18/16* (2013.01);
(Continued)

(58) Field of Classification Search
CPC ........ A61N 1/36117; A61N 1/06; A61N 1/05; A61B 18/1492; A61B 2018/001
See application file for complete search history.

(56) References Cited

U.S. PATENT DOCUMENTS

| 5,379,765 A | 1/1995 | Kajiwara et al. |
| 5,407,465 A | 4/1995 | Schaub et al. |

(Continued)

FOREIGN PATENT DOCUMENTS

| CN | 1437494 A | 8/2003 |
| CN | 101203769 A | 6/2008 |

(Continued)

*Primary Examiner* — Catherine Voorhees

(57) ABSTRACT

Medical devices and methods for making and using the same are disclosed. An example method may include a method for treating a patient having congestive heart failure. The method may include positioning an expandable balloon in a renal artery of the patient. The expandable balloon may include a plurality of electrode assemblies. At least some of the electrode assemblies each may include at least two bipolar electrode pairs. The two bipolar electrode pairs may be longitudinally and circumferentially offset from one another. The method may also include expanding the balloon in the renal artery such that at least some of the bipolar electrode pairs are electrically coupled to a wall of the renal artery and energizing at least some of the bipolar electrode pairs so as to therapeutically alter at least one nerve proximate the renal artery to treat the patient's congestive heart failure.

20 Claims, 60 Drawing Sheets

Related U.S. Application Data continuation of application No. 13/725,872, filed on Dec. 21, 2012, now Pat. No. 9,174,050.

(60) Provisional application No. 61/580,141, filed on Dec. 23, 2011, provisional application No. 61/632,624, filed on Jan. 27, 2012, provisional application No. 61/633,154, filed on Feb. 6, 2012, provisional application No. 61/743,238, filed on Aug. 29, 2012, provisional application No. 61/743,225, filed on Aug. 29, 2012, provisional application No. 61/743,237, filed on Aug. 29, 2012.

(51) Int. Cl.
*A61N 1/06* (2006.01)
*A61N 1/05* (2006.01)
*A61N 1/36* (2006.01)
*A61B 18/16* (2006.01)
*A61B 18/18* (2006.01)
*A61N 5/00* (2006.01)
*A61B 18/12* (2006.01)

(52) U.S. Cl.
CPC ............... *A61B 18/18* (2013.01); *A61N 1/05* (2013.01); *A61N 1/06* (2013.01); *A61N 1/3606* (2013.01); *A61N 5/00* (2013.01); *A61B 2018/0016* (2013.01); *A61B 2018/0022* (2013.01); *A61B 2018/00404* (2013.01); *A61B 2018/00434* (2013.01); *A61B 2018/00511* (2013.01); *A61B 2018/00577* (2013.01); *A61B 2018/00654* (2013.01); *A61B 2018/00678* (2013.01); *A61B 2018/00767* (2013.01); *A61B 2018/00791* (2013.01); *A61B 2018/00815* (2013.01); *A61B 2018/124* (2013.01)

(56) References Cited

U.S. PATENT DOCUMENTS

| | | |
|---|---|---|
| 5,562,720 A | 10/1996 | Stern et al. |
| 6,470,217 B1 | 10/2002 | Fenn et al. |
| 6,780,182 B2 | 8/2004 | Bowman et al. |
| 6,787,870 B2 | 9/2004 | Wienand et al. |
| 7,698,962 B2 | 4/2010 | LeFebvre et al. |
| 8,226,294 B2 | 7/2012 | Bieberich et al. |
| 8,369,922 B2 | 2/2013 | Paul et al. |
| 8,454,596 B2 | 6/2013 | Ma et al. |
| 9,028,472 B2 | 5/2015 | Mathur et al. |
| 9,289,141 B2 | 3/2016 | Lowery et al. |
| 2007/0027514 A1 | 2/2007 | Gerber |
| 2007/0129720 A1* | 6/2007 | Demarais ............ A61N 1/36007 606/41 |
| 2007/0206655 A1 | 9/2007 | Haslett et al. |
| 2008/0188912 A1* | 8/2008 | Stone ................. A61B 18/1492 607/99 |
| 2012/0095461 A1* | 4/2012 | Herscher ............ A61B 18/1492 606/45 |
| 2014/0128859 A1* | 5/2014 | Lee ........................ A61L 29/14 606/33 |

FOREIGN PATENT DOCUMENTS

| | | |
|---|---|---|
| CN | 101600471 A | 12/2009 |
| JP | H05-168719 A | 7/1993 |
| JP | H06-38937 A | 2/1994 |
| JP | 2002301087 A | 10/2002 |
| WO | 2011139589 A2 | 11/2011 |

* cited by examiner

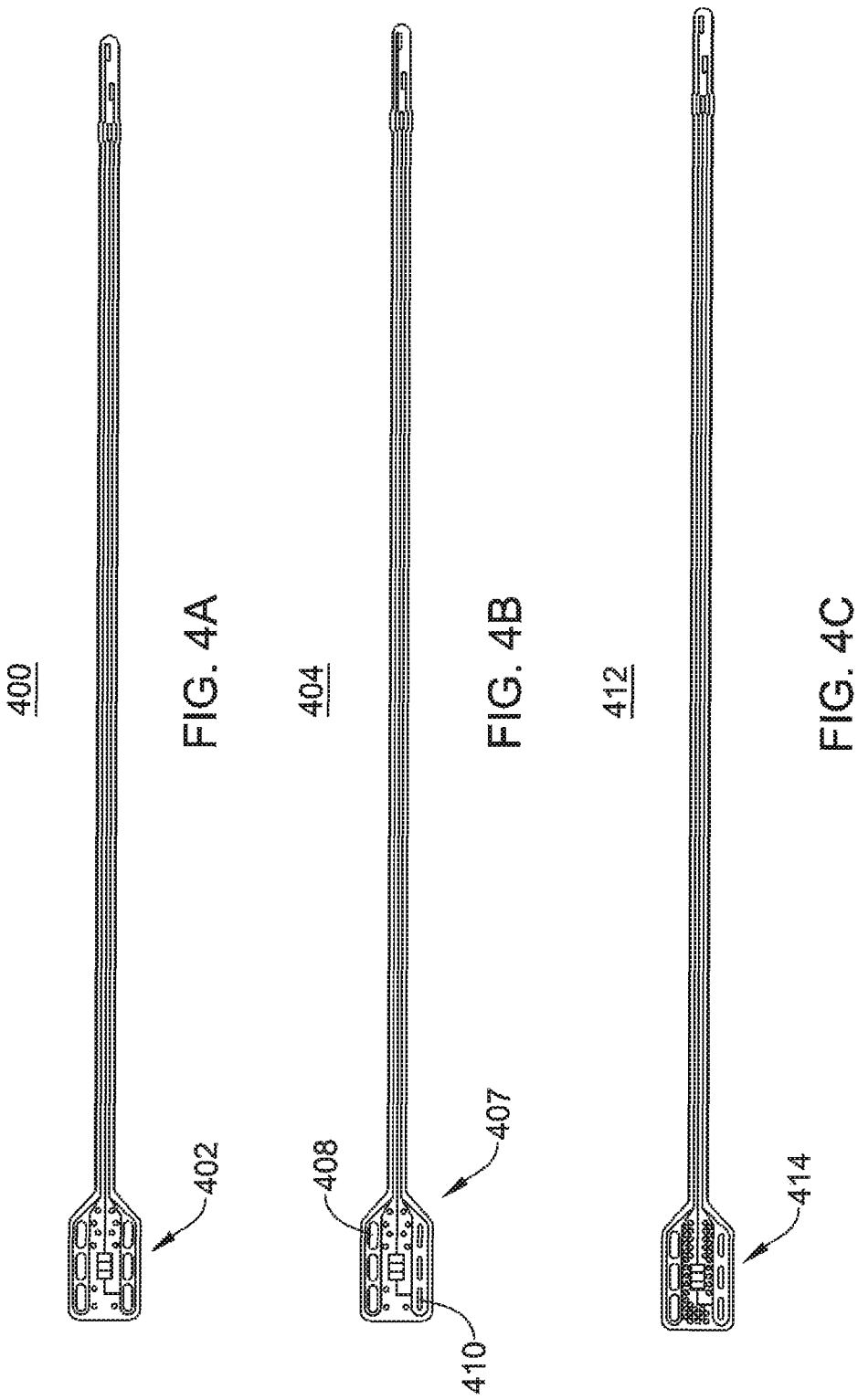

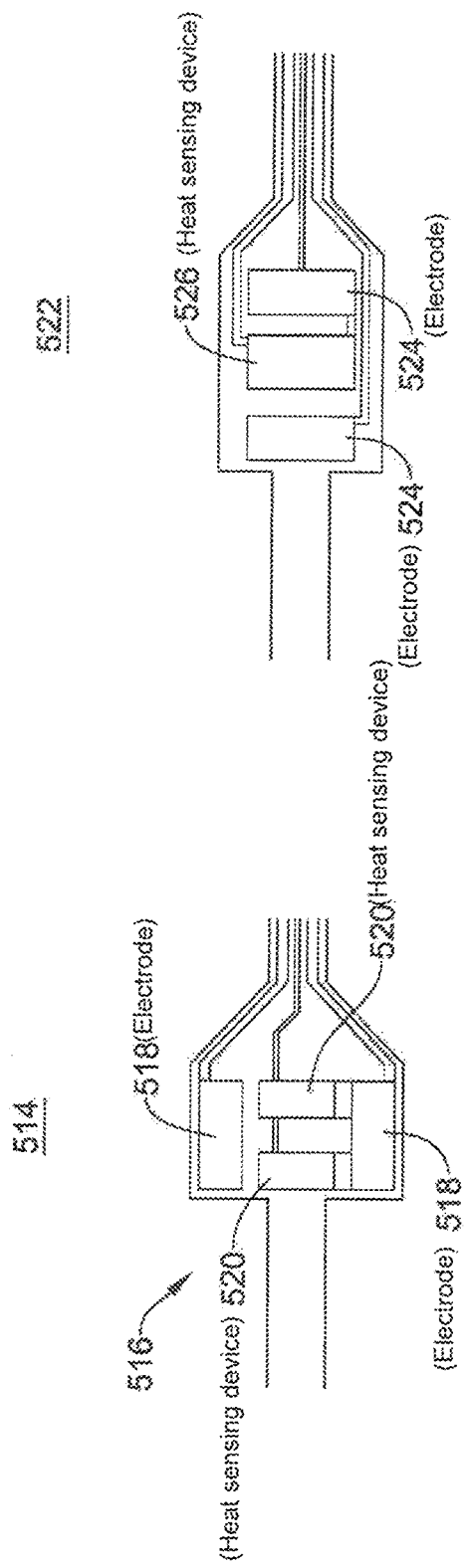

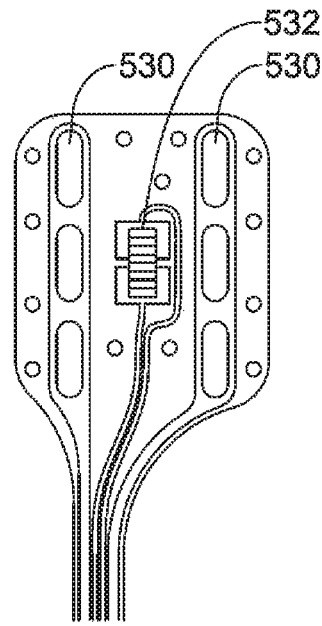 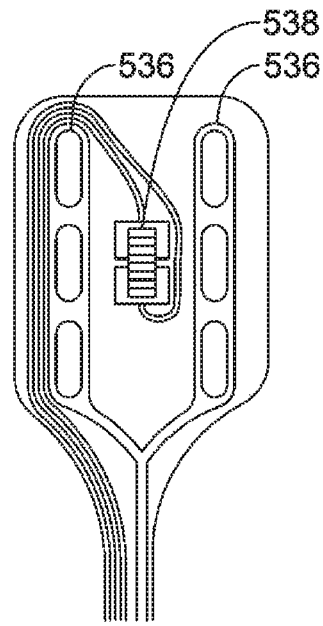
FIG. 5G    FIG. 5H
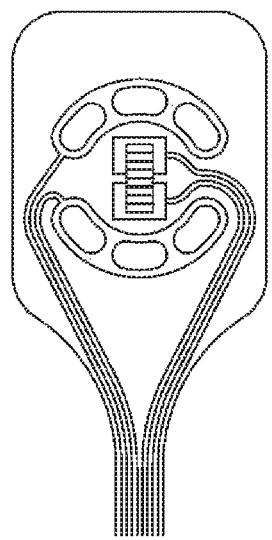
FIG. 5I

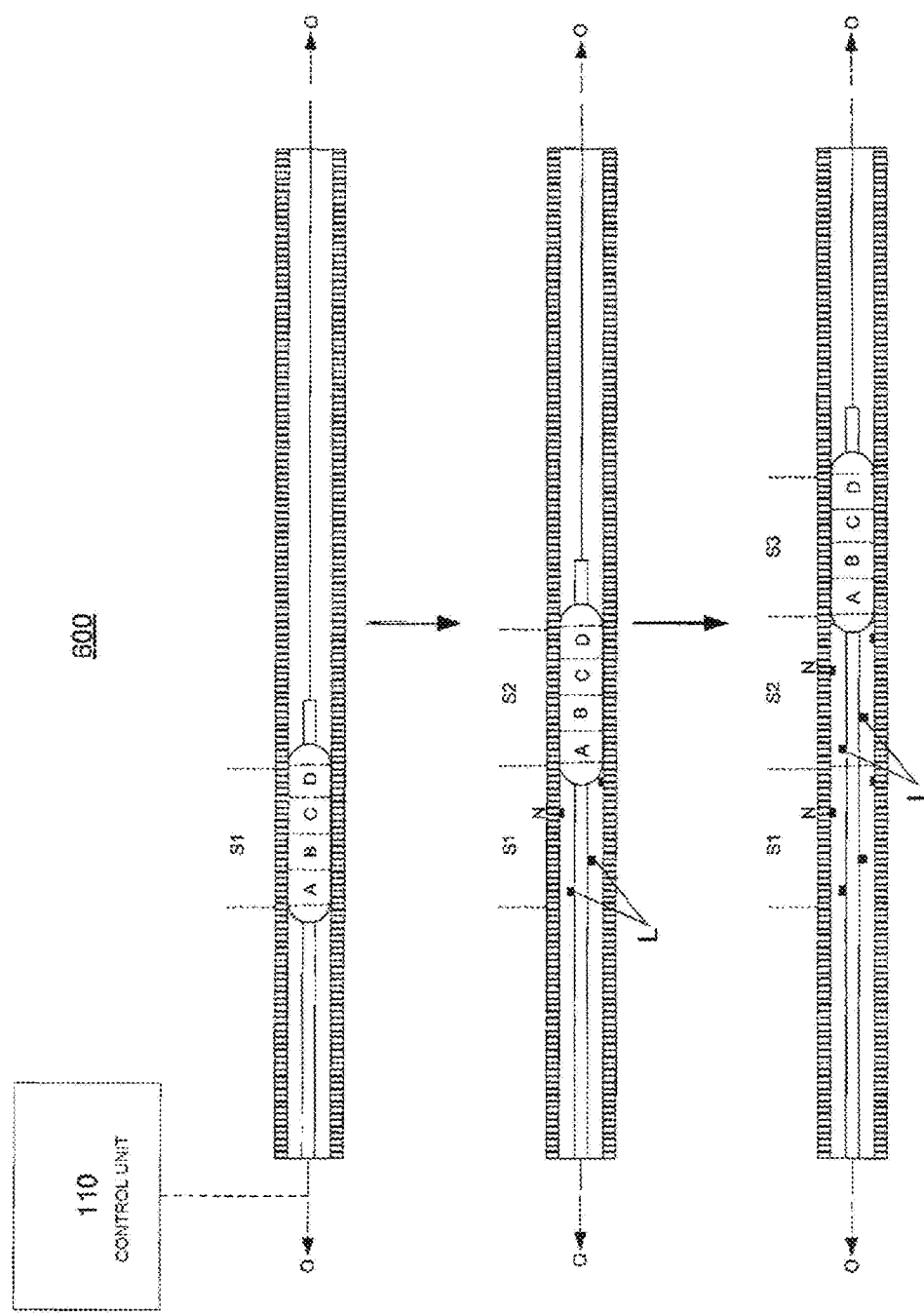

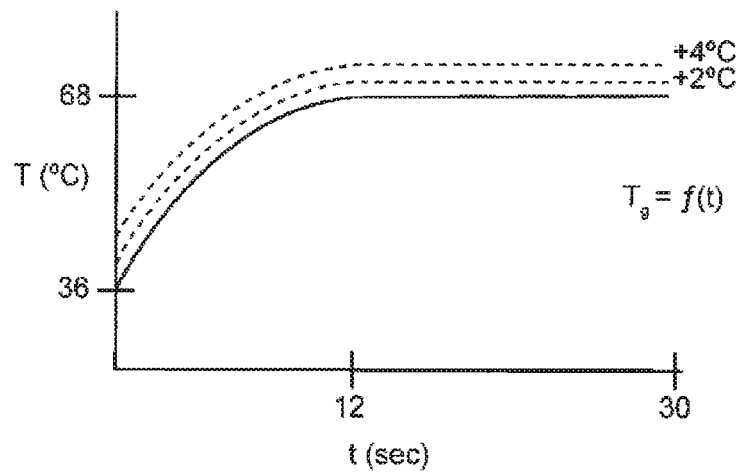
From t = 0 → 12 sec
T = a + bt + ct²
dT/dt = b + 2ct., Where b = 5 at t = 0
d²T/dt² = 2c
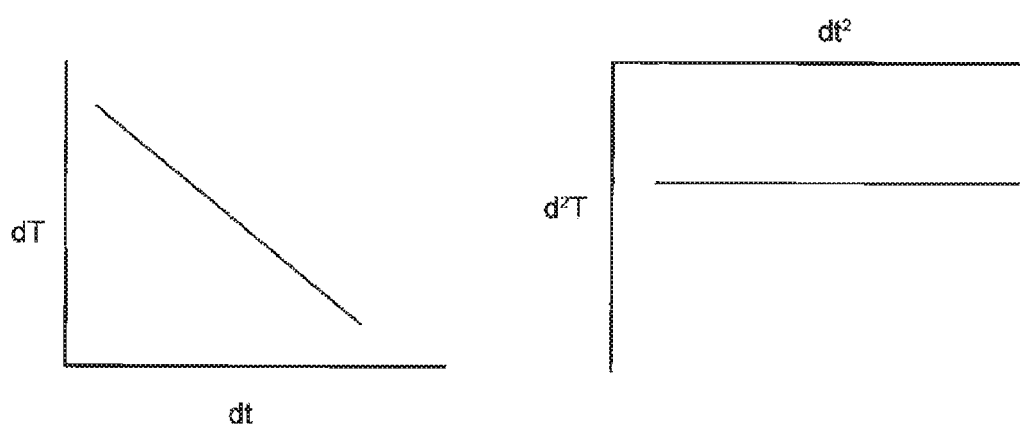
FIG. 7

| Impedance | | | 66C-20s-FAST | | 65C-30s-SLOW | | 65C-30s-MED | | 65C-30s-FAST | |
|---|---|---|---|---|---|---|---|---|---|---|
| | | | Average | Std. Dev. | Average | Std. Dev. | Average | Std. Dev. | Average | Std. Dev. |
| | At Start | ohms | 520 | 32 | 562 | 160 | 574 | 114 | 525 | 139 |
| | During Therapy | ohms | 321 | 36 | 375 | 171 | 381 | 106 | 325 | 75 |
| At Surface | Width | mm | 3.6 | 0.5 | 3.3 | 0.6 | 3.8 | 0.3 | 3.8 | 0.3 |
| | Length | mm | 4.1 | 0.3 | 4.4 | 0.5 | 4.4 | 0.6 | 4.3 | 0.5 |
| | Area | mm$^2$ | 15.0 | 2.6 | 14.4 | 4.2 | 16.4 | 2.6 | 16.0 | 2.8 |
| At 2.0 mm | Width | mm | 1.9 | 1.3 | 0.6 | 1.3 | 2.4 | 0.5 | 2.6 | 0.3 |
| | Length | mm | 2.4 | 1.6 | 0.6 | 1.3 | 2.8 | 0.6 | 3.4 | 0.3 |
| | Area | mm$^2$ | 6.0 | 4.4 | 1.6 | 3.1 | 6.7 | 2.7 | 8.9 | 1.2 |
| Penetration | Depth | mm | 2.6 | 0.9 | 1.9 | 0.9 | 2.9 | 0.6 | 2.8 | 0.6 |
| (Penetration) SQRT(Area at Surface) | | | 67% | 19% | 50% | 22% | 72% | 18% | 69% | 13% |
| (Area at 2 mm) (Area at Surface) | | | 39% | 26% | 12% | 23% | 43% | 22% | 56% | 10% |
| (Penetration × Width at 2 mm) (Area at Surface) | | | 37% | 25% | 14% | 28% | 45% | 22% | 45% | 7% |

FIG. 11

|  |  | 65C-30s-MED-EH | | 65C-30s-FAST | |
|---|---|---|---|---|---|
|  |  | Average | Std. Dev. | Average | Std. Dev. |
| Impedance | At Start | ohms | 612 | 82 | 610 | 106 |
|  | During Therapy | ohms | 359 | 53 | 389 | 94 |
| At Surface | Width | mm | 3.5 | 0.0 | 3.4 | 0.4 |
|  | Length | mm | 4.3 | 0.4 | 4.5 | 0.3 |
|  | Area | mm² | 15.1 | 1.6 | 15.4 | 2.5 |
| At 2.0 mm | Width | mm | 2.7 | 0.4 | 2.3 | 0.4 |
|  | Length | mm | 3.2 | 0.3 | 2.9 | 0.6 |
|  | Area | mm² | 8.5 | 1.4 | 7.0 | 2.4 |
| Penetration | Depth | mm | 3.1 | 0.5 | 3.3 | 0.7 |
|  | (Penetration) / SQRT(Area at Surface) |  | 80% | 16% | 83% | 20% |
|  | (Area at 2 mm) / (Area at Surface) |  | 57% | 13% | 46% | 19% |
|  | (Penetration x Width at 2 mm) / (Area at Surface) |  | 56% | 11% | 52% | 23% |

FIG. 12

TGU007 Study Design

| Group | Number of Animals | Recovery Interval (Days) | Left or Right Renal Treatment | Contralateral Renal Treatment |
|---|---|---|---|---|
| 1 | 5 | 7 | 68° C for 30 seconds | None |
| 2[a] | 5 | 7 | 68° C for 30 seconds | None |
| 3 | 6 | 28 | 68° C for 30 seconds | 68° C for 30 seconds |
| 4[b] | 6 | 28 | 68° C for 30 seconds | 68° C for 30 seconds | a – 1.5 or 2 treatments may be applied with minimal or no overlapping to the selected renal artery if sufficient length allows. Half a treatment is defined as half of the balloon is in the aorta and only the electrode pairs which are apposed to the renal artery are activated.

b – Two or one and a half treatments may be applied to the longer of the two renal arteries if sufficient length allows with minimal overlapping.

FIG. 25

Representative angiography images of a renal artery pre-treatment and 7 days following treatment of 60°C for 30 seconds (one treatment per artery).

Representative angiography images of a renal artery pre-treatment and 7 days following treatment of 68°C for 30 seconds (two treatments along the length of the artery).

Representative angiography images of a renal artery pre-treatment and 28 days following bilateral treatment of 085°C for 30 seconds (one treatment per artery).

Representative angiography images of a renal artery pre-treatment and 28 days following bilateral treatment of 68°C for 30 seconds (2 treatments along the length of the artery).

Thermo-sensitive GEL

Yellow color continuing growing until treatment stops at 30 Sec

Yellow color size grows indicative of heat conduction within GEL.

V2 Catheter with RF Treatment initiated. Yellow Color changes indicates localized electrode heating 4 mm balloon with three electrode assemblies 5 mm balloon with three electrode assemblies

METHODS AND APPARATUSES FOR REMODELING TISSUE OF OR ADJACENT TO A BODY PASSAGE

CROSS-REFERENCE TO RELATED APPLICATIONS

This application is a continuation of U.S. patent application Ser. No. 13/760,846 (granted as U.S. Pat No. 9,402,684) filed Feb. 6, 2013, which is a continuation of U.S. patent application Ser. No. 13/725,872 (granted as U.S. Pat. No. 9,174,050) filed Dec. 21, 2012, which claims priority under 35 U.S.C. § 119 to U.S. Provisional Application Ser. No. 61/580,141 filed Dec. 23, 2011, U.S. Provisional Application Ser. No. 61/632,624 filed Jan. 27, 2012, U.S. Provisional Application Ser. No. 61/633,154 filed Feb. 6, 2012, U.S. Provisional Application Ser. No. 61/743,238 filed Aug. 29, 2012, U.S. Provisional Application Ser. No. 61/743,225 filed Aug. 29, 2012, and U.S. Provisional Application Ser. No. 61/743,237 filed Aug. 29, 2012, the entire disclosures of which are herein incorporated by reference.

This application is related to U.S. patent application Ser. No. 13/750,879 (granted as U.S. Pat No. 9,186,211), filed Jan. 25, 2013; U.S. patent application Ser. No. 13/725,843 (granted as U.S. Pat No. 9,037,259), filed Dec. 21, 2012; U.S. patent application Ser. No. 13/725,885(published as U.S. Publication No. US20130165924A1), filed Dec. 21, 2012; U.S. patent application Ser. No. 13/725,894 (granted as U.S. Pat. No. 9,028,472), filed Dec. 21, 2012; and U.S. patent application Ser. No. 13/725,904 (granted as U.S. Pat. No. 9,072,902), filed Dec. 21, 2012; the entire disclosures of which are herein incorporated by reference.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example method may include a method for treating a patient having high blood pressure. The method may include providing a device. The device may include a catheter extending along a longitudinal axis. A balloon having an unexpanded state and an expanded state may be coupled to an end of the catheter. The balloon may have a plurality of cylindrical treatment zones extending along the longitudinal axis in the expanded state. A plurality of electrode pad assemblies may be mounted to the balloon. Each electrode pad assembly may include a substrate supporting first and second electrode pads with each electrode pad having a pair of elongate bipolar electrodes. The electrode pads of each electrode pad assembly may be longitudinally and circumferentially offset from one another. The method may also include expanding the balloon in the renal artery so as to electrically couple the electrodes with a wall of the renal artery and driving bipolar energy between the electrodes of each bipolar pair so as to therapeutically alter nerves surrounding the renal artery such that the high blood pressure of the patient is mitigated.

Each electrode pad may include a temperature sensor disposed between the electrodes of the pair. The expanding of the balloon thermally may couple the temperature sensors with the wall of the renal artery. In some embodiments, the method may further include directing the energy to the bipolar pairs in response to a temperature signal from the temperature sensor so as to heat the wall approximately evenly.

The electrode pad assemblies may be arranged on the balloon so that at least some of the electrode pads are longitudinally separated from a circumferentially adjacent electrode pad. In some embodiments, the method may further include advancing the balloon into the renal artery by flexing the balloon between the longitudinally separated electrode pads.

Another example method may include a method for treating a body passageway. The method may include providing a device. The device may include a catheter extending along a longitudinal axis. A balloon having an unexpanded state and an expanded state may be coupled to an end of the catheter. The balloon may have a plurality of cylindrical treatment zones extending along the longitudinal axis in the expanded state. A plurality of electrode assemblies may be coupled to the balloon. Each electrode assembly may include a distal electrode pad and a proximal electrode pad. The distal electrode pad may be longitudinally separated from the proximal electrode pad by an intermediate tail. Each electrode pad may include a bipolar electrode pair. The distal electrode pad and proximal electrode pad may be circumferentially offset from one another in the expanded state of the balloon. The plurality of electrode pads may be each longitudinally arranged such that each cylindrical treatment zone includes at least one of the distal and proximal electrode pads of at least one of the plurality of electrode pad assemblies. The intermediate tail of each electrode assembly may extend in the longitudinal direction such that the distal electrode pad and proximal electrode pad of any particular electrode pad assembly occupy non-adjacent treatment zones on the balloon. The method may also include expanding the balloon in a section of a body passageway. The section may be elongated along an axis. The method may also include activating the electrode pads while the balloon is expanded to deliver energy to the section of body passageway, such that the section of body passageway receives a plurality of non-contiguous treatments along the longitudinal axis.

Activating the electrode pads may create at least one lesion on the section of body passageway for each treatment zone of the balloon. The lesions may not contact one another. For example, the at least one lesion of each treatment zone may not axially overlap the at least one lesion of an adjacent treatment zone.

The method may include monitoring temperature at each of the electrode assemblies. Monitoring temperature may include using at least one of the electrode assemblies to monitor temperature of one of its bipolar electrode pairs using a heat sensing device and/or monitoring temperature may include using at least one of the electrode assemblies to monitor temperature of one of its bipolar electrode pairs using a heat sensing device of the other bipolar electrode pair.

Each bipolar electrode pair may include a plurality of ground electrodes and a plurality of active electrodes. Each plurality of ground and active electrodes may be elongated along the axis and/or each plurality of ground and active electrodes may be elongated transverse to the axis.

The balloon may have four cylindrical treatment zones. Two electrode assemblies may be coupled to the balloon such that each zone includes one distal electrode pad or one proximal electrode pad. In some embodiments, three electrode assemblies may be coupled to the balloon such that each of two non-adjacent cylindrical treatment zones includes two distal electrode pads or two proximal electrode pads and each of the other two non-adjacent cylindrical treatment zones includes one distal electrode pad or one proximal electrode pad. In some embodiments, one particular cylindrical treatment zone may include one proximal electrode pad of one electrode assembly and two intermediate tails of the two other electrode assemblies. In some embodiments, one particular cylindrical treatment zone may include two distal electrode pads of two different electrode assemblies and one intermediate tail of the remaining electrode assembly.

The balloon may have four cylindrical treatment zones, and four electrode assemblies may be coupled to the balloon such that each of two non-adjacent cylindrical treatment zones includes two distal electrode pads or two proximal electrode pads and each of the other two non-adjacent cylindrical treatment zones includes one distal electrode pad or one proximal electrode pad. Two distal electrode pads of two different electrode assemblies may occupy a particular cylindrical treatment zone, with each of these two distal electrode pads being circumferentially separated by an intermediate tail of one of the other two other electrode assemblies. Two proximal electrode pads of two different electrode assemblies may occupy a particular cylindrical treatment zone, with each of these two proximal electrode pads being circumferentially separated by an intermediate tail of one of the other two other electrode assemblies.

An example device may include a catheter extending along a longitudinal axis. A balloon may be coupled to an end of the catheter. A plurality of electrode assemblies may be mounted to the balloon. Each electrode assembly may comprise first and second longitudinally separated electrode pads. The electrode pads of each electrode assembly may be circumferentially offset from one another in the expanded state of the balloon. The plurality of electrode assemblies may be longitudinally arranged such that one of the electrode pads of one of the plurality of electrode assemblies is disposed longitudinally between the electrode pads of another of the electrode assemblies.

Another example device may include a catheter extending along a longitudinal axis. A balloon may be coupled to an end of the catheter. The balloon may have a plurality of cylindrical treatment zones extending along the longitudinal axis in an expanded state. A plurality of electrode assemblies may be to the balloon. Each electrode assembly may include a distal electrode pad and a proximal electrode pad. The distal electrode pad may be longitudinally separated from the proximal electrode pad by an intermediate tail. Each electrode assembly may include a bipolar electrode pair. The distal electrode pad and proximal electrode pad may be circumferentially offset from one another in the expanded state of the balloon. The plurality of electrode pads may be each longitudinally arranged such that each cylindrical treatment zone includes at least one of the distal and proximal electrode pads of at least one of the plurality of electrode assemblies. The intermediate tail of each electrode assembly may extend in the longitudinal direction such that the distal electrode pad and proximal electrode pad of any particular electrode assembly occupy non-adjacent treatment zones on the balloon.

The balloon may have four cylindrical treatment zones, and two electrode assemblies may be coupled to the balloon such that each zone includes one distal electrode pad or one proximal electrode pad.

The balloon has four cylindrical treatment zones, and three electrode assemblies may be coupled to the balloon such that each of two non-adjacent cylindrical treatment zones includes two distal electrode pads or two proximal electrode pads and each of the other two non-adjacent cylindrical treatment zones includes one distal electrode pad or one proximal electrode pad.

One particular cylindrical treatment zone may include one proximal electrode pad of one electrode assembly and two intermediate tails of the two other electrode assemblies.

One particular cylindrical treatment zone may include two distal electrode pads of two different electrode assemblies and one intermediate tail of the remaining electrode assembly.

The balloon may have four cylindrical treatment zones, and four electrode assemblies may be coupled to the balloon such that each of two non-adjacent cylindrical treatment zones includes two distal electrode pads or two proximal electrode pads and each of the other two non-adjacent cylindrical treatment zones includes one distal electrode pad or one proximal electrode pad.

Two distal electrode pads of two different electrode assemblies may occupy a particular cylindrical treatment zone, with each of these two proximal electrode pads being circumferentially separated by an intermediate tail of one of the other two other electrode assemblies.

Two proximal electrode pads of two different electrode assemblies may occupy a particular cylindrical treatment zone, with each of these two proximal electrode pads being circumferentially separated by an intermediate tail of one of the other two other electrode assemblies.

Each electrode pad may include a ground electrode and an active electrode.

Each electrode pad may include a heat sensing device.

Each electrode assembly may further comprises a proximal tail extending from the proximal electrode pad.

For each electrode assembly, the intermediate tail comprises an intermediate ground line, intermediate active electrode line, and intermediate heat sensor line, and the proximal tail comprises the intermediate active electrode line, intermediate heat sensor line, a proximal ground line, proximal active electrode line, and proximal heat sensing line.

The width of the proximal tail may be approximately 150% of the width of the intermediate tail.

The intermediate ground line may be extended on an axis shared with the proximal ground line.

A distal ground electrode of the distal electrode pad and a proximal ground electrode of the proximal electrode pad may both extend along the axis shared with the intermediate and proximal ground lines, such that the distal ground electrode, intermediate ground line, proximal ground electrode, and proximal ground line all extend along on the axis.

Another example device may include an expandable balloon including an outer surface and a plurality of discrete flexible circuits extending along the outer surface of the expandable balloon. At least some of the flexible circuits each may include two or more energy treatment sites. At least some portions of some of the flexible circuits may be shaped to at least approximately key to a shape of at least one adjacent flexible circuit.

At least some of the flexible circuits may each include a distal electrode pad, a proximal electrode pad, an intermediate tail extending between the distal and proximal electrode pads, and a proximal tail extending proximally away from the proximal electrode pad.

At least some of the distal electrode pads may be positioned proximate adjacent intermediate tails and wherein at least some of the proximal electrode pads may be positioned proximate adjacent intermediate tails.

At least some portions of some of the flexible circuits may be shaped to not key to a shape of at least one adjacent flexible circuit.

The energy treatment sites of at least some of the flexible circuits may be longitudinally and circumferentially offset relative to one another.

The energy treatment sites may each comprise a pair of adjacent bipolar electrodes.

The energy treatment sites may each further comprise a temperature sensor positioned between the pair of adjacent bipolar electrodes.

Another example device may include an elongated catheter, an expandable balloon associated with the catheter, and a plurality of circumferentially spaced flexible circuits extending longitudinally along a surface of the expandable balloon. Each flexible circuit may include at least one electrode. The electrodes may be spaced apart axially and circumferentially relative to each other. The flexible circuits may be adhesively secured to the expandable balloon and include a plurality of openings extending through the flexible circuits. The openings may be configured to increase flexibility of the flexible circuits.

The electrodes may be monopolar electrodes.

Each flexible circuit may include a first monopolar electrode and a second monopolar electrode. The first and second monopolar electrodes may be circumferentially offset. The monopolar electrodes of a first flexible circuit may be longitudinally offset relative to the monopolar electrodes of adjacent flexible circuits.

The device may further comprises a common electrode. The common electrode may be positioned on the surface of the expandable balloon.

At least some corners of the flexible circuits may be rounded corners.

Each flexible circuit may include at least one conductor trace extending longitudinally along the flexible circuit.

Each flexible circuit may include at least two discrete conductor traces extending longitudinally along the flexible circuit.

Another example device may include an expandable balloon including an outer surface. A plurality of discrete flexible circuits may extend along the outer surface of the expandable balloon. At least some of the flexible circuits may each include two or more monopolar electrodes. At least some portions of some of the flexible circuits may be shaped to at least approximately key to a shape of at least one adjacent flexible circuit.

The flexible circuits may be adhesively bonded to the outer surface of the balloon.

The flexible circuits may include openings configured to increase the flexibility of the circuits.

Another example device may include an expandable balloon including an outer surface. At least one flexible circuit may be mounted on the outer surface of the expandable balloon. The at least one flexible circuit may include a first insulating layer. At least one heat sensing device may be positioned at least partially within the first insulating layer. A conductive layer may be disposed above the first insulating layer, at least a portion of which may be electrically coupled to the heat sensing device. A second insulating layer may be disposed above the conductive layer. At least one monopolar electrode may be associated with the conductive layer.

The at least one electrode may be positioned above the second insulating layer and may be coupled to the conductive layer through the second insulating layer.

The heat sensing device may have a thickness of less than approximately 0.15 mm.

The at least one monopolar electrode may include at least two monopolar electrode pads, and wherein the heat sensing device may be positioned between the pair of monopolar electrode pads.

The heat sensing device may be positioned relative to the monopolar electrode such that the heat sensing device is configured to measure a temperature representative of both the monopolar electrode and a tissue when the device is in contact with the tissue.

The heat sensing device may or may not be electrically coupled to the monopolar electrode.

The device may be configured to be fully inflated at an inflation pressure of 10 atmospheres or less or at an inflation pressure of 6 atmospheres or less.

Another example device may include an expandable, non-compliant balloon including an outer surface. The expandable balloon may be configured to be fully inflated at an inflation pressure of 10 atmospheres or less. A plurality of thin film flexible circuits may extend longitudinally along an outer surface of the balloon. At least one of the flexible circuits may include a first insulating layer facing the outer surface of the balloon, at least one heat sensing device, a conductive layer above the first insulating layer, a second insulating layer above the conductive layer, and at least one electrode associated with the conductive layer. The maximum thickness of the flexible circuit may be less than 0.2 mm.

The maximum thickness of the flexible circuit may be equal to the sum of thicknesses of the first insulating layer, the heat sensing device, the conductive layer, the second insulating layer, and the electrode.

The at least one electrode may be a monopolar electrode.

The heat sensing device may be positioned at least partially within the first insulating layer.

The thickness of the heat sensing device may be less than 0.15 mm.

The balloon may be configured to be fully inflated at an inflation pressure of 6 atmospheres or less.

An example electrode pad may include a base insulating layer having a base opening. A heat sensing component may be positioned within the base opening and may have a first pole and a second pole. A conductive layer may be on top of the base insulating layer. The conductive layer may include a first trace connected to the first pole, a second trace connected to the second pole, and a third trace. A top insulating layer may be layered on top of the conductive layer. The top insulating layer may have a first plurality of openings over the first trace and a second plurality of openings over the second trace. A first plurality of electrodes may be layered on top of the top insulating layer and may be conductively coupled to the first trace via the first plurality of openings in the top insulating layer. A second plurality of electrodes may be layered on top of top insulating layer and may be conductively coupled to the second trace via the second plurality of openings.

The base insulating layer may have a rectangular shape extending in lateral and longitudinal directions. The rectangular shape may transition to a narrow extension extending in the longitudinal direction.

The first trace may comprise a first elongate electrode trace extending in the longitudinal direction.

The first trace may further comprise a first ground pad laterally displaced from the first elongate trace. The ground pad may be electronically coupled to the heat sensing component.

The third trace may comprise a power pad coupled to the heat sensing component.

Distal portions of each of the first elongate electrode trace and ground pad may be connected by a bridge portion.

Each of first plurality of electrodes may be elongated in the longitudinal direction.

The second trace may comprise a second elongate electrode trace extending in the longitudinal direction.

The second elongate electrode trace may be substantially parallel to the first elongate electrode trace.

The base insulating layer and top insulating layer may each comprise a flexible polymer. The flexible polymer may comprise polyimide. The polyimide may be approximately 0.0013 mm thick.

The top insulating layer may be discretely shaped with respect to an upper surface of the conductive layer.

The top insulating layer may substantially match the bottom insulating layer in shape.

The heat sensing component may comprise a thermistor. The thermistor may be approximately 0.10 mm thick.

The surface area of the first plurality of electrodes may be substantially equal to the surface area of the second plurality of electrodes.

The first and second plurality of electrodes may comprise gold.

An example electrode assembly may include a base insulating layer comprising a distal electrode pad, an intermediate tail, a proximate electrode pad. The base insulating layer may have a thermistor opening. The base layer may be rectangular and extending in longitudinal and lateral directions. A thermistor may be positioned within the thermistor opening and may have a ground pole and a power pole. A conductive layer may be layered on top of the base insulating layer. The conductive layer may include a ground trace connected to the first pole, a second trace connected to the second pole, and a third trace. A top insulating layer may be layered on top of the conductive layer. The top insulating layer may have a first plurality of openings over the first trace and a second plurality of openings over the second trace. A first plurality of electrodes may be layered on top of the top insulating layer and may be conductively coupled to the first trace via the first plurality of openings in the top insulating layer. A second plurality of electrodes may be layered on top of the top insulating layer and may be conductively coupled to the second trace via the second plurality of openings.

An example flexible circuit assembly may include a distal electrode pad. The distal electrode pad may include a distal base insulating layer having a distal thermistor opening, a distal thermistor being positioned within the distal thermistor opening and having a first distal pole and a second distal pole, a distal conductive layer layered on top of the distal base insulating layer, the distal conductive layer comprising a distal ground trace linearly extending along a ground axis and coupled to the first distal sensor pole, a distal sensor trace coupled to the second distal pole, and a distal active electrode trace, a distal top insulating layer layered on top of the distal conductive layer, the distal top insulating layer having a first distal plurality of openings over the first distal trace and a second distal plurality of openings over the second distal trace, a first distal plurality of electrodes extending along the ground axis and layered on top of the distal top insulating layer and being conductively coupled to the distal ground trace via the first distal plurality of openings in the distal top insulating layer, and a second distal plurality of electrodes layered on top of the distal top insulating layer, and laterally displaced from the first distal plurality of electrodes on a first lateral side of the ground axis, and being conductively coupled to the distal active electrode trace via the second distal plurality of openings. An intermediate tail may proximally extend from the distal electrode pad. The intermediate tail may include an intermediate base insulating layer extending from the distal base insulating layer and an intermediate conductive layer layered on top of the intermediate insulating layer. The intermediate conductive layer may include an intermediate ground line extending from the distal ground trace along the ground axis, an intermediate active electrode line coupled to the distal active electrode trace and extending along a first outer axis parallel to the ground axis on the first lateral side of the ground axis, and an intermediate sensor line coupled to the distal sensor trace and extending along a first inner axis parallel to the ground axis on the first lateral side of the ground axis and between the ground axis and first outer axis. An intermediate top insulating layer may be layered on top of the intermediate conductive layer. A proximal electrode pad may be coupled to the intermediate extension member. The proximal electrode pad may include a proximal base insulating layer having a proximal thermistor opening, a proximal thermistor being positioned within the proximal thermistor opening and having a first proximal pole and a second proximal pole, and a proximal conductive layer layered on top of the distal base insulating layer. The proximal conductive layer may include a proximal ground trace linearly extending along the ground axis and coupled to the first proximal sensor pole, a distal sensor trace coupled to the second distal pole, and a proximal active electrode trace. A proximal top insulating layer may be layered on top of the proximal conductive layer. The proximal top insulating layer may have a first proximal plurality of openings over the first proximal distal trace and a second proximal plurality of openings over the second proximal trace. A proximal distal plurality of electrodes may extend along the ground axis and layered on top of the proximal top insulating layer and being conductively coupled to the proximal ground trace via the first proximal plurality of openings in the proximal top insulating layer. A second proximal plurality of electrodes may be layered on top of the proximal top insulating layer, and laterally displaced from the first proximal plurality of electrodes on a second lateral side of the ground axis, and being conductively coupled to the proximal active electrode trace via the second proximal plurality of openings. A proximal tail may proximally extend from the proximal electrode pad. The proximal tail may include a proximal insulating layer extending from the proximal base insulating layer and a proximal conductive layer layered on top of the proximal insulating layer. The proximal conductive layer may include a proximal ground line extending from the proximal ground trace along the ground axis, a proximal active electrode line coupled to the distal active electrode trace and extending along a second outer axis parallel to the ground axis on the second lateral side of the ground axis, a proximal sensor line coupled to the proximal sensor trace and extending along a second inner axis parallel to the ground axis on the second lateral side of the ground axis and between the ground axis and second outer axis, an intermediate active electrode line, and an intermediate sensor line. A proximal top insulating layer may be layered on top of the proximal conductive layer.

Another example device may include an expandable balloon including an outer surface and at least one flexible circuit mounted on the outer surface of the expandable balloon. The at least one flexible circuit may include a first insulating layer, at least one heat sensing device positioned at least partially within the first insulating layer, a conductive layer above the first insulating layer, at least a portion of which is electrically coupled to the heat sensing device, a second insulating layer above the conductive layer, and at least one electrode associated with the conductive layer.

The at least one electrode may be positioned above the second insulating layer and may be coupled to the conductive layer through the second insulating layer.

The heat sensing device may have a thickness of less than approximately 0.15 mm. For example, the heat sensing device may have a thickness of approximately 0.1 mm.

The at least one electrode may be a pair of bipolar electrodes.

The heat sensing device may be positioned between the pair of bipolar electrodes.

The heat sensing device may be positioned relative to the pair of bipolar electrodes such that the heat sensing device is configured to measure a temperature representative of both the bipolar electrodes and a tissue when the device is in contact with the tissue.

The heat sensing device may be electrically coupled to one of the pair of bipolar electrodes.

The pair of bipolar electrodes may include a plurality of active electrodes and a plurality of ground electrodes.

The plurality of active electrodes may be arranged along a first longitudinal axis and the plurality of ground electrodes are arranged along a second longitudinal axis that is offset from and approximately parallel to the first longitudinal axis.

The heat sensing device may be positioned relative to the at least one electrode such that the heat sensing device may be configured to measure a temperature representative of both the at least one electrode and a tissue when the device is in contact with the tissue.

Another example method may include a method for treating a patient having high blood pressure. The method may include providing a device. The device may include a catheter, an expandable balloon coupled to the catheter and including an outer surface, and at least one flexible circuit mounted on the outer surface of the expandable balloon. The at least one flexible circuit may include a first insulating layer, at least one heat sensing device positioned at least partially within the first insulating layer, a conductive layer above the first insulating layer, at least a portion of which is electrically coupled to the heat sensing device, a second insulating layer above the conductive layer, and at least one electrode associated with the conductive layer. The method may also include expanding the balloon in a renal artery of the patient and driving energy through the at least one electrode so as to therapeutically alter at least one nerve proximate the renal artery such that the high blood pressure of the patient is mitigated.

Providing the device may include providing the device with at least a pair of bipolar electrodes and the heat sensing device positioned between the pair of bipolar electrodes.

The method may also include using the heat sensing device to measure a temperature representative of both the at least one electrode and of a wall of the renal artery.

Another example device may include a catheter, an expandable balloon coupled to the catheter and including an outer surface, and at least one flexible circuit mounted on the outer surface of the expandable balloon. The at least one flexible circuit may include a first insulating layer, at least one heat sensing device positioned at least partially within the first insulating layer, a conductive layer above the first insulating layer, at least a portion of which is electrically coupled to the heat sensing device, a second insulating layer above the conductive layer, and at least one electrode associated with the conductive layer.

An example catheter may include an elongate flexible catheter body. An expandable structure may be associated with the catheter body and may include a radially expandable balloon and a plurality of flexible circuits extending along an outer surface of the balloon, each flexible circuit including at least one electrode and at least one temperature sensor. The expandable structure may have an outer diameter of less than 4 mm when in an expanded configuration.

The outer diameter of the expandable structure may be between approximately 1 mm and 3 mm.

The balloon may be non-cannulated.

At least a portion of the outer surface of the balloon may be a flexible polyimide film. The flexible polyimide film may define a base insulative layer of the plurality of flexible circuits.

An upper surface of the base insulative layer of the balloon may directly contact a conductive layer of at least one of the flexible circuits.

Each flexible circuit may include a base insulative layer adjacent the outer surface of the balloon.

An example system for renal denervation of a patient having a primary renal artery extending between an aorta and a kidney and an accessory renal artery extending between the aorta and the kidney may include a first balloon catheter and a second balloon catheter, each having a balloon with a small profile configuration and a large profile configuration, with a plurality of flexible circuits extending along an outer surface of each balloon, each flexible circuit including at least one electrode. At least one of the balloons may have a large profile configuration that is less than 4 mm in outer diameter. A power source may be electrically coupled to the electrodes of the first and second balloon catheters and may be configured to energize the electrodes with a renal denervation energy.

One of the balloons may have a large profile configuration that is equal to or greater than 4 mm in outer diameter.

The first and second balloons may have large profile configurations that are different outer diameter sizes.

The system may be used for renal denervation of a patient further having a second renal artery extending between the aorta and a second kidney. The system may further comprising a third balloon catheter having a small profile configuration and a large profile configuration, with a plurality of flexible circuits extending along an outer surface of the third balloon, each flexible circuit including at least one electrode; and wherein the electrodes of the third balloon catheter are electrically coupled to the power source.

The first, second and third balloons, when in the large profile configurations, may define different outer diameters from one another. The outer diameter of the third balloon when in the large profile configuration may be greater than or equal to 4 mm.

An example renal denervation method may include positioning a radially expandable structure of an elongate flexible catheter body at a location in an accessory renal artery connecting an aorta to a kidney, the aorta and the kidney further connected by a primary renal artery, the radially expandable structure comprising a plurality of electrodes, expanding the radially expandable structure such that at least a subset of the electrodes engage a wall of the accessory renal artery, and using a power source electrically coupled to the electrodes, energizing at least a subset of the plurality of electrodes to deliver energy to tissue proximate the accessory renal artery.

The method may also include positioning the radially expandable structure at a location in the primary renal artery, expanding the radially structure such that at least some of the electrodes engage a wall of the primary renal artery, and energizing at least some of the electrodes to deliver energy to tissue proximate the primary renal artery.

The method may also include positioning a second radially expandable structure of a second elongate flexible catheter body at a location in the primary renal artery, expanding the second radially expandable structure such that at least a subset of a plurality of electrodes of the second radially expandable structure engage a wall of the primary renal artery, and energizing at least a subset of the electrodes of the second radially expandable structure to deliver energy to tissue proximate the primary renal artery.

Energizing the electrodes may include a plurality of energization cycles. The electrodes in the subset of energized electrodes may vary between at least some of the energization cycles. An energy output setting of the power source may vary between at least some of the energization cycles.

Another example renal denervation method may include positioning a radially expandable structure of an elongate flexible catheter body in a renal artery connecting an aorta to a kidney. The radially expandable structure may comprise a plurality of electrodes. The method may also include expanding the radially expandable structure such that a subset of the electrodes engage a wall of the renal artery. Another subset of the electrodes may be in the aorta. The method may also include using a power source electrically coupled to the electrodes, energizing at least some of the subset of the electrodes engaged with the wall of the renal artery.

Another example renal denervation method may include positioning a radially expandable structure of an elongate flexible catheter body in a renal artery connecting an aorta to a kidney. The radially expandable structure may comprise a plurality of electrodes. The method may also include expanding the radially expandable structure such that at least a subset of the electrodes engage a wall of the renal artery, using a power source electrically coupled to the electrodes, energizing at least some of the subset of the electrodes engaged with the wall of the renal artery, re-positioning the radially expandable structure to a second position in the renal artery, at the second position, expanding the radially expandable structure such that a subset of the electrodes engage a wall of the renal artery and a different subset of the electrodes are in the aorta, and at the second position, energizing at least some of the subset of the electrodes engaged with the wall of the renal artery.

The renal artery may comprise an accessory renal artery. A primary renal artery may also connect the aorta to the kidney.

An example system for renal denervation of a patient may have a primary renal artery extending between an aorta and a kidney and an accessory renal artery extending between the aorta and the kidney may include a first balloon catheter and a second balloon catheter, each having a balloon with a small profile configuration and a large profile configuration, with a plurality of flexible circuits extending along an outer surface of each balloon, each flexible circuit including at least one electrode. At least one of the balloons may have a large profile configuration that is less than 4 mm in outer diameter. The system may also include a power source configured to electrically couple to the flexible circuits of the first and second balloon catheters and configured to energize at different times the electrodes of the first and second balloon catheters with a renal denervation energy.

One of the balloons may have a large profile configuration that is equal to or greater than 4 mm in outer diameter.

The first and second balloons may have large profile configurations that are different outer diameter sizes.

The system may be for renal denervation of a patient further having a second renal artery extending between the aorta and a second kidney. The system may further comprise a third balloon catheter having a small profile configuration and a large profile configuration, with a plurality of flexible circuits extending along an outer surface of the third balloon, each flexible circuit including at least one electrode. The electrodes of the third balloon catheter may be configured for electrically coupling to the power source.

The first, second and third balloons, when in the large profile configurations, may define different outer diameters from one another.

The outer diameter of the third balloon when in the large profile configuration may be greater than or equal to 4 mm.

An example catheter may include an elongate flexible catheter body. An expandable structure may be associated with the catheter body and including a radially expandable balloon and a plurality of flexible circuits extending along an outer surface of the balloon, each flexible circuit including at least one electrode and at least one temperature sensor. The expandable structure may have an outer diameter of less than 4 mm when in an expanded configuration.

The outer diameter of the expandable structure may be between approximately 1 mm and 3 mm.

The balloon may be non-cannulated.

At least a portion of the outer surface of the balloon may be a flexible polyimide film.

The flexible polyimide film may define a base insulative layer of the plurality of flexible circuits.

An upper surface of the base insulative layer of the balloon may directly contact a conductive layer of at least one of the flexible circuits.

Each flexible circuit may include a base insulative layer adjacent the outer surface of the balloon.

An example system for renal denervation of a patient having a primary renal artery extending between an aorta and a kidney and an accessory renal artery extending between the aorta and the kidney is also disclosed. The system may include a first balloon catheter and a second balloon catheter, each having a balloon with a small profile configuration and a large profile configuration, with a plurality of flexible circuits extending along an outer surface of each balloon, each flexible circuit including at least one electrode, wherein at least one of the balloons has a large profile configuration that is less than 4 mm in outer diameter. A power source may be electrically coupled to the electrodes of the first and second balloon catheters and may be configured to energize the electrodes with a renal denervation energy.

One of the balloons may have a large profile configuration that is equal to or greater than 4 mm in outer diameter.

The first and second balloons may have large profile configurations that are different outer diameter sizes.

The system may be for renal denervation of a patient further having a second renal artery extending between the aorta and a second kidney. The system may further comprise a third balloon catheter having a small profile configuration and a large profile configuration, with a plurality of flexible circuits extending along an outer surface of the third balloon, each flexible circuit including at least one electrode; and wherein the electrodes of the third balloon catheter are electrically coupled to the power source.

The first, second and third balloons, when in the large profile configurations, may define different outer diameters from one another.

The outer diameter of the third balloon when in the large profile configuration may be greater than or equal to 4 mm.

An example renal denervation method may include positioning a radially expandable structure of an elongate flexible catheter body at a location in an accessory renal artery connecting an aorta to a kidney, the aorta and the kidney further connected by a primary renal artery. The radially expandable structure may comprise a plurality of electrodes. The method may further include expanding the radially expandable structure such that at least a subset of the electrodes engage a wall of the accessory renal artery and using a power source electrically coupled to the electrodes, energizing at least a subset of the plurality of electrodes to deliver energy to tissue proximate the accessory renal artery.

The method may also include positioning the radially expandable structure at a location in the primary renal artery, expanding the radially structure such that at least some of the electrodes engage a wall of the primary renal artery, and energizing at least some of the electrodes to deliver energy to tissue proximate the primary renal artery.

The method may also positioning a second radially expandable structure of a second elongate flexible catheter body at a location in the primary renal artery; expanding the second radially expandable structure such that at least a subset of a plurality of electrodes of the second radially expandable structure engage a wall of the primary renal artery; and energizing at least a subset of the electrodes of the second radially expandable structure to deliver energy to tissue proximate the primary renal artery.

Energizing the electrodes may include a plurality of energization cycles. The electrodes in the subset of energized electrodes may vary between at least some of the energization cycles.

An energy output setting of the power source may vary between at least some of the energization cycles.

Another example renal denervation method may include positioning a radially expandable structure of an elongate flexible catheter body in a renal artery connecting an aorta to a kidney. The radially expandable structure may include a plurality of electrodes. The method may also include expanding the radially expandable structure such that a subset of the electrodes engage a wall of the renal artery, wherein another subset of the electrodes are in the aorta, and using a power source electrically coupled to the electrodes, energizing at least some of the subset of the electrodes engaged with the wall of the renal artery.

Another example renal denervation method may include positioning a radially expandable structure of an elongate flexible catheter body in a renal artery connecting an aorta to a kidney. The radially expandable structure may include a plurality of electrodes. The method may also include expanding the radially expandable structure such that at least a subset of the electrodes engage a wall of the renal artery, using a power source electrically coupled to the electrodes, energizing at least some of the subset of the electrodes engaged with the wall of the renal artery, re-positioning the radially expandable structure to a second position in the renal artery, at the second position, expanding the radially expandable structure such that a subset of the electrodes engage a wall of the renal artery and a different subset of the electrodes are in the aorta, and at the second position, energizing at least some of the subset of the electrodes engaged with the wall of the renal artery.

The renal artery may include an accessory renal artery. A primary renal artery may also connect the aorta to the kidney.

Another example system for renal denervation of a patient having a primary renal artery extending between an aorta and a kidney and an accessory renal artery extending between the aorta and the kidney is also disclosed. The system may include a first balloon catheter and a second balloon catheter, each having a balloon with a small profile configuration and a large profile configuration, with a plurality of flexible circuits extending along an outer surface of each balloon, each flexible circuit including at least one electrode. At least one of the balloons may have a large profile configuration that is less than 4 mm in outer diameter. The system may also include a power source configured to electrically couple to the flexible circuits of the first and second balloon catheters and configured to energize at different times the electrodes of the first and second balloon catheters with a renal denervation energy.

One of the balloons may have a large profile configuration that is equal to or greater than 4 mm in outer diameter.

The first and second balloons may have large profile configurations that are different outer diameter sizes.

The system may be for renal denervation of a patient further having a second renal artery extending between the aorta and a second kidney. The system may further include a third balloon catheter having a small profile configuration and a large profile configuration, with a plurality of flexible circuits extending along an outer surface of the third balloon, each flexible circuit including at least one electrode. The electrodes of the third balloon catheter may be configured for electrically coupling to the power source.

The first, second and third balloons, when in the large profile configurations, may define different outer diameters from one another.

The outer diameter of the third balloon when in the large profile configuration may be greater than or equal to 4 mm.

An example method for treating tissue near a body passageway using an apparatus including a catheter having a plurality of electrodes, a radio-frequency energy generator, and a controller coupling the energy generator to the plurality of electrodes and configured to selectively energize the electrodes is also disclosed. The method may include using the apparatus to subject the tissue near the body passageway to a plurality of energy treatment cycles. A treatment cycle may include determining desired voltages for at least a subset of the electrodes for maintaining a predetermined target temperature profile proximate the subset of electrodes, setting an output voltage of the energy generator to correspond to the desired voltage determined for one of the electrodes, and energizing at least some of the electrodes at the output voltage to deliver energy to the body passageway. The electrode used to set the output voltage may change in subsequent treatment cycles in at least some instances.

The treatment cycle may further comprise identifying a first electrode. The first electrode may be used to set the output voltage if the determined voltage requirement for the first electrode is greater than zero.

The identification of the first electrode may cycle through the plurality of electrodes from treatment cycle to treatment cycle.

The treatment cycles may further comprise identifying at least one electrode that is leakage-inducingly proximate to the first electrode. The at least one electrode that is leakage-inducingly proximate to the first electrode may not be energized during the treatment cycle.

The plurality of electrodes may comprise a plurality of bipolar electrodes, and wherein identifying the at least one electrode that is leakage-inducingly proximate to the first electrode may comprise identifying at least one electrode having a negative pole that is leakage-inducingly proximate a positive pole of the first electrode.

Determining desired voltage for an electrode of the subset of electrodes may be based on a previous output voltage applied to the electrode of the subset of electrodes.

Determining desired voltage for the electrode of the subset of electrodes may also be based on differences between a measured temperature proximate the electrode of the subset of electrodes and the target temperature.

Determining desired voltage for the electrode of the subset of electrodes may be based on a current temperature error as well as an average temperature error over time for the electrode of the subset of electrodes.

The desired voltage may equal:

$$V = K_L V_L + K_P T_e + K_I t_{t-n \, sec} T_{e \, AVE}$$

wherein V is the desired voltage, $V_L$ is the previously calculated output voltage, $T_e$ is a temperature error for the electrode of the subset of electrodes, $K_L$, $K_P$ and $K_I$ are constants, and n is a time value ranging from 0 to t seconds.

The desired voltage may equal:

$$V = 0.75 V_L + K_p T_e + K_I \int_{t-1sec}^{t} T_{eAVE}$$

wherein V is the desired voltage, $V_L$ is the previously calculated output voltage, $T_e$ is a temperature error for the electrode of the subset of electrodes, and $K_P$ and $K_I$ are constants.

An example method for treating a body passageway using an apparatus comprising an energy delivery device having a plurality of discrete energy delivery sites, an energy generator, and a controller coupling the energy delivery sites to the energy generator and configured to selectively energize the plurality of energy delivery sites is also disclosed. The method may include using the apparatus to subject the body passageway to a plurality of treatment cycles. At least some of the treatment cycles may include determining a plurality of possible output levels for at least a subset of the energy delivery sites for maintaining a predetermined parameter of the treatment, setting an actual output level of the energy generator to correspond to the possible output level determined for one of the energy delivery sites, and energizing at least some of the energy delivery sites at the actual output level to deliver energy to the body passageway. The energy delivery site may be used to set the actual output level changes from treatment cycle to treatment cycle in at least some instances.

Determining a plurality of possible output levels may include determining a plurality of possible energization times.

Determining a plurality of possible output levels may include determining a plurality of possible output voltages.

Energizing at least some of the energy delivery sites at the actual output level may include energizing at least some of the energy delivery sites associated with a possible output level that is equal to or greater than the actual output level set during the treatment cycle.

Determining the possible output level for one of the energy delivery sites may be based on an output level applied at the energy delivery site in an immediately preceding treatment cycle.

Determining the possible output level for one of the energy delivery sites may also be based on a characterization of an error between an actual condition proximate the energy delivery site and the predetermined parameter.

At least some of the treatment cycles may further comprise identifying from the plurality of energy delivery sites a first energy delivery site.

The identification of the first energy delivery site may cycle through the plurality of energy delivery sites from treatment cycle to treatment cycle.

The possible output level determined for the first energy delivery site may be used to set the actual output level if the possible output level determined for the first energy delivery site is greater than zero.

At least some of the energy delivery sites proximate the first energy delivery site may not be energized during the treatment cycle.

An example method for inducing a desired therapeutic change in tissue using an electrosurgical system is also disclosed. The method may include electrically coupling a plurality of electrodes of the system to a plurality of zones of the tissue and heating the tissue with a plurality of heating cycles. Each heating cycle may have an associated selected zone and may include determining a desired potential for the selected zone in response to a desired characteristic, determining a set of the electrodes appropriate for application of the desired potential, and energizing the selected set of the electrodes with the desired potential. The method may also include monitoring temperature signals from the zones and simultaneously inducing the desired therapeutic change in the tissue of the zones by swapping the selected zone among the zones, and by identifying the desired change and the set of electrodes in response to the temperature signals.

The tissue may be disposed near a body passageway. The plurality of electrodes may be coupled with the zones by expanding an expandable body within the passageway. The electrodes may include bipolar electrodes supported by the expandable body. The desired potentials may include a bipolar electrical potential.

An example system for treating tissue near a body passageway may include a catheter having a plurality of electrodes, a radio-frequency energy generator, and a controller coupling the energy generator to the plurality of electrodes and configured to selectively energize the electrodes during a plurality of energy treatment cycles. During a treatment cycle, the system may be configured to determine desired voltages for at least a subset of the electrodes for maintaining a predetermined target temperature proximate the subset of electrodes, set an output voltage of the energy generator to correspond to the desired voltage determined for one of the electrodes, and energize at least some of the electrodes at the output voltage to deliver energy proximate the body passageway; and wherein the system is configured to vary the electrode used to set the output voltage from treatment cycle to treatment cycle in at least some instances.

An example energy generation apparatus may include a radio-frequency energy generator and a controller. The controller may be configured to couple the energy generator to a catheter having a plurality of electrodes. The controller may be configured to selectively energize the electrodes during a plurality of energy treatment cycles, including determining desired voltages for at least a subset of the electrodes for maintaining a predetermined target temperature proximate the subset of electrode, setting an output voltage of the energy generator to correspond to the desired voltage determined for one of the electrodes, and energizing at least some of the electrodes at the set output voltage to deliver energy to the body passageway. The controller may be configured to vary the electrode used to set the output voltage from treatment cycle to treatment cycle in at least some instances.

An example method for treating a body passageway using an apparatus comprising an energy delivery device having a plurality of discrete energy delivery sites, an energy generator, and a controller coupling the energy delivery sites to the energy generator and configured to selectively energize the plurality of energy delivery sites is also disclosed. The method may include using the apparatus to subject the body passageway to a plurality of treatment cycles. At least some of the treatment cycles may include selecting one of the energy delivery sites as a primary energy delivery site, identifying at least a subset of the energy delivery sites that are not energy leakage-inducingly proximate to the primary energy delivery site, and energizing at least some of the subset of energy delivery sites. The energy delivery site may be selected as the primary energy delivery site changes from treatment cycle to treatment cycle in at least some instances.

An example method for treating tissue near a body passageway using an apparatus having a plurality of electrodes, an energy generator, and a controller coupling the energy generator to the plurality of electrodes and configured to selectively energize the electrodes is also disclosed. The method may include using the apparatus to subject the tissue near the body passageway to a plurality of energy treatment cycles. A treatment cycle may include determining desired power settings for at least a subset of the electrodes for maintaining a predetermined target temperature profile proximate the subset of electrodes, setting an actual power setting of the energy generator to correspond to the desired power setting determined for one of the electrodes, and energizing at least some of the electrodes at the actual power setting to deliver energy to the body passageway. The electrode may be used to set the actual power setting changes in subsequent treatment cycles in at least some instances.

An example method for delivering an energy-based treatment to a tissue proximate a blood vessel is also disclosed. The method may include positioning, at a location in the blood vessel, a radially expandable structure of an elongate flexible catheter body, a plurality of electrodes being positioned on the radially expandable structure; expanding the radially expandable structure such that at least a subset of the electrodes engage a wall of the blood vessel so at to establish a plurality of electrical circuits, each electrical circuit including one of the electrodes and a portion of the tissue within a treatment zone; energizing the plurality of circuits in a time sequence using a power source; and controlling the delivery of energy using a processor coupled with the power source, such controlling including verifying the presence of the electrical circuit, selectively energizing electrodes during the sequence, and regulating one or more parameters of the electrical circuits such that energy delivered to the treatment zone heats tissue therein to a temperature in a target temperature range, thereby inducing a tissue remodeling response.

The electrodes may be selectively energized by identifying an appropriate group of the electrodes and simultaneously energizing the group of electrodes during the sequence, and by repeatedly cycling through the sequence. The group may be determined in response to a plurality of temperature signals associated with the portions of tissue within the treatment zone so that the group changes with the cycles.

The electrodes may comprise monopolar electrodes positioned on the balloon and included in a plurality of flex circuits, each flex circuit including at least one of the monopolar electrodes.

The plurality of flex circuits may further comprise a temperature sensing structure in proximity to at least one of the monopolar electrodes, the temperature sensing structure being electrically coupled to the processor so as to provide feedback.

The balloon may be inflated with an inflation pressure of about 5 atmospheres or less.

An expanded diameter of the expandable structure may be about 2 mm to about 10 mm. For example, an expanded diameter of the expandable structure may be about 3 mm or less.

An example method for delivering an energy-based treatment to a tissue proximate a blood vessel is also disclosed. The method may include positioning an expandable structure of an elongate catheter at a location in the blood vessel, the expandable structure including a plurality of electrodes, at least some of which are longitudinally spaced along the expandable structure, the plurality of electrodes electrically coupled to a power source; expanding the expandable structure such that at least some of the plurality of electrodes contact a tissue; using a processor coupled with the power source, verifying which of the plurality of electrodes are in contact with the tissue; selectively energizing at least one of the electrodes that is in contact with the tissue; and controlling the delivery of energy using the processor to regulate one or more parameters of the energy treatment based on monitoring feedback from electrical circuits associated with at least some of the electrodes such that energy delivered to a treatment zone heats the tissue therein.

Verifying whether one of the electrodes is in contact with the tissue may comprise measuring a characteristic of an electrical circuit associated with the electrode and determining whether the measured characteristic meets a criteria.

Selectively energizing the at least one electrode may comprise energizing electrodes that meet the criteria and not energizing electrodes that do not meet the criteria.

Measuring the characteristic of the electrical circuit may comprise measuring a resistance associated with the electrical circuit.

Selectively energizing the at least one electrode may comprise energizing only the electrodes associated with measured resistances that are within a pre-determined range.

Positioning the expandable structure including the plurality of electrodes may comprise positioning an expandable structure including a plurality of monopolar electrodes.

Positioning the expandable structure comprises positioning an expandable structure including the plurality of monopolar electrodes and a common electrode.

Determining whether the measured characteristic meets the criteria may comprise determining whether a measured characteristic associated with a first monopolar electrode meets a first criteria and determining whether a measured characteristic associated with a second monopolar electrode meets a second criteria. The first and second criteria may be different.

Determining whether the measured characteristic meets the criteria may comprise determining whether a measured characteristic associated with a first monopolar electrode and a measured characteristic associated with a second monopolar electrode meets a single criteria.

An example system for delivering an energy-based treatment to a tissue proximate a blood vessel is also disclosed. The system may include an elongate catheter including an expandable structure at or near a distal end of the catheter. The expandable structure may include a plurality of electrodes, at least some of which are longitudinally spaced apart along the expandable structure. The system may also include a power source electrically coupled to the plurality of electrodes and a processor configured to verify whether at least some of the plurality of electrodes are in contact with the tissue by measuring a characteristic of an electrical circuit associated with the at least some of the plurality of electrodes and determining whether the measured characteristic meets a criteria. The processor may be configured to energize at least one of the plurality of electrodes if the at least one of the plurality of electrodes is verified as in contact with the tissue. The processor may be configured to control the delivery of energy to regulate one or more parameters of the energy treatment based on monitoring feedback from at least some of the electrical circuits such that energy delivered to a treatment zone heats the tissue therein to a temperature of about 55° C. to about 75° C. while tissue collateral to the treatment zone is heated to less than about 45° C.

The plurality of electrodes of the expandable structure may be a plurality of monopolar electrodes.

The expandable structure may further comprise at least one common electrode.

The elongate catheter may further comprise at least one common electrode.

The system may further comprise at least one common electrode pad.

An example method for delivering an energy-based treatment to a tissue proximate a blood vessel is also disclosed. The method may include using an elongate catheter, positioning an expandable structure of an energy-based treatment system at a location in the blood vessel, the expandable structure positioned at or near a distal end of the catheter and including a plurality of monopolar electrodes. The energy-based treatment system may further comprise a common electrode and a power source, the power source electrically coupled to the plurality of monopolar electrodes. The method may also include expanding the expandable structure such that at least some of the plurality of electrodes contact a tissue; using a processor, measuring a characteristic of a plurality of electrical circuits, each electrical circuit associated with one of the plurality of monopolar electrodes and the common electrode; using the processor, identifying a subset of the monopolar electrodes for energization, the identified subset of electrodes having measured characteristics that are within a desired range; and simultaneously energizing the one or more of the monopolar electrodes identified for energization.

The common electrode may be associated with the expandable structure.

Another example method for delivering an energy-based treatment to a tissue proximate a blood vessel may include positioning an expandable structure of an elongate catheter at a location in the blood vessel, the expandable structure positioned at or near a distal end of the catheter and including a plurality of monopolar electrodes, at least some of which are longitudinally spaced along the expandable structure, the plurality of electrodes electrically coupled to a power source; expanding the expandable structure such that at least some of the plurality of electrodes contact a tissue; selectively energizing a subset of the plurality of electrodes; and controlling the delivery of energy using a processor to regulate one or more parameters of the energy treatment based on monitoring feedback from electrical circuits associated with at least some of the electrodes such that energy delivered to a treatment zone heats the tissue therein to a temperature in a desired range.

The method may also include, prior to selectively energizing the subset of the plurality of electrodes, identifying, using a processor, the subset of electrodes for energization.

Identifying the subset of electrodes may include measuring a characteristic of an electrical circuit associated with each of the plurality of electrodes.

Identifying the subset of electrodes may further comprise comparing, using the processor, the measured characteristics to identify the subset for energization.

Identifying the subset for energization may comprise identifying a group of the electrodes with substantially similar measured characteristics.

Identifying the subset of electrodes may further comprise determining whether the measured characteristic associated with each of the plurality of electrodes meets a predetermined requirement.

Determining whether the measured characteristic associated with each of the plurality of electrodes meets a predetermined requirement may comprise determining whether the measured characteristic associated with each of the plurality of electrodes comes within a pre-determined range.

Determining whether the measured characteristic associated with each of the plurality of electrodes comes within a pre-determined range may comprise using the same pre-determined range for each of the electrodes.

Determining whether the measured characteristic associated with each of the plurality of electrodes comes within a pre-determined range may comprise using a different pre-determined range for at least some of the electrodes.

An example method for treating tissue near a body passageway using an apparatus including a catheter having a plurality of monopolar electrodes, a radio-frequency energy generator, and a controller coupling the energy generator to the monopolar electrodes and configured to selectively energize the monopolar electrodes is also disclose. The method may include using the apparatus to subject the tissue near the body passageway to a plurality of energy treatment cycles. A treatment cycle may include determining desired voltages for at least a subset of the monopolar electrodes for determining a predetermined target temperature profile proximate the subset of monopolar electrodes; setting an output voltage of the energy generator to correspond to the desired voltage determined for one of the monopolar electrodes; and energizing at least one of the monopolar electrodes at the output voltage to deliver energy to the body passageway. The monopolar electrode may be used to set the output voltage changes in subsequent treatment cycles in at least some instances.

The treatment cycle further may include identifying a first monopolar electrode; wherein the first monopolar electrode is used to set the output voltage if the determined voltage requirement for the first monopolar electrode is greater than zero.

The identification of the first monopolar electrode may cycle through the plurality of monopolar electrodes from treatment cycle to treatment cycle.

The treatment cycle may further comprise identifying at least one monopolar electrode that is associated with an electrical circuit characteristic that is substantially different from an electrical circuit characteristic associated with the first monopolar electrode. The at least one monopolar electrode associated with the substantially different electrical circuit characteristic may not be energized during the treatment cycle.

The electrical circuit characteristic utilized for the identification may be an impedance measurement.

An example method for treating a body passageway using an apparatus comprising an energy delivery device having a plurality of discrete monopolar energy delivery sites, a common electrode, an energy generator, and a controller coupling the monopolar energy delivery sites to the energy generator and configured to selectively energize the plurality of monopolar energy delivery sites is also disclosed. The method may include using the apparatus to subject the body passageway to a plurality of treatment cycles. At least some of the treatment cycles may comprise determining a plurality of possible output levels for at least a subset of the monopolar energy delivery sites for maintaining a predetermined parameter of the treatment; setting an actual output level of the energy generator to correspond to the possible output level determined for one of the monopolar energy delivery sites; and energizing at least some of the monopolar energy delivery sites at the actual output level to deliver energy to the body passageway. The monopolar energy delivery site used to set the actual output level may change from treatment cycle to treatment cycle in at least some instances.

An example method for treating a patient having congestive heart failure is also disclosed. The method may include positioning an expandable balloon in a renal artery of the patient, the expandable balloon including a plurality of electrode assemblies, at least some of the electrode assemblies each including at least two bipolar electrode pairs, the two bipolar electrode pairs being longitudinally and circumferentially offset from one another; expanding the balloon in the renal artery such that at least some of the bipolar electrode pairs are electrically coupled to a wall of the renal artery; and energizing at least some of the bipolar electrode pairs so as to therapeutically alter at least one nerve proximate the renal artery to treat the patient's congestive heart failure.

Energizing at least some of the bipolar electrode pairs may comprise using a plurality of temperature sensors to adjust an energy output of the bipolar electrode pairs, each sensor positioned between one of the bipolar electrode pairs.

Positioning the expandable balloon in the renal artery of the patient may comprise positioning an expandable balloon in which the bipolar electrode pairs of the electrode assemblies are longitudinally offset from circumferentially adjacent bipolar electrode pairs.

Another example method for treating a patient having congestive heart failure may include positioning an expandable device including an array of energy delivery structures in a renal artery of the patient; expanding the expandable device such that at least some of the energy delivery structures are proximate a wall of the renal artery; and energizing at least some of the energy delivery structures so as to therapeutically alter at least one nerve proximate the renal artery to treat the patient's congestive heart failure.

The energy delivery structures may be energized for less than ten minutes during the treatment, or the energy delivery structures may be energized for less than five minutes during the treatment, or the energy delivery structures may be energized for less than one minute during the treatment.

The energy delivery structures may be energized with the expandable device at only one position in the patient's renal artery during the treatment.

An example method of treating congestive heart failure may include subjecting a renal tissue of a patient to radio frequency energies for less than ten minutes such that the treatment is effective to reduce norepinephrine concentrations in the patient by greater than 50% in order to treat the patient's congestive heart failure.

The treatment may be effective to reduce norepinephrine concentrations proximate the renal tissue by greater than 50%.

Subjecting the renal tissue to radio frequency energies for less than ten minutes may comprise subjecting the renal tissue to radio frequency energies for less than five minutes.

Subjecting the renal tissue to radio frequency energies for less than five minutes comprises subjecting the renal tissue to radio frequency energies for less than one minute.

Subjecting the renal tissue to radio frequency energies may comprise raising a temperature proximate the renal tissue to a temperature approximately in the range of 50° C. to 80° C.

Raising the temperature to the temperature approximately in the range of 50° C. to 80° C. may comprise raising the temperature to a temperature approximately in the range of 55° C. to 75° C. Raising the temperature to the temperature approximately in the range of 55° C. to 75° C. may comprise raising the temperature to a target temperature of approximately 68° C.

Raising the temperature to the target temperature of 68° C. may further comprise raising the temperature such that a rate of temperature change gradually decreases as the temperature approaches the target temperature.

Raising the temperature such that the rate of temperature change gradually decreases as the temperature approaches the target temperature may comprise raising the temperature such that the rate of temperature change linearly decreases as the temperature approaches the target temperature.

Subjecting the renal tissue to radio frequency energies may comprise inserting a catheter including a plurality of electrodes into a renal artery such that the electrodes are positioned proximate the renal tissue and selectively energizing the plurality of electrodes.

The congestive heart failure may be systolic congestive heart failure.

The congestive heart failure may be diastolic congestive heart failure.

An example renal-denervation treatment method may include delivering an RF energy treatment to a tissue proximate a renal artery using a catheter assembly of a renal denervation catheter system. The denervation system may include an RF energy generator coupled with the catheter assembly by a controller. The method may also include applying neural activity stimulation to the tissue proximate the renal artery using the catheter assembly; assessing stimulated neural activity response of the tissue using the catheter assembly; and determining a parameter of the RF energy treatment based on the assessed neural activity.

The method may also include outputting data relating to the assessed neural activity.

Outputting data may include outputting whether a sufficient decrease in neural activity has occurred.

Assessing the neural activity may include taking at least a first neural activity measurement and a second neural activity measurement.

Taking the first neural activity measurement may comprise taking the first neural activity measurement before beginning the delivery of the RF energy treatment to establish a base line neural activity measurement. Taking the second neural activity measurement may comprise taking the second neural activity measurement after beginning the delivery of the RF energy treatment. The method may also include determining whether neural activity has changed from the base line.

Determining whether neural activity has changed from the base line may include determining whether the change in neural activity is at, above or below a threshold.

The method may also include terminating the RF energy treatment once the change in neural activity is at or above the threshold.

Sensing stimulated neural activity response may comprise periodically measuring for stimulated neural activity response during the RF energy treatment.

Applying neural activity stimulation may comprise energizing at least one electrode of the catheter assembly. Assessing stimulated neural activity response may comprise using a second electrode of the catheter assembly to monitor for the nerve response signal.

Delivering the RF energy treatment may comprise using the at least one electrode and the second electrode to deliver RF energy to the tissue.

Delivering the RF energy treatment may comprise using the catheter assembly with the at least one electrode at a proximal end of an expandable device and the second electrode at a distal end of the device.

Delivering the RF energy treatment may comprise using the catheter assembly with the at least one electrode and the second electrode being at least one of laterally and circumferentially offset relative to one another.

Delivering the RF energy treatment may comprise using a plurality of electrodes other than the at least one electrode and the second electrode.

Monitoring for the nerve response signal may comprise at least one of measuring an amplitude of the nerve response signal, measuring a time delay between the nerve stimulation signal and the nerve response signal, and measuring a fractionated amplitude of the nerve response signal.

The method may also include measuring at least one of an amplitude of the nerve response signal, a pulse width of the nerve response signal, a slope or change in slope of the nerve response signal, a velocity of the nerve response signal, or a time delay of the nerve response signal.

The method may also include comparing the measurement to a base line measurement of an earlier nerve response signal.

Determining the at least one parameter of the RF energy treatment may comprise adjusting the at least one parameter based on the assessed neural activity.

Adjusting the at least one parameter may comprise adjusting a temperature profile of the RF energy treatment.

Adjusting the at least one parameter may comprise adjusting a length of time at a target temperature of the target temperature profile.

Adjusting the at least one parameter may comprise adjusting a voltage setting of the RF energy generator.

Adjusting the at least one parameter may comprise adjusting the voltage setting while maintaining a target temperature constant.

The method may also include terminating the RF energy treatment after a pre-determined period of time if the assessed neural activity is not below a threshold level.

The method may also include repositioning the catheter assembly and delivering a second RF energy treatment to a second tissue portion proximate the renal artery.

Determining the parameter of the RF energy treatment may further comprise determining the parameter of the RF energy treatment based on the assessed neural activity and a temperature measurement of the tissue.

Another example renal-denervation method may include applying a first neural activity stimulation to a tissue proximate a catheter assembly of a renal denervation system; measuring a first stimulated neural activity response of the tissue using the catheter assembly; delivering an energy treatment to the tissue proximate the renal artery using the catheter assembly; measuring a second neural activity response of the neural tissue using the catheter assembly; and determining a parameter of the energy treatment by comparing the first and second measured neural activities.

Comparing the first and second measured neural activities may comprise comparing at least one of a signal amplitude of the first and second neural activities, a time delay associated with the first and second neural activities, a pulse width of the first and second neural activities, a velocity of the first and second neural activities, and a slope or a change in slope of the first and second neural activities.

Another example denervation method may include delivering an energy treatment to a tissue proximate a body lumen using an implanted device; assessing a neural activity of the tissue using the implanted device; and determining, at least in part, at least one parameter of the energy treatment using the assessed neural activity.

Another example renal-denervation treatment method may include positioning a catheter-based assembly in a renal artery, proximate a body tissue; delivering an energy treatment to the body tissue using the catheter-based assembly; during or after the energy treatment, assessing whether a neural activity level of the body tissue has decreased; and removing the catheter-based assembly from the renal artery after a sufficient decrease in the neural activity level.

The treatment may be effective to reduce norepinephrine concentrations in a patient by greater than 50%.

The treatment may be effective to reduce norepinephrine concentrations in the body tissue proximate the renal artery by greater than 50%.

The treatment may be effective to reduce a systolic blood pressure of a patient by at least 5%, or by at least 10%, or by at least 20%.

The treatment may be effective to reduce a diastolic blood pressure of a patient by at least 5%, or by at least 10%, or by at least 20%.

An example renal-denervation treatment system may include an elongate catheter including an expandable structure at or near a distal end of the catheter. The expandable structure may include a plurality of electrodes. A power source may be electrically coupled to the plurality of electrode. The system may also include a processor configured to energize at least a subset of the electrodes at a renal-denervation energy level, energize one or more of the electrodes at a neural activity stimulation level, and monitor for, using one or more of the electrodes, a neural activity response.

The neural activity stimulation level may be a voltage in the range of about 0.1 V to about 5 V applied for about 1 second or less. For example, the neural activity stimulation level may be about 0.5 V applied for about 0.5 milliseconds.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

FIGS. 4A-4C are top views of various example electrode assemblies having single distal electrode pads.

FIGS. 5A-5F are top views of various example electrode assemblies having single proximal electrode pads.

FIGS. 5G-I are top views of various example monopolar electrode assemblies.

FIG. 6 is a cross-sectional view of the system of FIG. 1A being used to remodel a body passageway.

FIGS. 7-10 illustrate various, non-limiting, examples of temperature profiles.

FIGS. 11 and 12 illustrate experimental results from a comparison of certain, non-limiting, examples of temperature profiles.

FIGS. 25-30 illustrate one experiment assessing efficacy and safety of an example system for renal denervation.

DETAILED DESCRIPTION

Figure 1A:
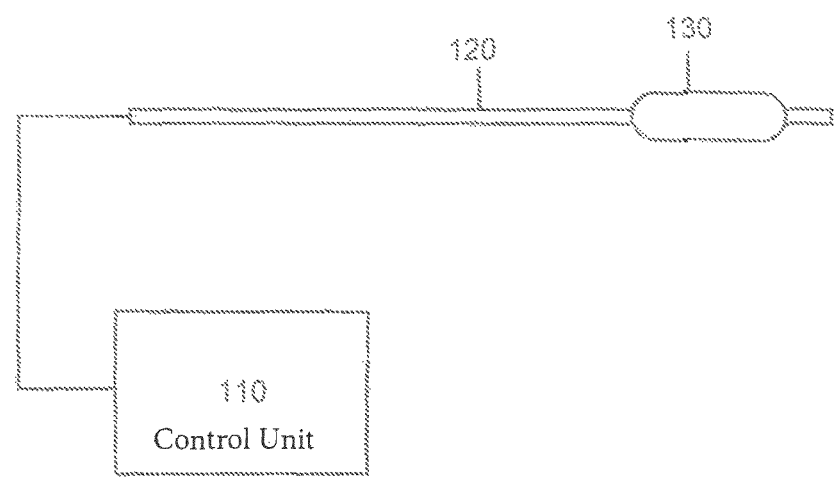
FIG. 1A shows a simplified schematic of an example system for remodeling tissue.

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Physicians use catheters to gain access to and affect therapies by altering interior tissues of the body, particularly within or about the lumens of the body such as blood vessels. For example, balloon angioplasty and other catheters often are used to open arteries that have been narrowed due to atherosclerotic disease.

Catheters can be used to perform renal denervation by RF energy treatment in patients with refractory hypertension. This is a relatively new procedure, which has been found to be clinically effective in treating hypertension. In the procedure, RF energy is applied to walls of the renal artery to reduce hyper-activation (which is often the cause of chronic hypertension) of the sympathetic nervous system adjacent to the renal artery. This procedure has been found to be successful in some cases, but also is associated with a significant amount of pain, and existing treatments can be both relatively difficult for the physician to accurately perform and quite time-consuming.

Another condition affecting many patients is Congestive Heart Failure ("CHF"). CHF is a condition which occurs when the heart becomes damaged and blood flow is reduced to the organs of the body. If blood flow decreases sufficiently, kidney function becomes altered, which results in fluid retention, abnormal hormone secretions and increased constriction of blood vessels. These results increase the workload of the heart and further decrease the capacity of the heart to pump blood through the kidneys and circulatory system.

It is believed that progressively decreasing perfusion of the kidneys is a principal non-cardiac cause perpetuating the downward spiral of CHF. For example, as the heart struggles to pump blood, the cardiac output is maintained or decreased and the kidneys conserve fluid and electrolytes to maintain the stroke volume of the heart. The resulting increase in pressure further overloads the cardiac muscle such that the cardiac muscle has to work harder to pump against a higher pressure. The already damaged cardiac muscle is then further stressed and damaged by the increased pressure. In addition to exacerbating heart failure, kidney failure can lead to a downward spiral and further worsening kidney function. For example, in the forward flow heart failure described above, (systolic heart failure) the kidney becomes ischemic. In backward heart failure (diastolic heart failure), the kidneys become congested vis-a-vis renal vein hypertension. Therefore, the kidney can contribute to its own worsening failure.

The functions of the kidneys can be summarized under three broad categories: filtering blood and excreting waste products generated by the body's metabolism; regulating salt, water, electrolyte and acid-base balance; and secreting hormones to maintain vital organ blood flow. Without properly functioning kidneys, a patient will suffer water retention, reduced urine flow and an accumulation of waste toxins in the blood and body. These conditions result from reduced renal function or renal failure (kidney failure) and are believed to increase the workload of the heart. In a CHF patient, renal failure will cause the heart to further deteriorate as fluids are retained and blood toxins accumulate due to the poorly functioning kidneys. The resulting hypertension also has dramatic influence on the progression of cerebrovascular disease and stroke.

The autonomic nervous system is a network of nerves that affect almost every organ and physiologic system to a variable degree. Generally, the system is composed of sympathetic and parasympathetic nerves. For example, the sympathetic nerves to the kidney traverse the sympathetic chain along the spine and synapse within the ganglia of the chain or within the celiac ganglia, then proceeding to innervate the kidney via post-ganglionic fibers inside the "renal nerves". Within the renal nerves, which travel along the renal hila (artery and to some extent the vein), are the post-ganglionic sympathetic nerves and the afferent nerves from the kidney. The afferent nerves from the kidney travel within the dorsal root (if they are pain fibers) and into the anterior root if they are sensory fibers, then into the spinal cord and ultimately to specialized regions of the brain. The afferent nerves, baroreceptors and chemoreceptors, deliver information from the kidneys back to the sympathetic nervous system via the brain; their ablation or inhibition is at least partially responsible for the improvement seen in blood pressure after renal nerve ablation, or denervation, or partial disruption. It has also been suggested and partially proven experimentally that the baroreceptor response at the level of the carotid sinus is mediated by the renal artery afferent nerves such that loss of the renal artery afferent nerve response blunts the response of the carotid baroreceptors to changes in arterial blood pressure (American J. Physiology and Renal Physiology 279:F491-F501, 2000, the disclosure of which is incorporated herein by reference).

It has been established in animal models that the heart failure condition results in abnormally high sympathetic activation of the kidneys. An increase in renal sympathetic nerve activity leads to decreased removal of water and sodium from the body, as well as increased renin secretion which stimulates aldosterone secretion from the adrenal gland. Increased renin secretion can lead to an increase in angiotensin II levels, which leads to vasoconstriction of blood vessels supplying the kidneys as well as systemic vasoconstriction, all of which lead to a decrease in renal blood flow and hypertension. Reduction in sympathetic renal nerve activity, e.g., via de-innervation, may reverse these processes and in fact has been shown to in the clinic.

As with hypertension, sympathetic nerve overdrive contributes to the development and progression of CHF. Norepinephrine spillover from the kidney and heart to the venous plasma is even higher in CHF patients compared to those with essential hypertension. Chronic sympathetic nerve stimulation overworks the heart, both directly as the heart increases its output and indirectly as a constricted vasculature presents a higher resistance for the heart to pump against. As the heart strains to pump more blood, left ventricular mass increases and cardiac remodeling occurs. Cardiac remodeling results in a heterogeneous sympathetic activation of the heart which further disrupts the synchrony of the heart contraction. Thus, remodeling initially helps increase the pumping of the heart but ultimately diminishes the efficiency of the heart. Decrease in function of the left ventricle further activates the sympathetic nervous system and the renin-angiotensin-aldosterone system, driving the vicious cycle that leads from hypertension to CHF.

Embodiments of the present disclosure relate to a power generating and control apparatus, often for the treatment of targeted tissue in order to achieve a therapeutic effect. In some embodiments, the target tissue is tissue containing or proximate to nerves, including renal arteries and associated renal nerves. In other embodiments the target tissue is luminal tissue, which may further comprise diseased tissue such as that found in arterial disease.

In yet another exemplary embodiment of the present disclosure, the ability to deliver energy in a targeted dosage may be used for nerve tissue in order to achieve beneficial biologic responses. For example, chronic pain, urologic dysfunction, hypertension, and a wide variety of other persistent conditions are known to be affected through the operation of nervous tissue. For example, it is known that chronic hypertension that may not be responsive to medication may be improved or eliminated by disabling excessive nerve activity proximate to the renal arteries. It is also known that nervous tissue does not naturally possess regenerative characteristics. Therefore it may be possible to beneficially affect excessive nerve activity by disrupting the conductive pathway of the nervous tissue. When disrupting nerve conductive pathways, it is particularly advantageous to avoid damage to neighboring nerves or organ tissue. The ability to direct and control energy dosage is well-suited to the treatment of nerve tissue. Whether in a heating or ablating energy dosage, the precise control of energy delivery as described and disclosed herein may be directed to the nerve tissue. Moreover, directed application of energy may suffice to target a nerve without the need to be in exact contact, as would be required when using a typical ablation probe. For example, eccentric heating may be applied at a temperature high enough to denature nerve tissue without causing ablation and without requiring the piercing of luminal tissue. However, it may also be desirable to configure the energy delivery surface of the present disclosure to pierce tissue and deliver ablating energy similar to an ablation probe with the exact energy dosage being controlled by a power control and generation apparatus.

In some embodiments, efficacy of the denervation treatment can be assessed by measurement before, during, and/or after the treatment to tailor one or more parameters of the treatment to the particular patient or to identify the need for additional treatments. For instance, a denervation system may include functionality for assessing whether a treatment has caused or is causing a reduction in neural activity in a target or proximate tissue, which may provide feedback for adjusting parameters of the treatment or indicate the necessity for additional treatments.

While the disclosure focuses on the use of the technology in the vasculature, the technology would also be useful for other luminal tissues. Other anatomical structures in which the present disclosure may be used are the esophagus, the oral cavity, the nasopharyngeal cavity, the auditory tube and tympanic cavity, the sinus of the brain, the arterial system, the venous system, the heart, the larynx, the trachea, the bronchus, the stomach, the duodenum, the ileum, the colon, the rectum, the bladder, the ureter, the ejaculatory duct, the vas deferens, the urethra, the uterine cavity, the vaginal canal, and the cervical canal.

System Overview

FIG. 1A shows a system 100 for performing a treatment within a body passageway. The system 100 includes a control unit 110. The control unit 110 can include an RF generator for delivering RF energy to catheter device 120. An exemplary control unit and associated energy delivery methods useable with the embodiments disclosed herein are disclosed in commonly assigned U.S. Pat. App. Pub. No. US 2012/0095461, which is incorporated by reference herein. Further examples useable with the embodiments disclosed herein are disclosed in commonly assigned U.S. Pat. No. 7,742,795 entitled "Tuned RF Energy for Selective Treatment of Atheroma and Other Target Tissues and/or Structures", U.S. Pat. No. 7,291,146 entitled "Selectable Eccentric Remodeling and/or Ablation of Atherosclerotic Material", and U.S. Pub. No. 2008/0188912 entitled "System for Inducing Desirable Temperature Effects on Body Tissue", the full disclosures of which are incorporated herein by reference. In some embodiments, particularly in some embodiments utilizing monopolar energy delivery, the system may also include a ground/common electrode, which may be associated with the catheter device, a separate pad that is electrically coupled to the control unit 110, or otherwise associated with system 100.

In some embodiments, the control unit 110 may include a processor or otherwise be coupled to a processor to control or record treatment. The processor will typically comprise computer hardware and/or software, often including one or more programmable processor units running machine readable program instructions or code for implementing some, or all, of one or more of the embodiments and methods described herein. The code will often be embodied in a tangible media such as a memory (optionally a read only memory, a random access memory, a non-volatile memory, or the like) and/or a recording media (such as a floppy disk, a hard drive, a CD, a DVD, a non-volatile solid-state memory card, or the like). The code and/or associated data and signals may also be transmitted to or from the processor via a network connection (such as a wireless network, an ethernet, an internet, an intranet, or the like), and some or all of the code may also be transmitted between components of a catheter system and within the processor via one or more buses, and appropriate standard or proprietary communications cards, connectors, cables, and the like will often be included in the processor. The processor may often be configured to perform the calculations and signal transmission steps described herein at least in part by programming the processor with the software code, which may be written as a single program, a series of separate subroutines or related programs, or the like. The processor may comprise standard or proprietary digital and/or analog signal processing hardware, software, and/or firmware, and may desirable have sufficient processing power to perform the calculations described herein during treatment of the patient, the processor optionally comprising a personal computer, a notebook computer, a tablet computer, a proprietary processing unit, or a combination thereof. Standard or proprietary input devices (such as a mouse, keyboard, touchscreen, joystick, etc.) and output devices (such as a printer, speakers, display, etc.) associated with modern computer systems may also be included, and processors having a plurality of processing units (or even separate computers) may be employed in a wide range of centralized or distributed data processing architectures.

In some embodiments, control software for the system 100 may use a client-server schema to further enhance system ease of use, flexibility, and reliability. "Clients" are the system control logic; "servers" are the control hardware. A communications manager delivers changes in system conditions to subscribing clients and servers. Clients "know" what the present system condition is, and what command or decision to perform based on a specific change in condition. Servers perform the system function based on client commands. Because the communications manager is a centralized information manager, new system hardware may not require changes to prior existing client-server relationships; new system hardware and its related control logic may then merely become an additional "subscriber" to information managed through the communications manager. This control schema may provide the benefit of having a robust central operating program with base routines that are fixed; no change to base routines may be necessary in order to operate new circuit components designed to operate with the system.

Expandable Device and Electrode Assemblies

Returning to FIG. 1A, the catheter device 120 can include an expandable device 130, which can be a compliant, non-compliant, or semi-compliant balloon. The expandable device 130 includes a plurality of electrode assemblies electrically coupled to the control unit 110. Such electrode assemblies can be electrically configured to be monopolar or bipolar, and further have heat sensing capability.

Figure 1B:
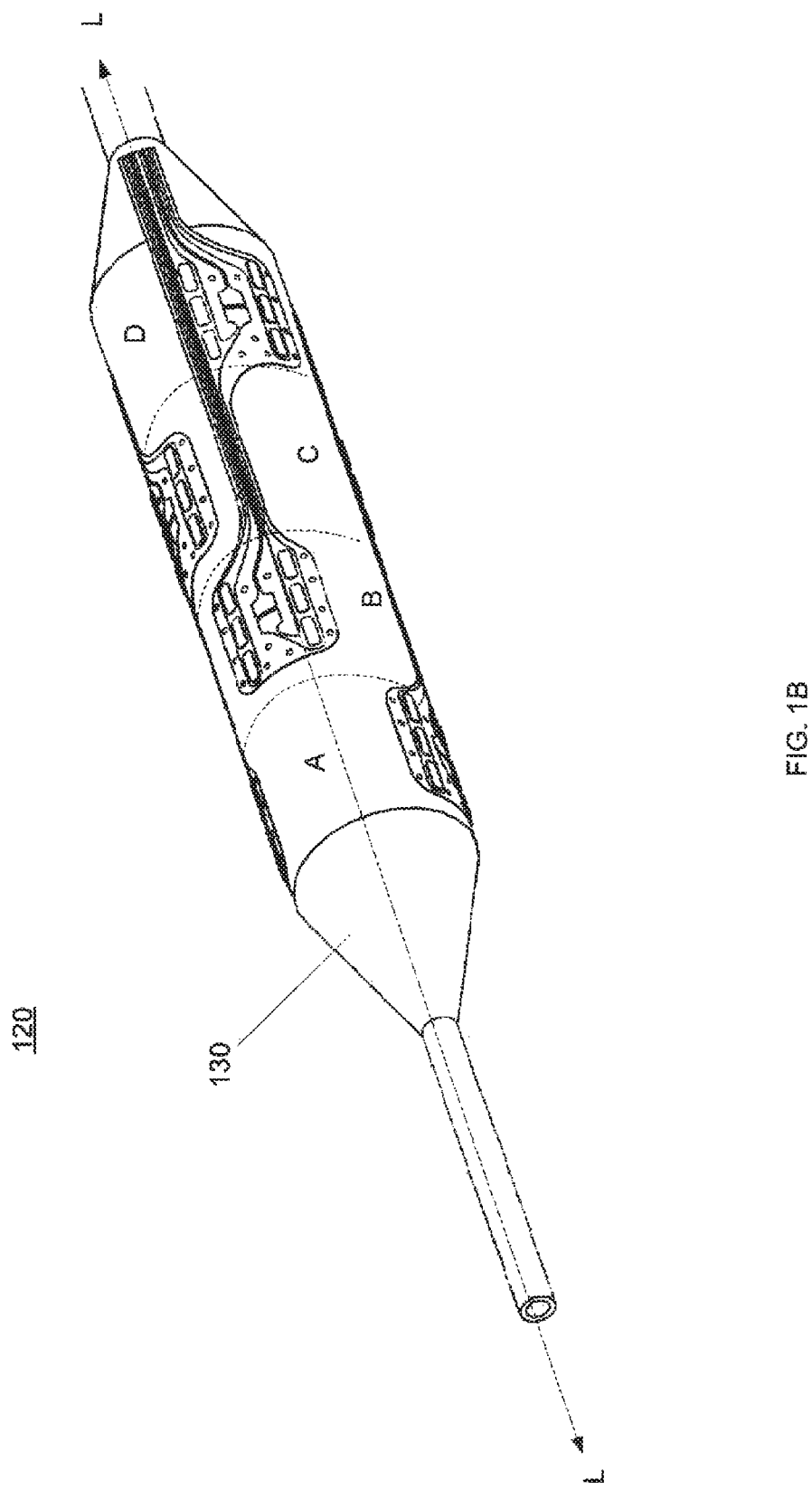
FIG. 1B is a perspective view of an example expandable device of a catheter.

As shown in FIG. 1B, the electrode assemblies may be arranged on the expandable device 130, shown here in an expanded state, according to a plurality of cylindrical treatment zones A-D. In other embodiments, some of which are described further below, the expandable device 130 or other components of the treatment system may include additional electrode assemblies that are not in a treatment zone or are otherwise not used or configured to deliver a treatment energy.

Figure 1C:
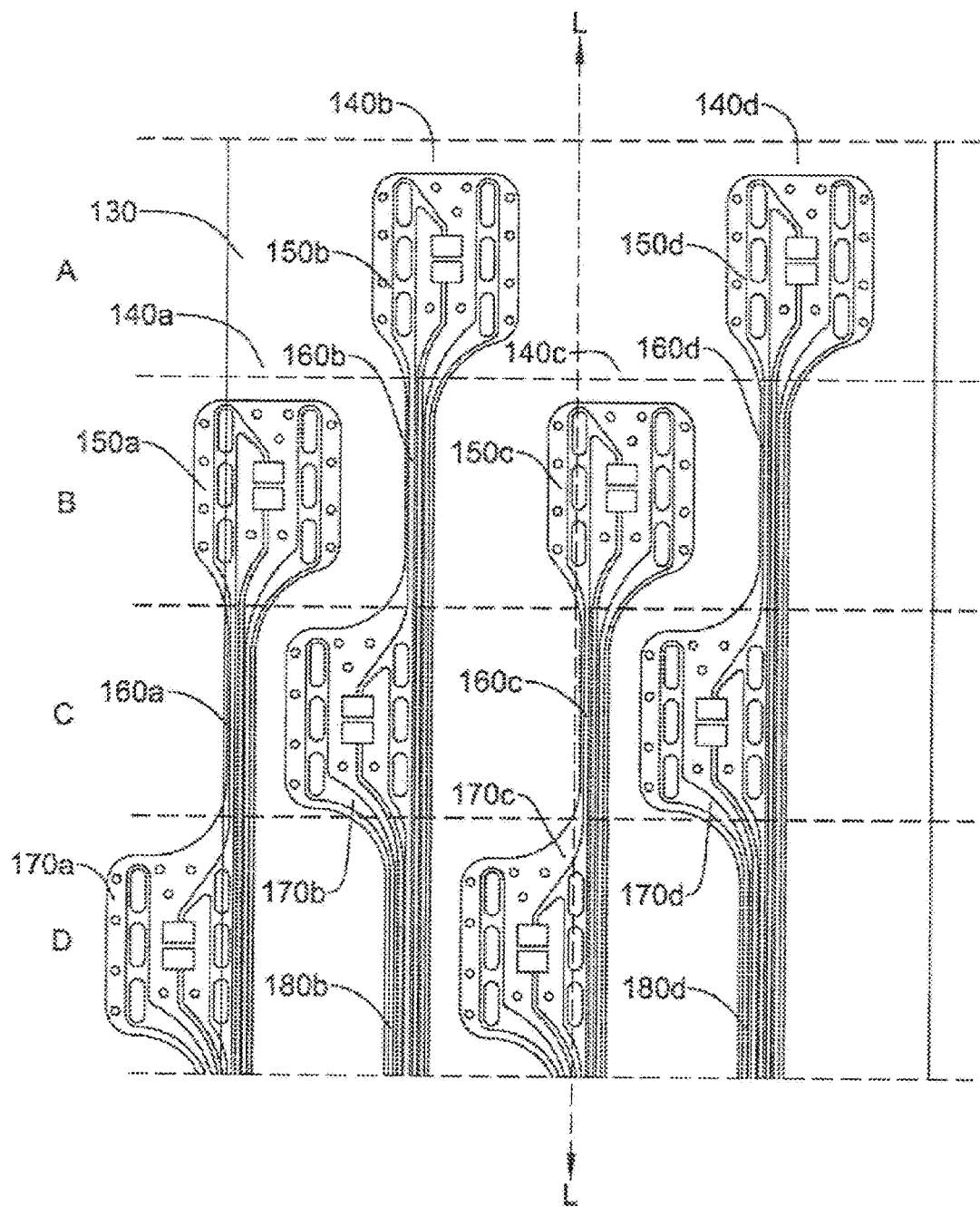
FIG. 1C is a top view of the expandable device of FIG. 1B in an unrolled configuration.
Figure 1D:
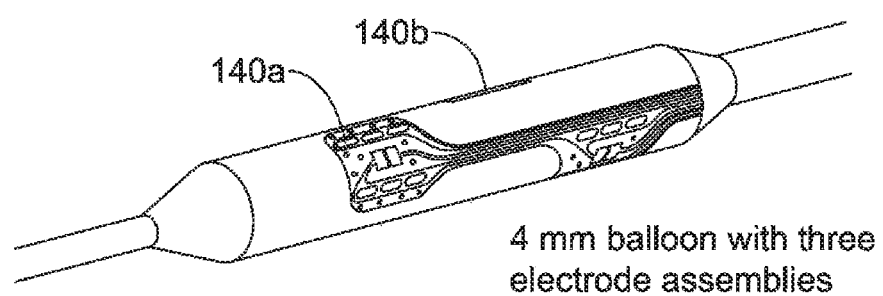
FIGS. 1D and 1E are perspective views of example expandable devices.
Figure 1E:
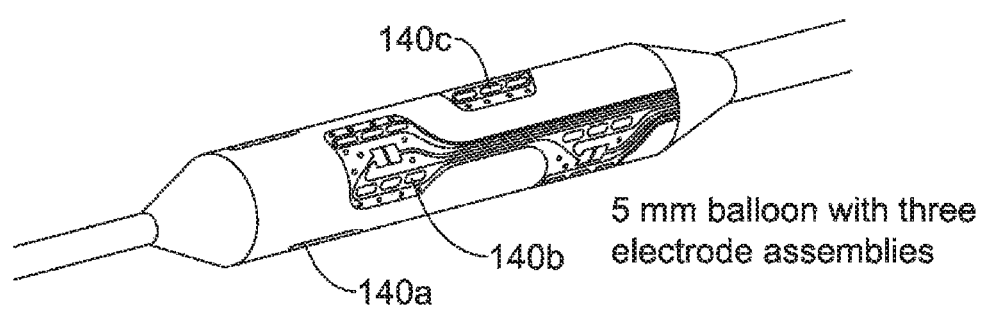

The treatment zones A-D and associated electrode assemblies 140a-d are further illustrated in FIG. 1C, which is an "unrolled" depiction of the expandable device 130 of FIG. 1B. In some embodiments, the expandable device is a balloon with a 4 mm diameter and two electrode assemblies 140a-b. In other embodiments, the expandable device is a balloon with a 5 mm diameter and three electrode assemblies 140*a-c*. In some embodiments, the expandable device is a balloon with a 6, 7, or 8 mm diameter and four electrode assemblies 140*a-d*, as depicted in FIG. 1B. A 4 mm balloon having two electrode assemblies 140*a,b* is shown in FIG. 1D and a 5 mm balloon having three electrode assemblies 140*a-c* is shown in FIG. 1E. For any of these configurations, the expandable device may have a working length of about 10 mm to about 100 mm, or about 18 mm to about 25 mm, which is the approximate longitudinal span of all the treatment zones A-D shown in FIGS. 1B and 1C. The electrode assemblies 140*a-d* can be attached to a balloon using adhesive.

Figure 1F:
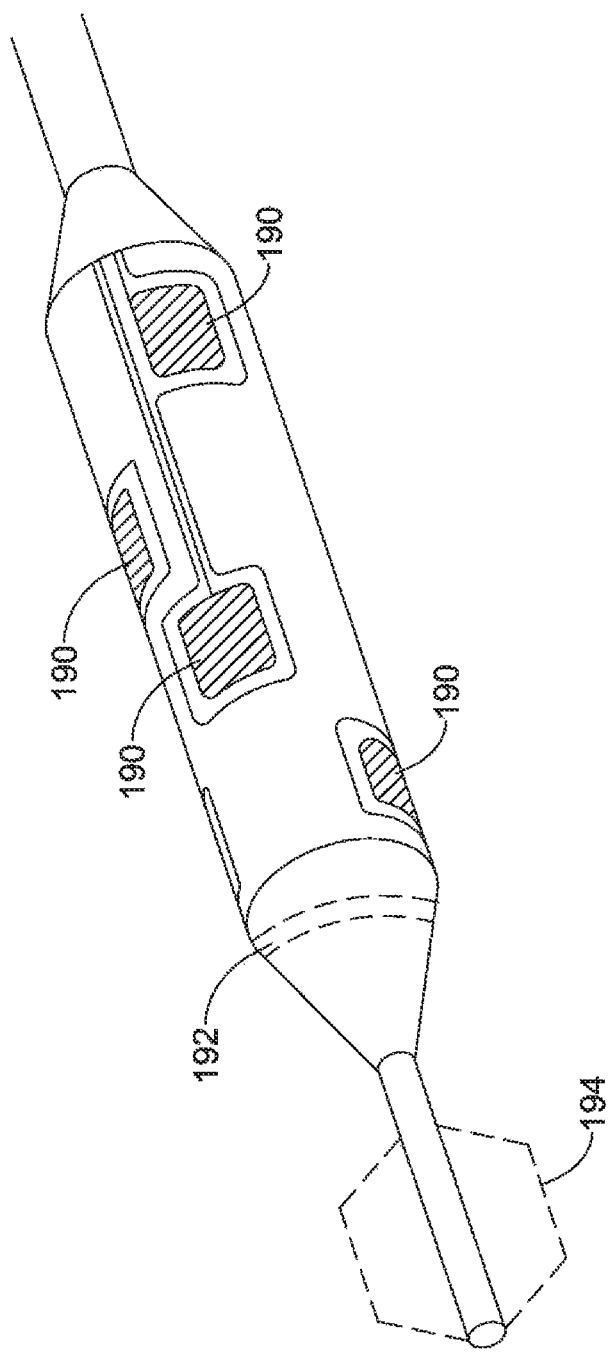
FIG. 1F is a perspective view of an example expandable device.

FIG. 1F schematically illustrates an embodiment of an expandable device that includes an array of monopolar electrodes 190 (although, the electrode arrays illustrated in FIGS. 1B through 1E and other figures may also be used in a monopolar configuration). In some instances, one of the monopolar electrodes 190 on the expandable device may be configured to function as a common or ground electrode for the other electrodes. Alternatively, separate or differently shaped and configured electrodes on the expandable device (such as ring electrode 192 illustrated in broken lines in FIG. 1F) or electrodes on other expandable devices (e.g. 194 in FIG. 1F) or otherwise associated with the catheter may be configured as a common electrode. In still other instances, a grounding pad may be secured to the patient's skin to function as the common electrode. Although not shown explicitly in FIG. 1F, the monopolar electrodes may each be positioned proximate or on a temperature sensing device, similar to other embodiments described herein.

a. Overlapping and Non-Overlapping Treatment Zones

Returning to FIG. 1B, the treatment zones A-D are longitudinally adjacent to one another along longitudinal axis L-L, and may be configured such that energy applied by the electrode assemblies create treatments that do not overlap. Treatments applied by the longitudinally adjacent bipolar electrode assemblies 140*a-d* are circumferentially non-continuous along longitudinal axis L-L. For example, with reference to FIG. 1C, lesions created in treatment zone A may in some embodiments minimize overlap about a circumference (laterally with respect to L-L in this view) with lesions created in treatment zone B.

Figure 31:
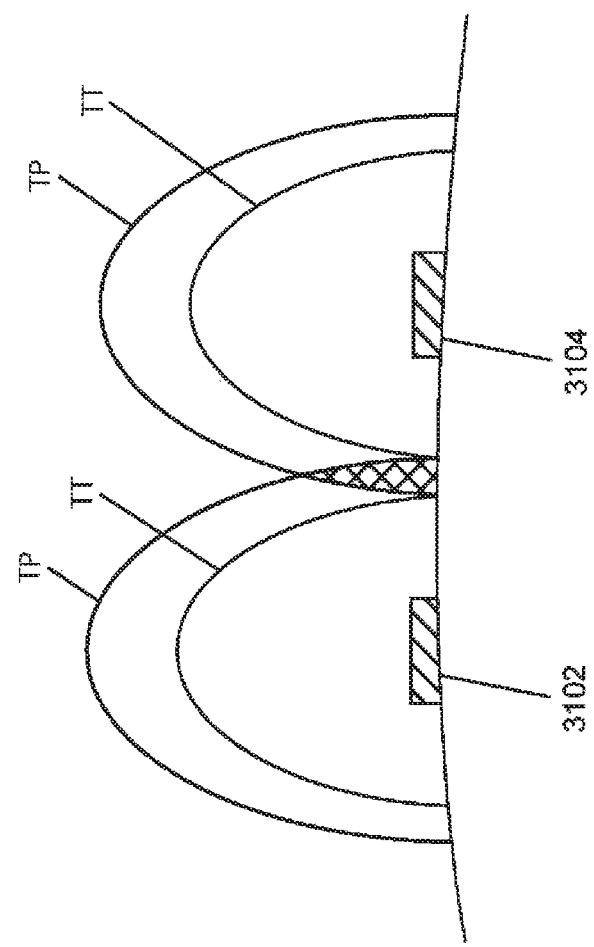
FIGS. 31 and 32 schematically illustrate example treatment zones associated with two electrodes.
Figure 32:
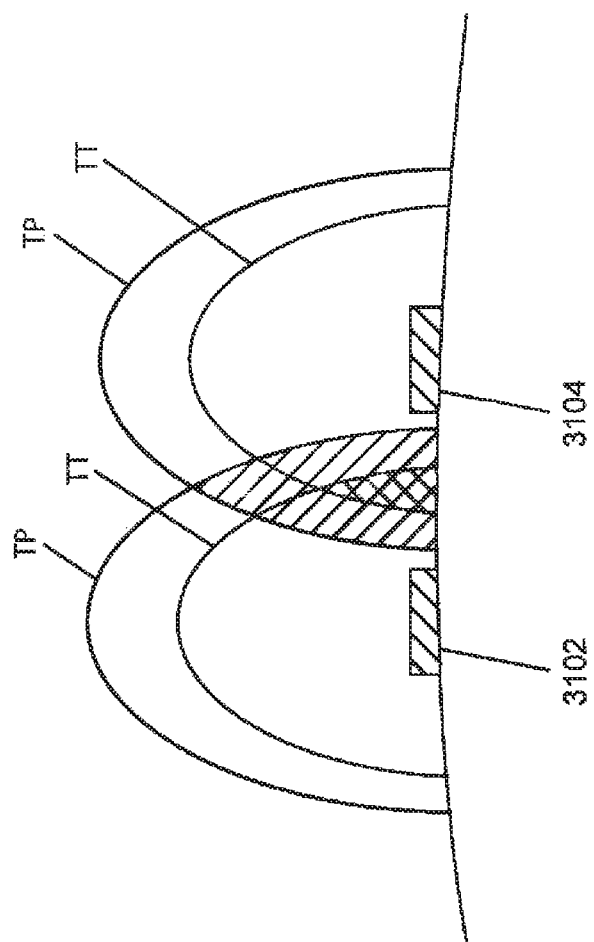

In other embodiments, however, the energy applied by the electrode assemblies, such as the electrode assemblies shown in FIG. 1C, may overlap, longitudinally, circumferentially, and/or in other ways, to at least some extent. FIGS. 31 and 32 schematically illustrate non-limiting examples of how electrodes 3102 and 3104 may be energized to create overlapping treatment zones. Although not shown specifically in FIGS. 31 and 32, electrodes 3102 and 3104 may each be a bipolar electrode pair (or may be single monopolar electrodes), and may be positioned on an outer surface of a catheter balloon or other expandable device such that they are longitudinally and circumferentially offset from one another (e.g. as in FIG. 1C). As shown in FIG. 31, each of electrodes 3102 and 3104 may be associated with a treatment zone (or may be configured to create such a treatment zone in a tissue in apposition with the electrodes) that includes a target temperature zone (the outer boundary of which is labeled "TT") and a thermal plume (the outer boundary of which is labeled "TP"). In some embodiments, the target temperature zone represents a region of the tissue that is at or above a desired target treatment temperature, or is within a desired target temperature range. In some embodiments, the thermal plume represents a region of tissue that is not necessarily at a target temperature or within a target temperature range, but exhibits an increase in temperature relative to an untreated zone outside of the thermal plume.

Whether or not treatment zones between electrodes/electrode pairs will overlap may be influenced by a wide variety of factors, including, but not limited to, electrode geometry, electrode placement density, electrode positioning, ground/common electrode(s) placement and geometry (in monopolar embodiments), energy generator output settings, output voltage, output power, duty cycle, output frequency, tissue characteristics, tissue type, etc.

In some embodiments, individual electrodes of a bipolar electrode pair may each define its own treatment zone, and such treatment zones may partially or entirely overlap.

In FIG. 31, the thermal plumes of the treatment zones overlap, although the target temperature zones do not. In FIG. 32, both the target temperature zones and the thermal plumes overlap. In some embodiments, the overlap of treatment zones may extend substantially continuously around a circumference of the device and/or around a circumference in a tissue surrounding a body passageway. In other embodiments, there may be overlap in treatment zones, however, that overlap will not be substantially continuous around a circumference and significant discontinuities in the treatment zones may be present.

Figure 33:
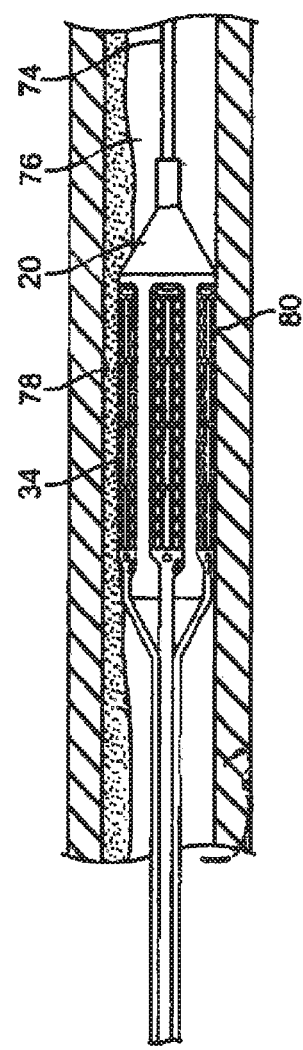
FIG. 33 shows an expandable balloon including an electrode array positioned in a body passageway.

It has been experimentally determined that at least some electrosurgical systems utilizing an array of balloon-mounted electrodes can create overlapping treatment zones between adjacent electrode pads, and, in at least some instances, create treatment zones that are effectively substantially continuous about a circumference of a body passageway. In one experiment, a catheter and expandable balloon similar to that shown and described in U.S. Pub. No. 2008/0188912 (incorporated in its entirety by this reference), particularly at FIG. 9C (reproduced here as FIG. 33), was used to generate overlapping treatment zones between adjacent electrode pairs, such that a treatment zone effectively extended substantially continuously about a circumference. As shown in FIG. 33, the catheter is advanced distally over guidewire 74 through a blood vessel 76. The expandable balloon 20 includes several longitudinally extending series of bipolar electrode pairs 34 positioned about the circumference of the balloon. Unlike the electrode arrays shown in, for instance, FIG. 1C, the electrode arrays shown in FIG. 33 are arranged symmetrically on the expandable balloon 20. Balloon 20 expands radially within the lumen if the blood vessel 76 so that electrodes 34 radially engage atherosclerotic material 78. As atherosclesrotic material 78 may be distributed eccentrically about catheter 12, some of electrodes 34 may engage both atherosclerotic material 78 and healthy tissue 80.

In one experiment utilizing a catheter-based balloon electrode array similar to that of FIG. 33, local response of fourteen renal vessels that were either treated with various power and duration of radio-frequency regimens (about 60° C. to about 75° C. for about 5 seconds to about 120 seconds), or left untreated, was evaluated on day 28±1 and day 84. Additionally, the kidneys from a total of 7 animals were evaluated via light microscopy.

Kidneys and renal arteries were explanted intact with underlying muscle and fixed in 10% neutral buffered formalin. Fixed tissues were then submitted for histopathological processing and evaluation. Each vessel was trimmed at approximately every 3-4 mm until the tissue was exhausted, processed, embedded in paraffin, sectioned twice at ~5 microns, and stained with hematoxylin and eosin (H+E) and elastin trichrome (ET). Kidneys were trimmed at three levels (cranial, center and caudal), processed, embedded in paraffin, sectioned and stained with H+E. All resulting slides were examined via light microscopy.

Figure 34:
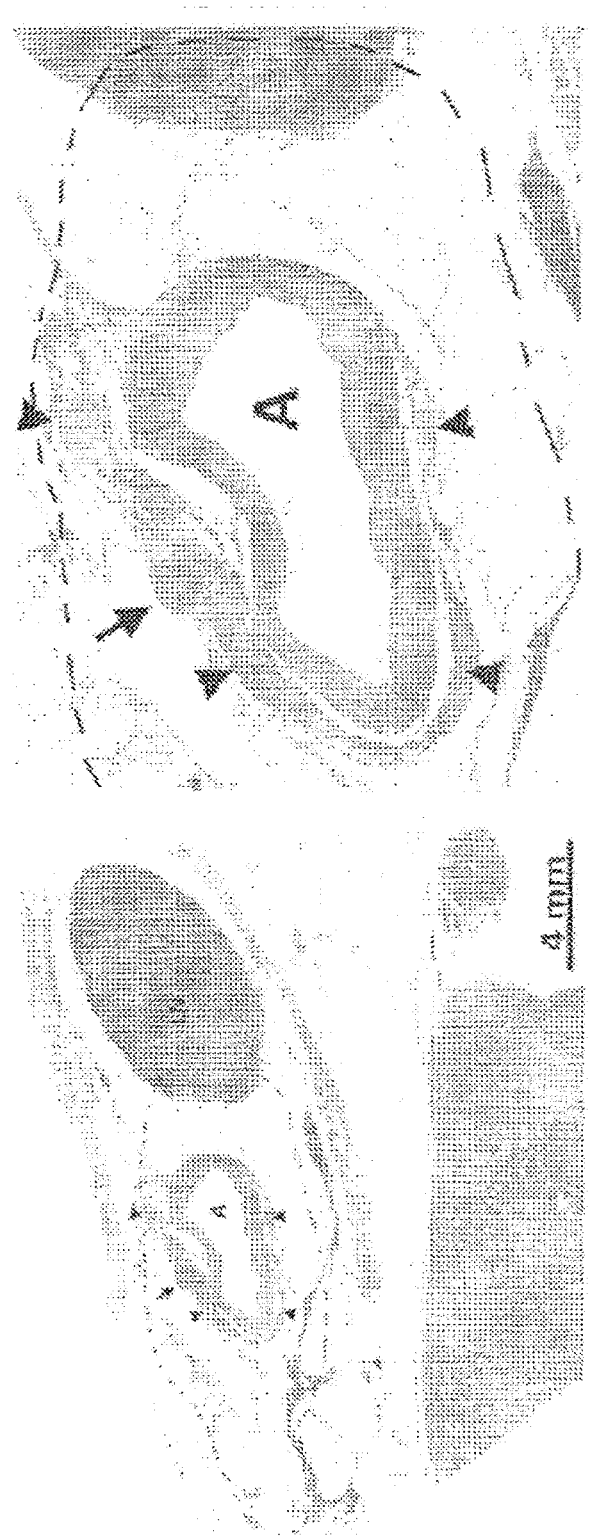
FIGS. 34-38 illustrate an experiment assessing, among other things, the extent of treatment zones created by electro-surgical procedures in tissues proximate renal arteries.
Figure 35:

Evaluation of step sections from six acute arteries treated at various power and duration of radio-frequency regimens or left untreated, and evaluation of dependent kidneys showed acute thermal changes characterized by coagulation necrosis in the media and perivascular tissues and collagen hyalinization. FIG. 34 shows a cross section of a left renal artery (labeled A) and surrounding tissue treated with six pairs of electrodes in a 75° C. protocol for ten seconds. In FIG. 34, circumferential thermal injury was observed within the boundaries of the dotted line, including injury to several nerve branches (as indicated by the arrowheads), a ganglion (short arrow) and a portion of the adjacent lymph node (LN). FIG. 35 shows a cross section of a right renal artery and surrounding tissue treated with six pairs of electrodes in a 75° C. protocol for five seconds. In FIG. 35, circumferential injury was observed within the boundaries of the dotted line and includes several nerve branches (as indicated by the arrowheads). Referring to FIGS. 34 and 35, thermal injury was circumferential in the central-most segment treated in the left artery and in the media of the right artery. The kidneys showed no treatment-related changes. Circumferential treatment was effective at reaching and creating injury in extrinsic renal innervation with a radial reach that was up to 10 mm in depth. There was minimal to notable procedural injury caused by balloon treatment of a magnitude likely to trigger a significant restenotic response.

Figure 36:
Figure 37:
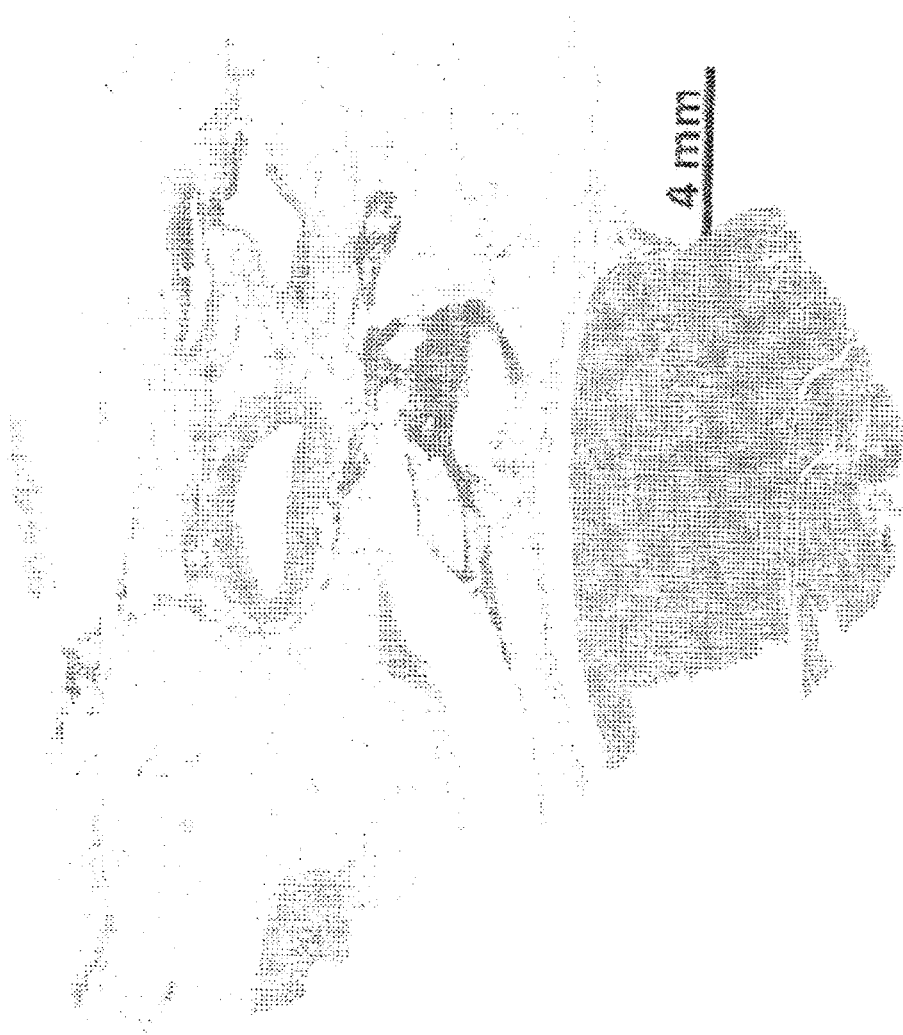
Figure 38:
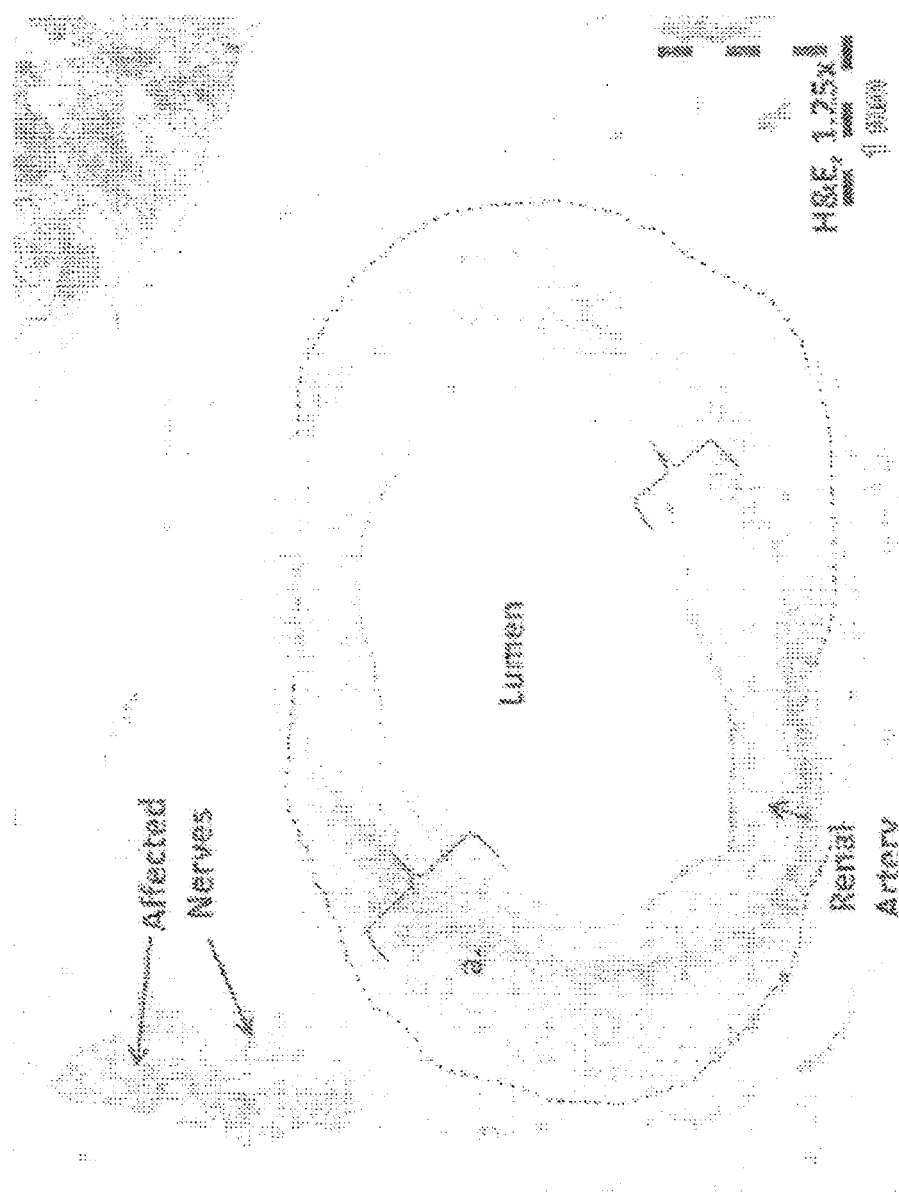

FIGS. 36 and 37 show additional cross sections of the left renal artery of FIG. 34, at day 27 post treatment. FIG. 38 is another representative low magnification image of a 75° C. RF treatment. The zones of treatment in FIG. 38 are evidenced by residual necrotic tunica media and adventitial thickening by early smooth muscle cell hyperplasia, fibroplasia, and inflammatory infiltrates (e.g., brackets). FIG. 38 also shows extension of the zone of treatment into the adjacent adventitia (as shown by the dashed lines).

Figure 41:
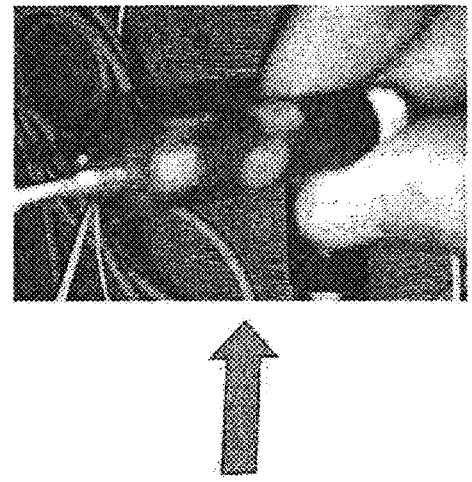
FIGS. 39-41 illustrate an example of overlapping treatment zones during the course of an RF treatment.
Figure 40:
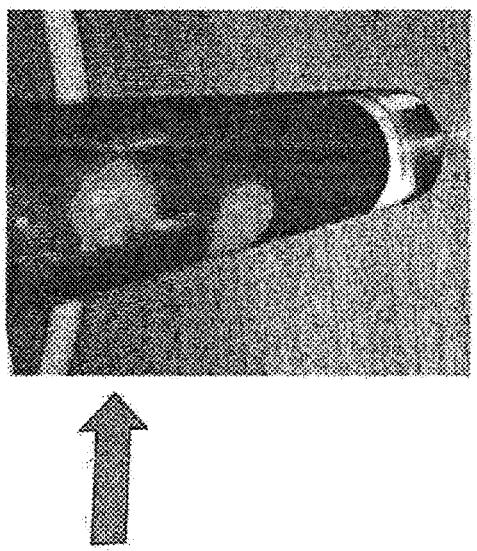
Figure 39:
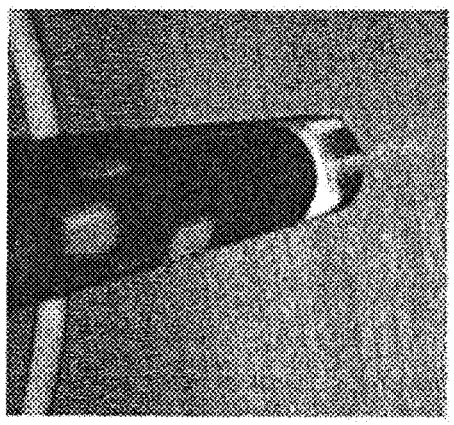

FIGS. 39-41 further illustrates how, in some embodiments, treatment zones can overlap over the course of an RF energy treatment. FIGS. 39-41 illustrate a Vessix V2 catheter positioned in a cylinder filled with a thermo-sensitive gel over the course of a thirty second treatment. FIG. 39 shows the thermo-sensitive gel just after treatment initiation, with the square shaped patches in the gel indicating localized electrode heating. As shown in FIG. 40, as the treatment progresses, the patches in the gel increase in size due to heat conduction and come close to touching. FIG. 41 shows the gel at the completion of a 30 second treatment, showing substantial overlap in the patches.

b. Electrode Assembly Structure

Returning to FIG. 1C, each electrode pad assembly includes four major elements, which are a distal electrode pad 150a-d, intermediate tail 160a-d, proximal electrode pad 170a-d, and proximal tail 180b-d (not shown for electrode pad assemblies 140a and 140c). Constructional details of the electrode assemblies 140a-d are shown and described with reference to FIGS. 2A-C.

Figure 2A:
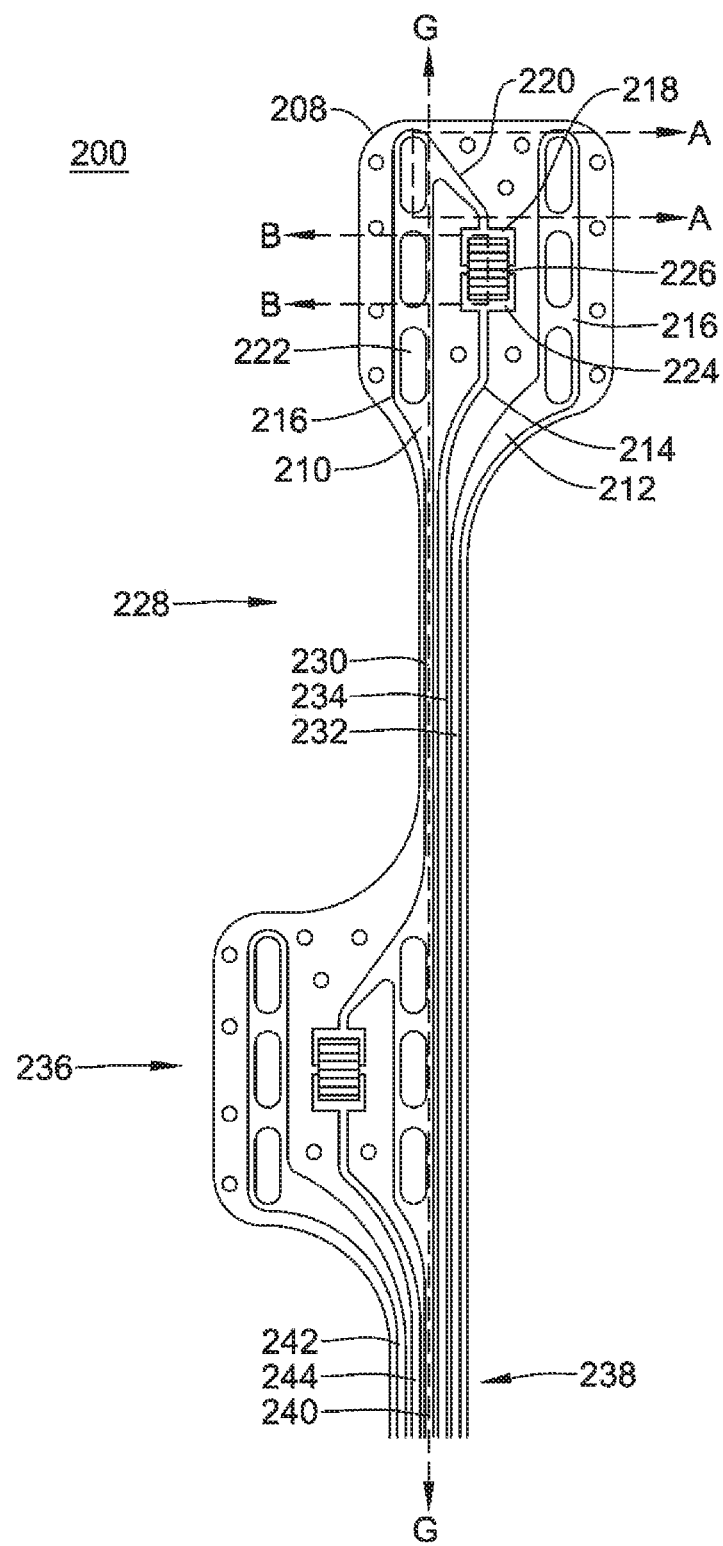
FIG. 2A is a top view of an example electrode assembly.

FIG. 2A shows a top view of electrode assembly 200, which is identified in FIG. 1C as electrode assembly 140. The electrode assembly 200 is constructed as a flexible circuit having a plurality of layers. Such layers can be continuous or non-contiguous, i.e., made up of discrete portions. Shown in FIGS. 2B and 2C, a base layer 202 of insulation provides a foundation for the electrode assembly 200. The base layer 202 can be constructed from a flexible polymer such as polyimide. In some embodiments, the base layer 202 is approximately 0.5 mil (0.0127 mm) thick. A conductive layer 204 made up of a plurality of discrete traces is layered on top of the base layer 202. The conductive layer 204 can be, for example, a layer of electrodeposited copper. In some embodiments, the conductive layer 204 is approximately 0.018 mm thick. An insulating layer 206 is discretely or continuously layered on top of the conductive layer 204, such that the conductive layer 204 is fluidly sealed between the base layer 202 and the insulating layer 206. Like the base layer 202, the insulating layer 206 can be constructed from a flexible polymer such as polyimide. In some embodiments, the insulating layer 206 is approximately 0.5 mil (0.0127 mm) thick. In other embodiments, the insulating layer 206 is a complete or partial polymer coating, such as PTFE or silicone.

The electrode assembly 200 shown in FIG. 2A includes a distal electrode pad 208. In this region, the base layer 202 forms a rectangular shape. As shown, the electrode assembly 200 may include a plurality of openings to provide for added flexibility, and the pads and other portions of the assemblies may include rounded or curved corners, transitions and other portions. In some instances, the openings and rounded/curved features may enhance the assembly's resistance to delamination from its expandable device, as may occur, in some instances, when the expandable device is repeatedly expanded and collapsed (which may also entail deployment from and withdrawal into a protective sheath), such as may be needed when multiple sites are treated during a procedure.

The distal electrode pad 208 includes a plurality of discrete traces layered on top of the base layer 202. These traces include a ground trace 210, an active electrode trace 212, and a sensor trace 214. The ground trace 210 includes an elongated electrode support 216 laterally offset from a sensor ground pad 218. The sensor ground pad 218 is electrically coupled to the elongated support 216 of the ground trace 210 and is centrally located on the distal electrode pad 208. A bridge 220 connects a distal most portion of the sensor ground pad 218 to a distal portion of the elongated electrode support 216 of the ground trace 210. The bridge 220 tapers down in width as it travels to the sensor ground pad 218. In some embodiments, the bridge 220 has a relatively uniform and thin width to enable a desired amount of flexibility. The elongated electrode support 216 tapers down in width at its proximal end, however, this is not required. In some embodiments, the elongated electrode support 216 can abruptly transition to a much thinner trace at its proximal portion, to enable a desired amount of flexibility. Generally, the curvature of the traces where necking is shown is optimized to reduce balloon recapture forces and the potential for any snagging that sharper contours may present. The shape and position of the traces are also optimized to provide dimensional stability to the electrode assembly 200 as a whole, so as to prevent distortion during deployment and use.

The ground trace 210 and active electrode trace 212 of FIG. 2A share a similar construction. The active electrode trace 212 also includes an elongated electrode support 216.

Figure 2B:
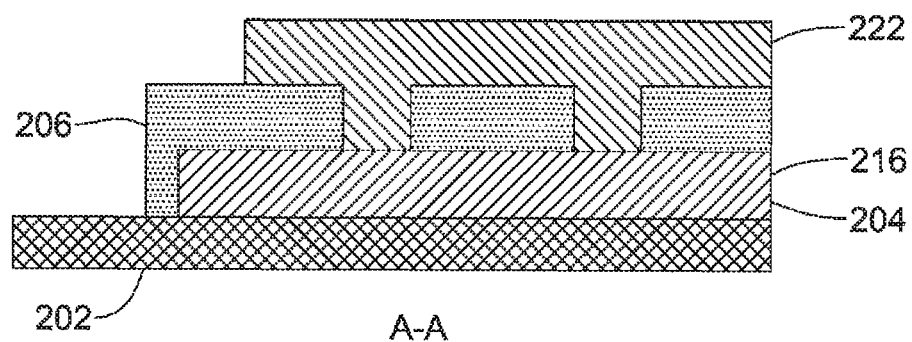
FIG. 2B is partial cross-sectional view A-A of FIG. 2A.
Figure 2C:
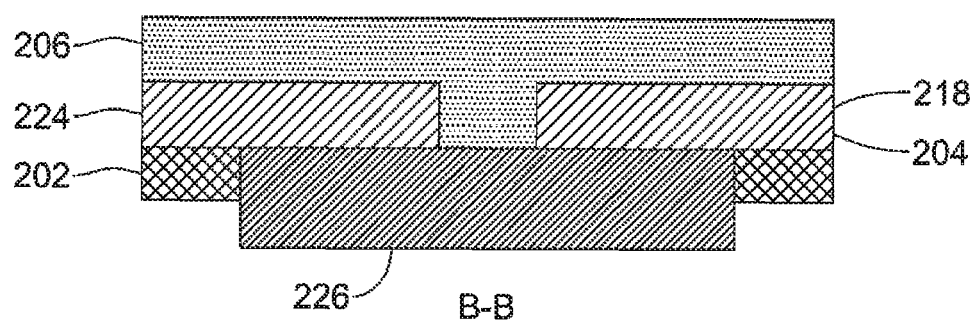
FIG. 2C is partial cross-sectional view B-B of FIG. 2A.

FIG. 2B shows a partial cross-section A-A of the distal electrode pad 208. An electrode 222 is shown layered over a portion of the insulating layer 206, which has a plurality of passages (e.g., holes) to enable the electrode 222 to couple to the elongated electrode support 216 of the ground trace 210 (of conductive layer 204).

As shown in FIG. 2A, the ground electrode trace 210 and active electrode trace 212 can include a plurality of electrodes. Three electrodes 222 are provided for each electrode trace, however, more or less can be used. Additionally, each electrode 222 can have radiused corners to reduce tendency to snag on other devices and/or tissue. Although the above description of the electrodes 222 and the traces associated with them has been described in the context of a bi-polar electrode assembly, those of skill in the art will recognize that the same electrode assembly may function in a monopolar mode as well. For instance, as one non-limiting example, the electrodes associated with active electrode traces 212 and 242 may be used as monopolar electrodes, with ground trace 210 disconnected during energization of those electrodes.

It has been experimentally determined that an example embodiment for a renal hypertension indication having an approximate longitudinal length of 4 mm per plurality of electrodes, including longitudinal spacing between electrodes 222, provides effective tissue remodeling results with respect to optimal lesion size and depth, while avoiding a stenoic response. The shown configuration was arrived at by balancing depth of thermal penetration, and avoidance of thermal damage to tissue collateral the treatment zone, while seeking to minimize the number of electrode pairs to optimize flexibility and profile on a final device However, the shown configuration is not a necessary requirement, since electrode size and placement geometry can vary according to desired therapeutic effect.

Thirty-three Yorkshire swine were subjected to renal denervation (RDN) by Vessix Vascular's renal denervation radiofrequency (RF) balloon catheters. Putative renal denervation through Vessix Vascular's electrode design was accomplished through a spectrum of settings (a function of electrode length, temperature, and duration) to compare the safety at 7 days and 28 days post-procedure between Vessix 16 mm circumferential electrodes vs. 2 mm and 4 mm electrode with offset design. Histologic sections of the renal arteries were examined to evaluate the tissue response including, but not limited to: injury, inflammation, fibrosis, and mineralization at 7 and 28 days.

The treatment of renal arteries with the Vessix Vascular RDN RF Balloon Catheter resulted in a spectrum of changes in the arterial wall and adjacent adventitia, which represented the progression of the arterial/adventitial response from an acute, "injurious" phase to a chronic, "reactive/reparative" phase. Treated areas within the renal arteries were apparent due to the presence of these changes in the arterial wall and extension thereof into the adjacent adventitial tissue (interpreted as the "zone of treatment").

At Day 7, all electrodes, regardless of length, treatment temperature or duration were associated with a primarily injurious response. However, the 2 mm and 4 mm electrodes were also associated with an early reactive/reparative response, regardless of treatment duration, which was not observed with either 16 mm RF treatment at Day 7. The overall extent of arterial circumference affected with the 16 mm electrodes was increased (mild/moderate to marked, ~>75% to 100% of circumference covered, respectively), regardless of temperature, relative to the shorter electrodes (2 mm and 4 mm) in which the affect was typically minimal to mild/moderate (~<25% to ~25-75% circumference affected, respectively), regardless of duration of treatment.

At Day 28, frequent, minimal neointima formation was observed, regardless of time point, in all treatment groups with the exception of the shorter 4 mm electrode. Mild/moderate neointima formation was infrequently observed only at Day 28, regardless of treatment group; however, the 16 mm electrodes were associated with a mild and comparable increase in the incidences of mild/moderate neointima relative to the shorter 2 and 4 mm electrode.

The denudation (i.e., loss) of endothelial cells is a common sequelae to the passage of any interventional device as well as an expected sequelae to the treatment with the Vessix Vascular RDN RF Balloon Catheter. Due to the importance of the endothelium in preventing thrombus formation, its recovery in denuded regions was monitored. As such, the magnitude/extent of the re-endothelialization of the luminal surface was interpreted relative to the approximate circumference of the artery affected At Day 7, the 2 and 4 mm electrodes had more arterial sections with complete endothelialization than not; complete endothelialization was present in all arterial sections of the 2 and 4 mm electrode. No arterial section treated with a 16 mm electrode was observed to have complete endothelialization at Day 7, regardless of dose.

At Day 7, inflammation was overall typically minimal, regardless of treatment; however, both 16 mm electrodes, regardless of dose, had an overall increase in inflammation relative to 2 and 4 mm electrodes. Mild/moderate inflammatory infiltrates were rarely observed in the 2 and 4 mm electrode, but were frequent to common in the 16 mm electrodes.

In the embodiment of FIG. 2A, each electrode 222 is approximately 1.14 mm by 0.38 mm, with approximately 0.31 mm gaps lying between the electrodes 222. The electrodes 222 of the ground trace 210 and active electrode trace 212 are laterally spaced by approximately 1.85 mm. In some embodiments, such as the embodiment shown in FIG. 2B, the electrodes 222 are gold pads approximately 0.038 mm thick from the conductive layer 204 and that protrude 0.025 mm above the insulating layer 206. Without limiting the use of other such suitable materials, gold is a good electrode material because it is very biocompatible, radiopaque, and electrically and thermally conductive. In other embodiments, the electrode thickness of the conductive layer 204 can range from about 0.030 mm to about 0.051 mm. At such thicknesses, relative stiffness of the electrodes 222, as compared to, for example, the copper conductive layer 204, can be high. Because of this, using a plurality of electrodes, as opposed to a single electrode, can increase flexibility. In other embodiments, the electrodes may be as small as 0.5 mm by 0.2 mm or as large as 2.2 mm by 0.6 mm for electrode 222.

While it is an important design optimization consideration to balance the thickness of the gold above the insulating layer 206 so as to achieve good flexibility while maintaining sufficient height so as to provide good tissue contact, this is counterbalanced with the goal of avoiding a surface height that may snag during deployment or collapse of the balloon. These issues vary according to other elements of a particular procedure, such as balloon pressure. For many embodiments, it has been determined that electrodes that protrude approximately 0.025 mm above the insulating layer 206 will have good tissue contact at balloon inflation pressures below 10 atm and as low as 2 atm. These pressures are well below the typical inflation pressure of an angioplasty balloon.

The sensor trace 214 is centrally located on the distal electrode pad 208 and includes a sensor power pad 224 facing the sensor ground pad 218. These pads can connect to power and ground poles of a heat sensing device 226, such as a thermocouple (for example, Type T configuration: Copper/Constantan) or thermistor, as shown in the partial cross-section depicted in FIG. 2C.

The heat sensing device 226 is proximately connected to the sensor power pad 224 and distally connected to the sensor ground pad 218. To help reduce overall thickness, the heat sensing device 226 is positioned within an opening within the base layer 202. In some embodiments, the heat sensing device 226 is a thermistor having a thickness of 0.1 mm, which is unusually thin—approximately two-thirds of industry standard. As shown, the heat sensing device 226 is on a non-tissue contacting side of the distal electrode pad 208. Accordingly, the heat sensing device 226 is captured between the electrode structure and a balloon when incorporated into a final device, such as catheter 120. This is advantageous since surface-mounted electrical components, like thermistors, typically have sharp edges and corners, which can get caught on tissue and possibly cause problems in balloon deployment and/or retraction. This arrangement also keeps soldered connections from making contact with blood, since solder is typically non-biocompatible. Further, due to the placement of the heat sensing device, it can measure temperature representative of tissue and the electrodes 222. Designs in the prior art typically take one of two approaches—either contacting tissue or contacting the electrode. Here, neither of these prior approaches are employed.

From the rectangular distal electrode pad 208, the combined base layer 202, conductive layer 204, and insulating layer 206 reduce in lateral width to an intermediate tail 228. Here, the conductive layer 204 is formed to include an intermediate ground line 230, intermediate active electrode line 232, and intermediate sensor line 234, which are respectively coextensive traces of the ground trace 210, active electrode trace 212, and sensor trace 214 of the distal electrode pad 208.

From the intermediate tail 228, the combined base layer 202, conductive layer 204, and insulating layer 206 increase in lateral width to form a proximal electrode pad 236. The proximal electrode pad 236 is constructed similarly to the distal electrode pad 208, with the electrode geometry and heat sensing device arrangement being essentially identical, although various differences may be present. However, as shown, the proximal electrode pad 236 is laterally offset from the distal electrode pad 208 with respect to a central axis G-G extending along the intermediate ground line 230. The intermediate active electrode line 232 and intermediate sensor line 234 are laterally coextensive with the proximal electrode pad 236 on parallel respective axes with respect to central axis G-G.

From the proximal electrode pad 236, the combined base layer 202, conductive layer 204, and insulating layer 206 reduce in lateral width to form a proximal tail 238. The proximal tail 238 includes a proximal ground line 240, proximal active electrode line 242, and proximal sensor line 244, as well the intermediate active electrode line 232 and intermediate sensor line 234. The proximal tail 238 includes connectors (not shown) to enable coupling to one or more sub-wiring harnesses and/or connectors and ultimately to control unit 110. Each of these lines are extended along parallel respective axes with respect to central axis G-G.

As shown, the electrode assembly 200 has an asymmetric arrangement of the distal electrode pad 208 and proximal electrode pad 236, about axis G-G. Further, the ground electrodes of both electrode pads are substantially aligned along axis G-G, along with the intermediate and proximal ground lines 230/240. It has been found that this arrangement presents many advantages. For example, by essentially sharing the same ground trace, the width of the proximal tail is only about one and a half times that of the intermediate tail 228, rather than being approximately twice as wide if each electrode pad had independent ground lines. Thus, the proximal tail 238 is narrower than two of the intermediate tails 228.

Further, arranging the electrode pads to share a ground trace allows control of which electrodes will interact with each other. This is not immediately apparent when viewing a single electrode assembly, but becomes evident when more than one electrode assembly 200 is assembled onto a balloon, for example as shown in FIG. 1C. The various electrode pads can be fired and controlled using solid state relays and multiplexing with a firing time ranging from about 100 microseconds to about 200 milliseconds or about 10 milliseconds to about 50 milliseconds. For practical purposes, the electrode pads appear to be simultaneously firing yet stray current between adjacent electrode pads of different electrode assemblies 200 is prevented by rapid firing of electrodes in micro bursts. This can be performed such that adjacent electrode pads of different electrode pad assemblies 200 are fired out of phase with one another. Thus, the electrode pad arrangement of the electrode assembly allows for short treatment times—10 minutes or less of total electrode firing time, with some approximate treatment times being as short as 10 seconds, with and exemplary embodiment being about 30 seconds. The benefits of short treatment times include minimization of post-operative pain caused when nerve tissue is subject to energy treatment, shortened vessel occlusion times, reduced occlusion side effects, and quick cooling of collateral tissues by blood perfusion due to relatively minor heat input to luminal tissue.

In some embodiments, the common ground typically carries 200 VAC at 500 kHz coming from the negative electrode pole, and a 1V signal from the heat sensing device 226 (in the case of a thermistor) that requires filtering of the RF circuit such that the thermistor signal can be sensed and used for generator control. In some embodiments, because of the common ground, the thermistor of the adjacent electrode pair may be used to monitor temperature even without firing the adjacent electrode pair. This provides the possibility of sensing temperatures proximate to both the distal electrode pad 208 and the proximal electrode pad 236, while firing only one of them.

Referring again to FIG. 1C, the electrode pad arrangement of each electrode assembly 140a-d also enables efficient placement on balloon 130. As shown, the electrode assemblies 140a-d "key" into one another to enable maximum use of balloon surface area. This is accomplished in part by spacing the electrode pads apart by setting the longitudinal length of each intermediate tail. For example, the intermediate tail length electrode assembly 140a is set to a distance that separates its distal and proximal electrode pads 150a, 170a such that the laterally adjacent proximal electrode pad 170b of the laterally adjacent electrode assembly 140b keys next to the intermediate tail 160a of electrode assembly 140a. Further, the distal electrode pad 150a of electrode assembly 140a is keyed between the intermediate tail 160b of electrode assembly 140b and the intermediate tail 160d of electrode assembly 140d. Thus, the length of each intermediate tail 160a-d also requires each electrode pad of any one electrode assembly to be located in non-adjacent treatment zones.

Balloon surface area maximization is also enabled in part by laterally offsetting both electrode pads of each electrode assembly 140a-d. For example, the rightwards lateral offset of each distal electrode pad 150a-d and the leftwards lateral offset of the proximal electrode pad 170a-d allow adjacent electrode pad assemblies to key into one another such that some of the electrode pads laterally overlap one another. For example, the distal electrode pad 150*a* of electrode assembly 140*a* laterally overlaps with proximal electrode pad 170*b* of electrode assembly 140*b*. Further, the distal electrode pad 150*b* of electrode assembly 140*b* laterally overlaps with the proximal electrode pad 170*c* of electrode assembly 140*c*. However, the length of each intermediate tail prevents circumferential overlap (longitudinal overlap in this view) of the electrode pads, thus maintaining the non-contiguous nature of the treatment zones in the longitudinal direction L-L.

The arrangement and geometry of the electrode pads, as well as the arrangement and geometry of the tails of the flexible circuits may also facilitate folding or otherwise collapsing the balloon into a relatively compact un-expanded state. For instance, in embodiments with an expanded diameter of up to 10 mm, the device in an un-expanded state may have as low as an approximately 1 mm diameter.

Some embodiments utilize a standard electrode assembly having identical dimensions and construction, wherein the number and relative position of electrode assemblies on an outer surface of a balloon becomes a function of balloon diameter and/or length while electrode assembly geometries remain unchanged amongst various balloon sizes. The relative positioning of electrode assemblies relative to balloon diameter and/or length may then be determined by the desired degree or avoidance of circumferential and/or axial overlap of adjacent electrode pads of neighboring electrode assemblies on a balloon of a given size. In other embodiments, however, all of the electrode assemblies on the balloon will not necessarily be identical.

Figure 3A:
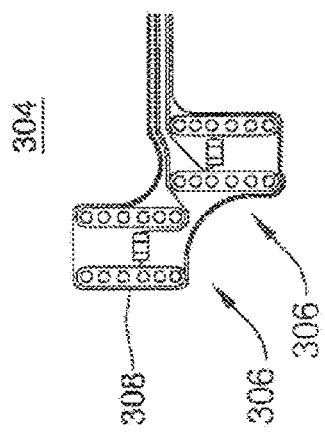
FIGS. 3A-3D are top views of various example electrode assemblies having multiple electrode pads.

FIGS. 3A-3D shows alternative electrode pad configurations useable with the system 100 of FIG. 1A. FIG. 3A shows an electrode assembly 300 that is constructed similarly to electrode assembly 200, but having two electrode pads 302 that are directly adjacent to one another.

Figure 3B:
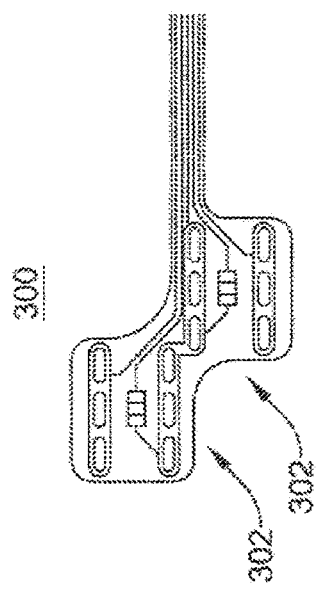

FIG. 3B shows an electrode pad assembly 304 that is constructed similarly to electrode assembly 200, but having two electrode pads 306 that are directly adjacent to one another. Further, the electrode pads 306 have electrodes arranged to be transverse with respect to longitudinal axis L-L of FIG. 1C and G-G of FIG. 2A.

Figure 3C:
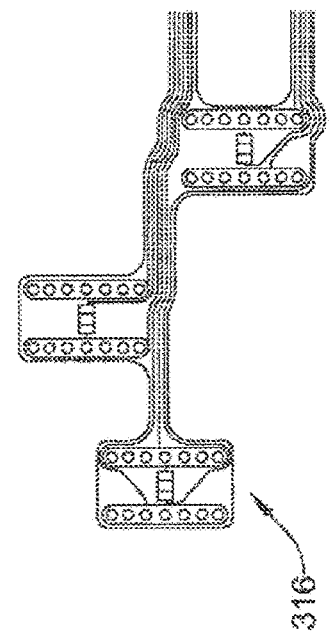

FIG. 3C shows an electrode assembly 310 that is constructed similarly to electrode assembly 304, but having three staggered and separated electrode pads 312. Like the electrode assembly 304 of FIG. 3B, the electrode pads 312 feature transversely arranged electrodes.

Figure 3D:
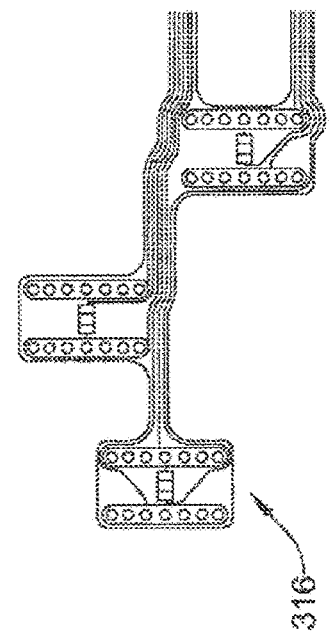

FIG. 3D shows an electrode assembly 314 that is constructed similarly to electrode assembly 310, but having electrode pads 312 with greater electrode surface area. Like the electrode assembly 304 of FIG. 3B, the electrode pads 316 feature transversely arranged electrodes.

FIGS. 4A-4C shows alternative electrode pad configurations useable with the system 100 of FIG. 1A. FIG. 4A shows an electrode assembly 400 that is constructed similarly to electrode assembly 200, but having only a single distal electrode pad 402.

FIG. 4B shows an electrode assembly 404 that is constructed similarly to electrode assembly 400, but having an single distal electrode pad 407 with a greater active electrode 408 surface area than ground surface area 410.

FIG. 4C shows an electrode assembly 412 that is constructed similarly to electrode assembly 404, but having a single distal electrode pad 414 having a heavily porous construction to enable greater flexibility.

Figure 5A:
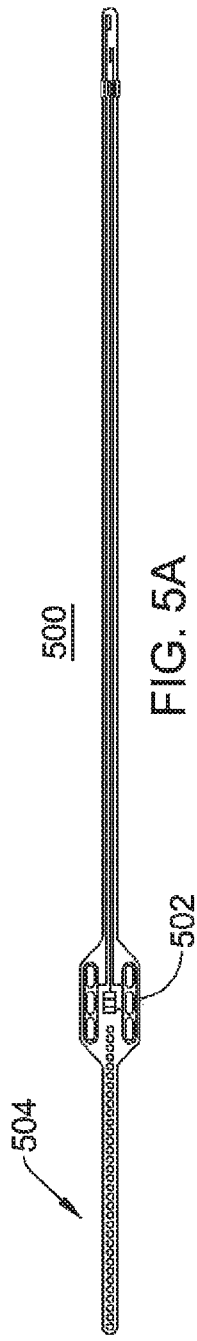

FIGS. 5A-5F shows alternative electrode configurations useable with the system 100 of FIG. 1A. In some embodiments, the shown electrode configurations are useable with the configurations of FIGS. 4A-4C. FIG. 5A shows an electrode assembly 500 that is constructed similarly to electrode assembly 400, but arranged to include only a single proximal electrode pad 502. The electrode assembly 500 further includes an elongated distal portion 504 for attachment to a balloon.

Figure 5B:
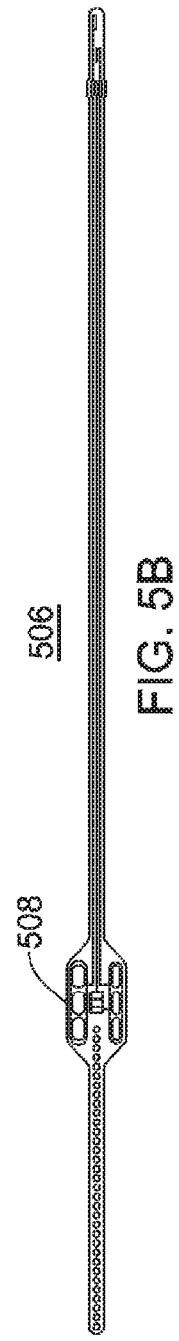

FIG. 5B shows an electrode assembly 506 that is constructed similarly to electrode assembly 500, but having more comparative electrode surface area on electrode pad 508.

Figure 5C:
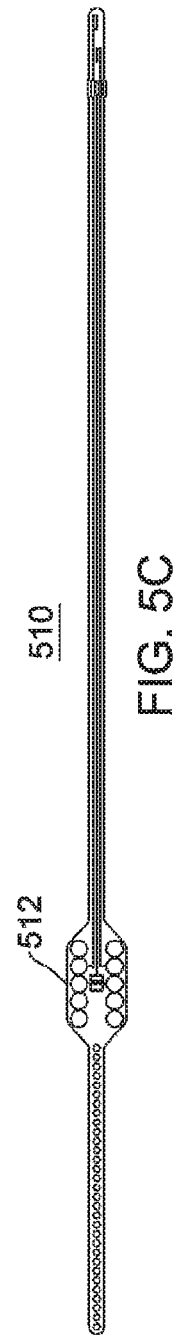

FIG. 5C shows an electrode assembly 510 that is constructed similarly to electrode assembly 500, but having more comparative electrode surface area on electrode pad 512 and a larger number of electrodes.

Figure 5D:
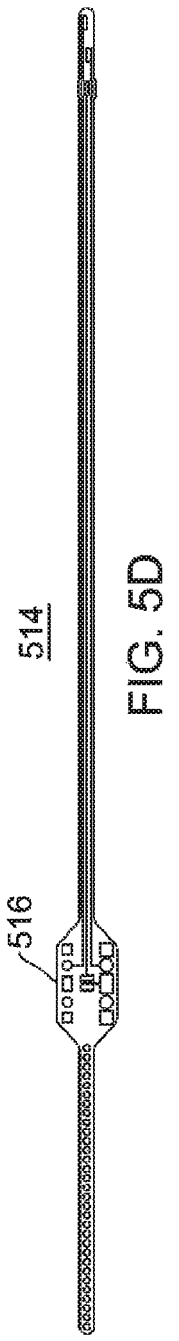

FIG. 5D shows an electrode assembly 514 that is constructed similarly to electrode assembly 510, but having a non-uniform electrode configuration on electrode pad 512.

FIG. 5E shows an electrode assembly 514 that is constructed similarly to electrode assembly 500, but having less comparative electrode surface area on electrode pad 516 and a smaller number of electrodes 518. Electrode pad 516 also incorporates two heat sensing devices 520 mounted on the same side as electrodes.

FIG. 5F shows an electrode assembly 522 that is constructed similarly to electrode assembly 514, but having a transversely arranged electrode 524 and a single heat sensing device 526.

The electrode assemblies of FIGS. 2 through 5F may be used in bipolar or monopolar configurations. FIGS. 5G through 5I illustrate additional examples of monopolar electrode configurations. In FIG. 5G there are two parallel arrays of monopolar electrodes 530 on either side of temperature sensor 532. In FIG. 5G, each array of monopolar electrodes 530 has its own discrete trace, with the temperature sensor 532 having its own discrete trace as well. In other embodiments, however, all of the monopolar electrodes 530 on a particular flex circuit assembly may share a single active trace, and one of the temperature sensor's two traces may be shared as well, although, in other embodiments, the power and ground traces for the temperature sensor may be separate from the monopolar trace(s).

FIG. 5H illustrates another arrangement for a monopolar electrode pad in which all of the monopolar electrodes 536 are coupled to a single trace. FIG. 5I shows another alternative arrangement for the monopolar electrodes and temperature sensor 538. The monopolar electrode pads may be arranged about an expandable device in longitudinally and circumferentially offset arrangements (such as shown in FIG. 1C) and may have geometries and arrangements similar to those shown in FIGS. 3A through 5F.

Treatment Methods and Control Systems a. Device Positioning

FIG. 6 shows the system 100 of FIG. 1A being used to perform a method 600 of treatment in accordance with one non-limiting embodiment of the disclosure. Here, control unit 110 is shown operationally coupled to catheter device, which has been placed in a body passageway such that an expandable device (having a plurality of electrode assemblies) is placed adjacent to a section S1 of the body passageway where therapy is required. Placement of the catheter device at section S1 can be performed according to conventional methods, e.g., over a guidewire under fluoroscopic guidance.

Once placed in S1, the expandable device can be made to expand, e.g., by pressurizing fluid from 2-10 atm in the case of a balloon. This causes electrodes of the expandable device to come into contact with the body passageway.

In some embodiments, control unit 110 may measure impedance at the electrode assemblies to confirm apposition of the electrodes with the body passageway. In at least some of these embodiments, the treatment may proceed even if apposition is not sensed for all of the electrodes. For instance, in some embodiments, the treatment may proceed if apposition is sensed for 50% or more of the electrodes, and may allow for less than complete uniformity of apposition circumferentially and/or axially. For example, in some instances the catheter may be positioned such that one or more of the proximal electrodes are in the aorta and exposed to blood, and impedance sensed for such electrodes may not fall within a pre-designated range (such as, for example, 500-1600 ohms), indicating an absence of tissue apposition for those electrodes. In some instances, the system may allow for user authorization to proceed with the treatment even if there is less than uniform electrode/tissue apposition. Subsequently, the control unit 110 may activate the electrodes to create a corresponding number of lesions L, as indicated by the black squares. During activation of the electrodes, the control unit uses heat sensing devices of the electrode pads to monitor both heat of the electrode and the tissue due to the unique arrangement of the heat sensing devices, which do not contact either tissue or electrodes. In this manner, more or less power can be supplied to each electrode pad as needed during treatment.

In some embodiments, control unit 110 may apply a uniform standard for determining apposition to all the electrodes of the device. For instance, the control unit may utilize the same pre-designated range of resistance measurements to all of the electrodes. In other instances, however, including some, although not all, monopolar applications, different standards may be applied to different monopolar electrodes for determining apposition. For example, in some monopolar embodiments, each monopolar electrode may define a discrete electrical circuit through the tissue to the common/indifferent electrode (or electrodes), and the characteristics of those circuits (e.g. resistance) may vary significantly based on the distance between the monopolar electrode and common electrode, the tissue characteristics therebetween, and other geometries and characteristics of the device and surrounding tissue. As such, in at least some embodiments, it may be desirable to apply criteria for determining apposition that varies depending on, e.g., the distance between the monopolar electrode and common electrode (e.g. the greater the distance between the two electrodes, the higher the impedance measurement required to determine good apposition). In other embodiments, however, the variance due to these differences in distance and other geometries will be minimal or non-substantive, and a uniform standard may be applied.

Figure 24A:
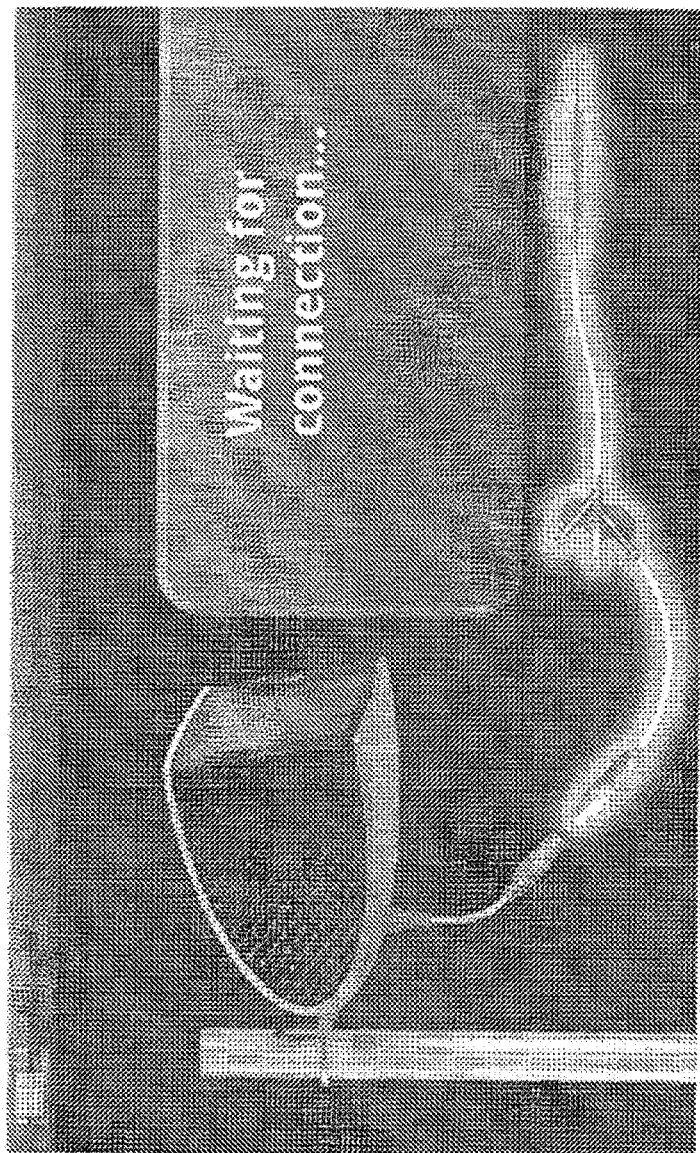
FIGS. 24A-24F are example screen shots from one embodiment of a treatment.
Figure 24B:
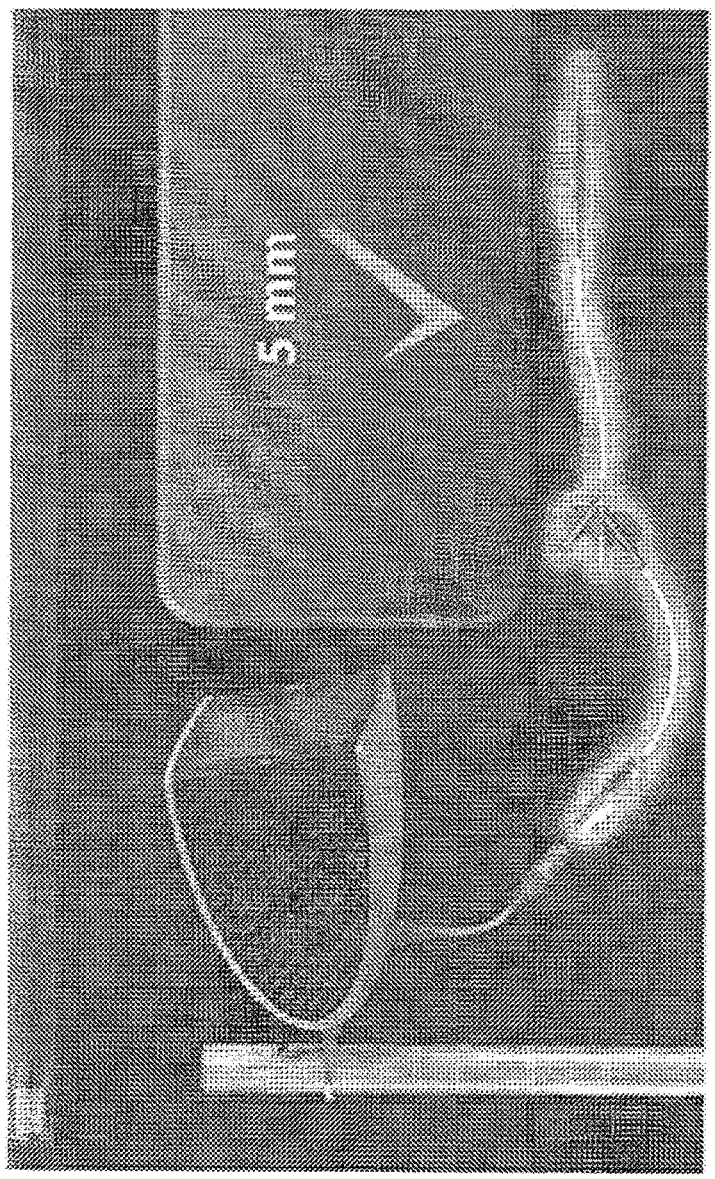
Figure 24C:
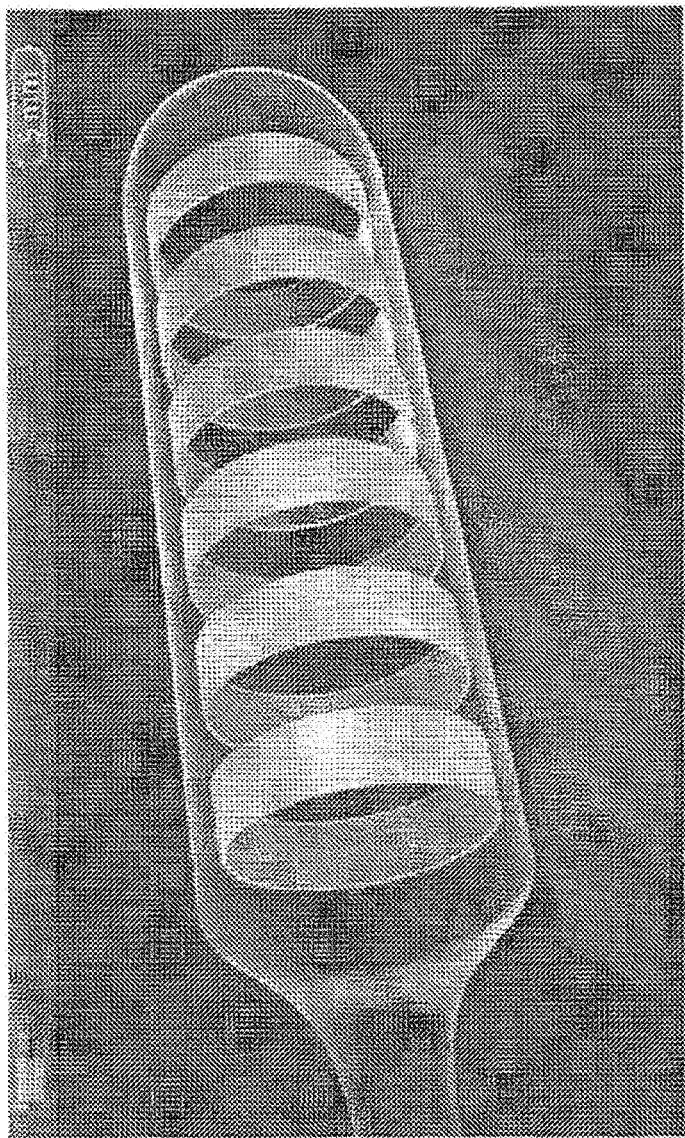
Figure 24D:
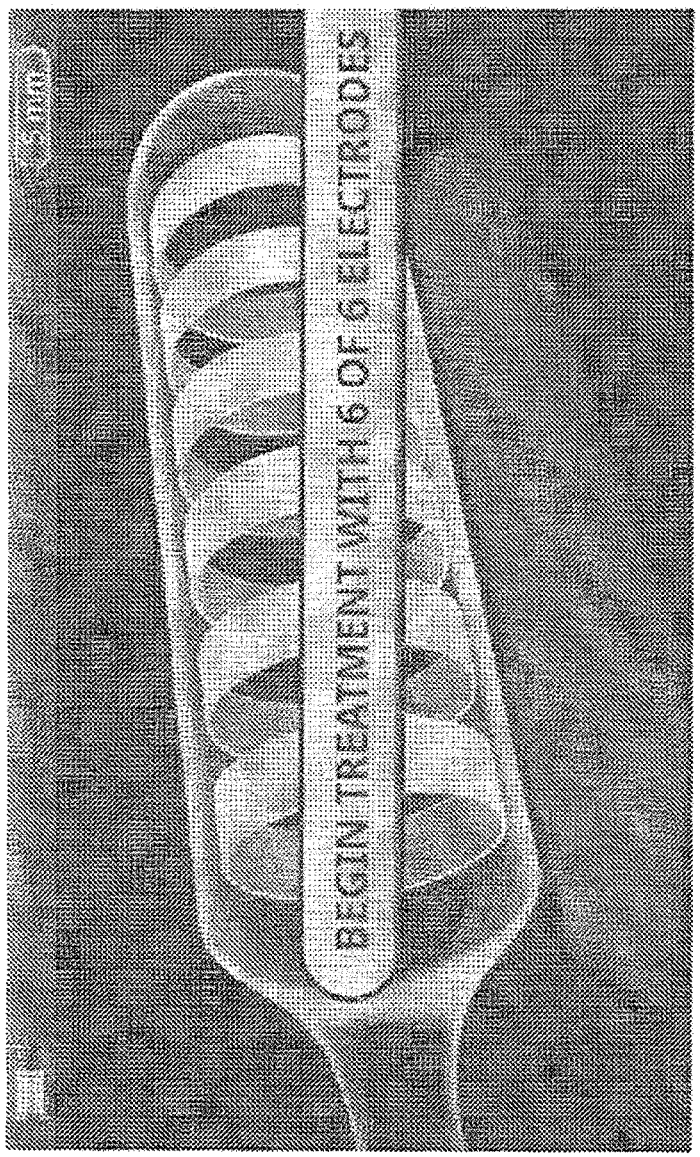
Figure 24E:
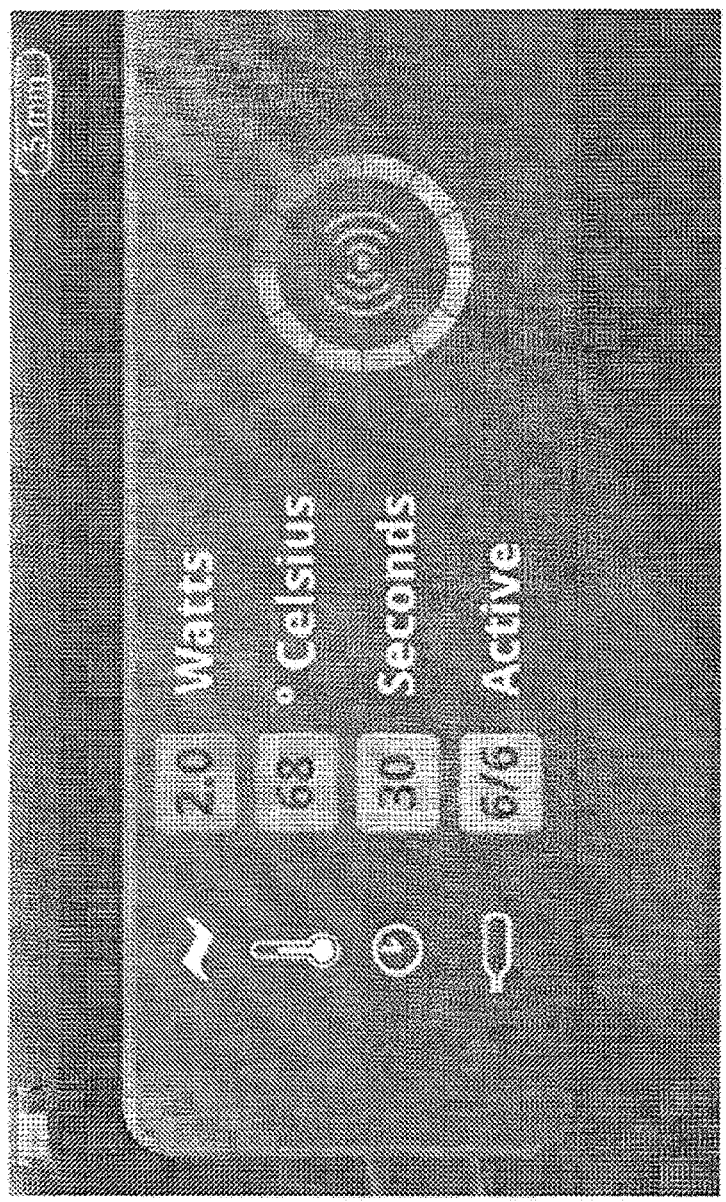
Figure 24F:
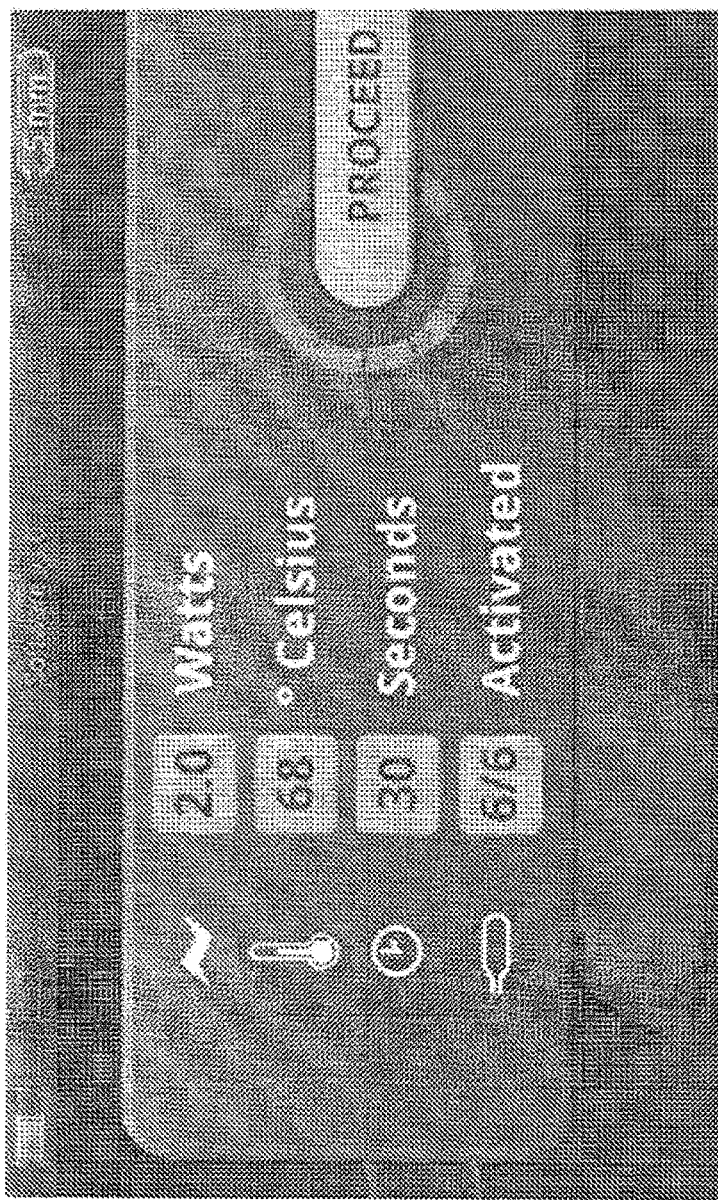

FIGS. 24A-F illustrate one non-limiting example of a series of screen shots displayed by the control unit during the course of a treatment. In FIG. 24A, the system prompts a user to connect a catheter. In FIG. 24B, the system confirms that a catheter has been connected and other information about the connected catheter (e.g. size/diameter). At FIGS. 24C and D, the system, as discussed above, can check for electrode apposition, indicate which or what number of electrodes are in apposition, and ask for authorization to proceed. In FIG. 24C, three electrodes (e.g., the first three or "proximal" electrodes) are shown as in apposition while in FIG. 24D all the electrodes are shown in apposition. In FIGS. 24E and F, the system may display certain parameters of the treatment, both during and after the treatment (e.g. power, temperature, time, and number of active/activated electrodes). Information about the treatment, such as the aforementioned parameters and/or other information, may be captured by the system and saved to memory.

Returning to FIG. 6, after the prescribed therapy in section S1 is complete, the expandable device may then be deflated and moved to an untreated section S2 to repeat the therapy applied in section S1, and similarly to section S3, and any more sections as needed. The sections are shown directly adjacent, but can be separated by some distance.

In some instances, alternative methods other than those illustrated in FIG. 6 will be utilized. For instance, in other embodiments, the treatment will be performed at only a single location in the passageway, and it will not be necessary to move the expandable device to multiple locations in the passageway.

Referring again to the example of renal hypertension involving the reduction of excessive nerve activity, the system may be used to effect a non-piercing, non-ablating way to direct energy to affect nerve activity. Accordingly the body passage shown can be a renal artery surrounded by nerve tissue N in sections S1-S3. Electrodes on the expandable device may be powered to deliver energy in the known direction of a nerve N to be affected, the depth of energy penetration being a function of energy dosage, electrode type (e.g. monopolar vs. bipolar) and electrode geometry. U.S. Pub. No. 2008/0188912 entitled "System for Inducing Desirable Temperature Effects on Body Tissue", the full disclosure of which is incorporated herein by reference, describes some considerations for electrode geometry and the volume of tissue treatment zones that may be taken into account in some, although not necessarily all, embodiments. In some instances, empirical analysis may be used to determine the impedance characteristics of nervous tissue N such that catheter device may be used to first characterize and then treat tissue in a targeted manner as disclosed and described herein. The delivery and regulation of energy may further involve accumulated damage modeling as well.

As shown, each lesion L is created in a corresponding treatment zone A-D of the expandable device 130. Accordingly, any lesion L made in one particular treatment A-D zone will not circumferentially overlap with a lesion of an adjacent treatment zone A-D at any point along the operational axis O-O. In some embodiments, a treatment zone of the expandable device 130 can have more than one electrode pad, and thus in such cases, lesions L created by those electrode pads can circumferentially overlap. In those cases, more lesions L may be required for a particular anatomy or a pair of electrode pads are required for performing a diagnostic routine before therapy is applied. Regardless, circumferential overlap of electrodes of adjacent treatment zones will not be present.

b. Energy Delivery

Depending on the particular remodeling effect required, the control unit may energize the electrodes with about 0.25 to 5 Watts average power for 1 to 180 seconds, or with about 0.25 to 900 Joules. Higher energy treatments may be done at lower powers and longer durations, such as 0.5 Watts for 90 seconds or 0.25 Watts for 180 seconds. In monopolar embodiments, the control unit may energize the electrodes with up to 30 Watts for up to 5 minutes, depending on electrode configuration and distance between the electrodes and the common ground. A shorter distance may provide for lower energy for a shorter period of time because energy travels over more localized area with fewer conductive losses. In an example embodiment for use in renal denervation, energy is delivered for about 30 seconds at a treatment setting of about 5 Watts, such that treatment zones are heated to about 68° C. during treatment. As stated above, power requirements may depend heavily on electrode type and configuration. Generally, with wider electrode spacing, more power is required, in which case the average power could be higher than 5 Watts, and the total energy could exceed 45 Joules. Likewise, using a shorter or smaller electrode pair would require scaling the average power down, and the total energy could be less than 4 Joules. The power and duration may be, in some instances, calibrated to be less than enough to cause severe damage, and particularly less than enough to ablate diseased tissue within a blood vessel. The mechanisms of ablating atherosclerotic material within a blood vessel have been well described, including by Slager et al. in an article entitled, "Vaporization of Atherosclerotic Plaque by Spark Erosion" in J. of Amer. Cardiol. (June, 1985), on pp. 1382-6; and by Stephen M. Fry in "Thermal and Disruptive Angioplasty: a Physician's Guide"; Strategic Business Development, Inc., (1990), the full disclosure of which is incorporated herein by reference.

In some embodiments, energy treatments applied to one or both of the patient's renal arteries may be applied at higher levels than would be possible in other passageways of the body without deleterious effects. For instance, peripheral and coronary arteries of the body may be susceptible to a deleterious long-term occlusive response if subjected to heating above a certain thermal response limit. It has been discovered that renal arteries, however, can be subjected to heating above such a thermal response limit without deleterious effect.

In some embodiments, energy treatments may be applied to one or both of the patient's renal arteries to affect sympathetic nerve activity in the kidneys in order to moderate both systolic and diastolic forms of CHF. The application of therapeutic thermal energy to the tissues proximate the renal artery may be effective in reducing the sympathetic nerve activity so as to mitigate the biological processes and the resulting effects of CHF. In some embodiments, a mild application of a controlled dose of thermal energy in a rapid procedure (e.g. 10 minutes or less of therapy time per kidney) is used so as to provide a simple procedure for the clinical staff while providing a procedure that minimizes the pain felt by a patient while maximizing the efficacy of the procedure. The balloon-mounted electrodes and energy delivery methods of the present disclosure may be particularly well suited for the application of energy to reduce sympathetic nerve activity related to chronic hypertension, in conjunction with or separate from, systolic and diastolic CHF.

In some embodiments, the electrode pads described herein may be energized to assess and then selectively treat targeted tissue to achieve a desired therapeutic result by a remodeling of the treated tissue. For example, tissue signature may be used to identify tissue treatment regions with the use of impedance measurements. Impedance measurements utilizing circumferentially spaced electrodes within a body passage may be used to analyze tissue. Impedance measurements between pairs of adjacent electrodes may differ when the current path passes through diseased tissue, and when it passes through healthy tissues of a luminal wall for example. Hence, impedance measurements between the electrodes on either side of diseased tissue may indicate a lesion or other type of targeted tissue, while measurements between other pairs of adjacent electrodes may indicate healthy tissue. Other characterization, such as intravascular ultrasound, optical coherence tomography, or the like, may be used to identify regions to be treated either in conjunction with, or as an alternate to, impedance measurements. In some instances, it may be desirable to obtain baseline measurements of the tissues to be treated to help differentiate adjacent tissues, as the tissue signatures and/or signature profiles may differ from person to person. Additionally, the tissue signatures and/or signature profile curves may be normalized to facilitate identification of the relevant slopes, offsets, and the like between different tissues. Impedance measurements can be achieved at one or more frequencies, ideally two different frequencies (low and high). Low frequency measurement can be done in range of about 1-10 kHz, or about 4-5 kHz and high frequency measurement can be done in range of about 300 kHz-1 MHz, or between about 750 kHz-1 MHz. Lower frequency measurement mainly represents the resistive component of impedance and correlates closely with tissue temperature where higher frequency measurement represents the capacitive component of impedance and correlates with destruction and changes in cell composition.

Phase angle shift between the resistive and capacitive components of impedance also occurs due to peak changes between current and voltage as result of capacitive and resistive changes of impedance. The phase angle shift can also be monitored as means of assessing tissue contact and lesion formation during RF denervation.

In some embodiments, remodeling of a body lumen can be performed by gentle heating in combination with gentle or standard dilation. For example, an angioplasty balloon catheter structure having electrodes disposed thereon might apply electrical potentials to the vessel wall before, during, and/or after dilation, optionally in combination with dilation pressures which are at or significantly lower than standard, unheated angioplasty dilation pressures. Where balloon inflation pressures of 10-16 atmospheres may, for example, be appropriate for standard angioplasty dilation of a particular lesion, modified dilation treatments combined with appropriate electrical potentials (through flexible circuit electrodes on the balloon, electrodes deposited directly on the balloon structure, or the like) described herein may employ from 10-16 atmospheres or may be effected with pressures of 6 atmospheres or less, and possibly as low as 1 to 2 atmospheres. Such moderate dilation pressures may (or may not) be combined with one or more aspects of the tissue characterization, tuned energy, eccentric treatments, and other treatment aspects described herein for treatment of body lumens, the circulatory system, and diseases of the peripheral vasculature.

In many embodiments, gentle heating energy added before, during, and/or after dilation of a body lumen may increase dilation effectiveness while lowering complications. In some embodiments, such controlled heating with a balloon may exhibit a reduction in recoil, providing at least some of the benefits of a stent-like expansion without the disadvantages of an implant. Benefits of the heating may be enhanced (and/or complications inhibited) by limiting heating of the adventitial layer below a deleterious response threshold. In many cases, such heating of the intima and/or media may be provided using heating times of less than about 10 seconds, often being less than 3 (or even 2) seconds. In other cases, very low power may be used for longer durations. Efficient coupling of the energy to the target tissue by matching the driving potential of the circuit to the target tissue phase angle may enhance desirable heating efficiency, effectively maximizing the area under the electrical power curve. The matching of the phase angle need not be absolute, and while complete phase matching to a characterized target tissue may have benefits, alternative systems may pre-set appropriate potentials to substantially match typical target tissues; though the actual phase angles may not be matched precisely, heating localization within the target tissues may be significantly better than using a standard power form.

In some embodiments, monopolar (unipolar) RF energy application can be delivered between any of the electrodes on the balloon and return electrode positioned on the outside skin or on the device itself, as discussed above. Monopolar RF may be desirable in areas where deep lesions are required. For example, in a monopolar application, each electrode pair may be powered with positive polarity rather than having one positive pole and one negative pole per pair. In some embodiments, a combination of monopolar and bipolar RF energy application can be done where lesions of various depth/size can be selectively achieved by varying the polarity of the electrodes of the pair.

c. Target Temperature

The application of RF energy can be controlled so as to limit a temperature of target and/or collateral tissues, for example, limiting the heating of target tissue such that neither the target tissue nor the collateral tissue sustains irreversible thermal damage. In some embodiments, the surface temperature range is from about 50° C. to about 90° C. For gentle heating, the surface temperature may range from about 50° C. to about 70° C., while for more aggressive heating, the surface temperature may range from about 70° C. to about 90° C. Limiting heating so as to inhibit heating of collateral tissues to less than a surface temperature in a range from about 50° C. to about 70° C., such that the bulk tissue temperature remains mostly below 50° C. to 55° C., may inhibit an immune response that might otherwise lead to stenosis, thermal damage, or the like. Relatively mild surface temperatures between 50° C. and 70° C. may be sufficient to denature and break protein bonds during treatment, immediately after treatment, and/or more than one hour, more than one day, more than one week, or even more than one month after the treatment through a healing response of the tissue to the treatment so as to provide a bigger vessel lumen and improved blood flow.

In some embodiments, the target temperature may vary during the treatment, and may be, for instance, a function of treatment time. FIG. 7 illustrates one possible target temperature profile for a treatment with a duration of 30 seconds and a twelve second ramp up from nominal body temperature to a maximum target temperature of about 68° C. In the embodiment shown in FIG. 7, the target temperature profile during the twelve second ramp up phase is defined by a quadratic equation in which target temperature (T) is a function of time (t). The coefficients of the equation are set such that the ramp from nominal body temperature to 68° C. follows a path analogous to the trajectory of a projectile reaching the maximum height of its arc of travel under the influence of gravity. In other words, the ramp may be set such that there is a constant deceleration in the ramp of temperature ($d^2T/dt^2$) and a linearly decreasing slope (dT/dt) in the temperature increase as 12 seconds and 68° C. are reached. Such a profile, with its gradual decrease in slope as it approaches 68° C., may facilitate minimizing over and/or undershoot of the set target temperature for the remainder of the treatment. In some embodiments, the target temperature profile of FIG. 7 will be equally suitable for bipolar or monopolar treatments, although, in at least some monopolar embodiments, treatment time may be increased.

Figure 8:
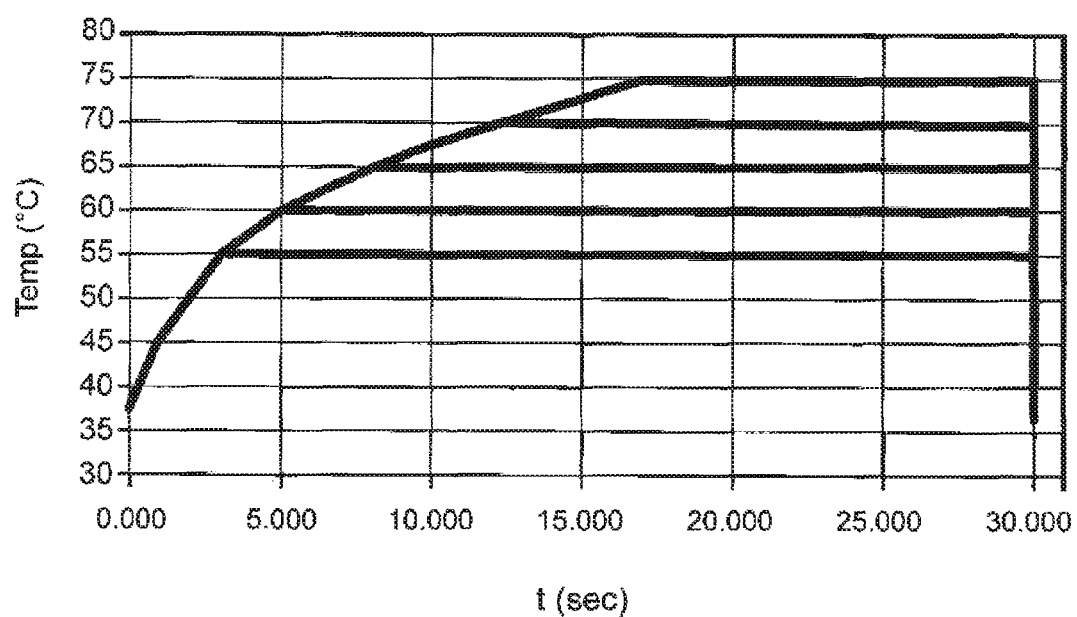
Figure 9:
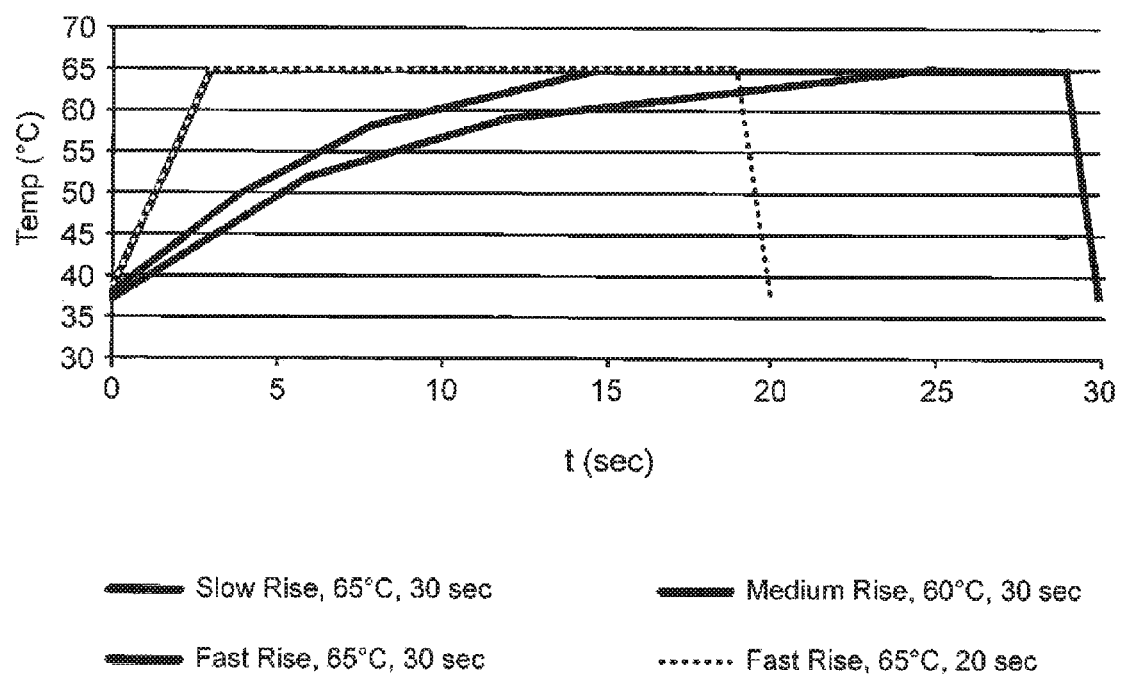
Figure 10:
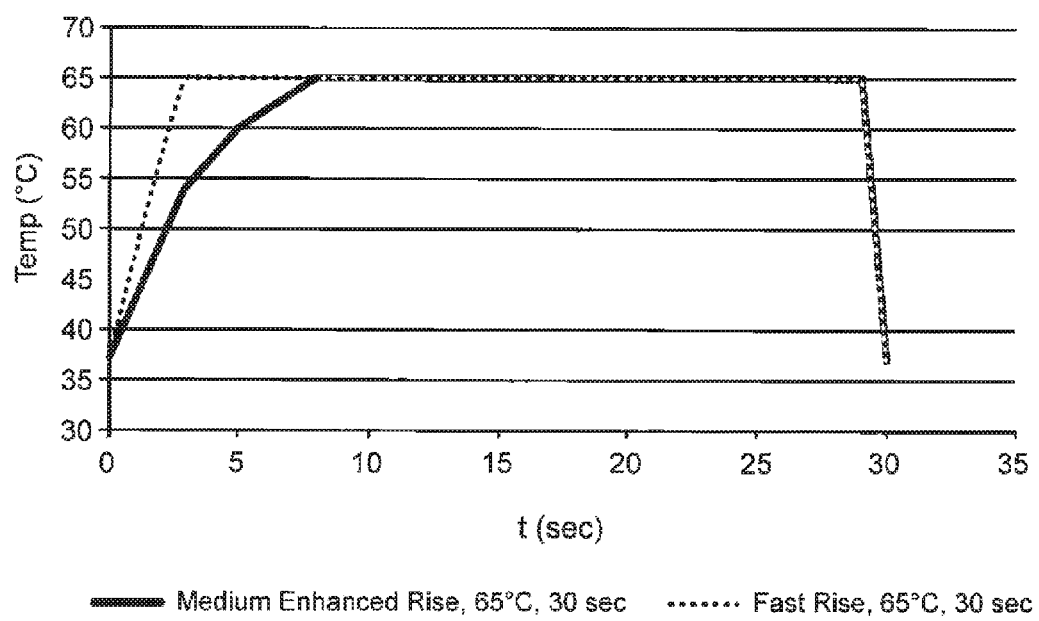

FIGS. 8, 9, and 10 illustrate additional target temperature profiles for use in various embodiments of the disclosure. FIG. 8 illustrates profiles with varying rise times and set target temperatures (e.g. one profile with an approximately 3 second rise time and 55° C. set temperature, one with a 5 second rise time and 60° C. set temperature, one with an 8 second rise and 65° C. set temperature, one with a 12 second rise and 70° C. set temperature, and one with a 17 second rise and 75° C. set temperature).

FIGS. 9 and 10 illustrate temperature profiles that utilize different rise profiles, some of which approach the set target temperature relatively aggressively (e.g., the "fast rise" profiles), others of which approach the set target temperature less aggressively (e.g., the "slow rise" profile). It has been experimentally determined that the "medium enhanced rise" temperature profile shown in FIG. 10 provides optimal results for at least some treatment protocols, although not all embodiments of the present disclosure are limited to this temperature profile, and different treatments and different circumstances may advantageously use other profiles. The medium enhanced rise may be an example embodiment in that it efficiently warms target tissue to the target temperature while avoiding the deleterious microscopic thermal damage that a more aggressive heating profile may cause while also providing for an optimized overall treatment time. For each of the target temperature profiles shown, a temperature ramp embodying or approximating a quadratic equation may be utilized, however, any function or other profile that efficiently heats tissue, optimizes treatment time, and avoids thermal damage to target tissue may be used. However, in still other embodiments, it will not be necessary to utilize a temperature profile that achieves all of these goals. For instance and without limitation, in at least some embodiments, optimization of treatment time may not be essential.

Both bench top and animal experimentation were undertaken to optimize and verify the target temperature profile used in denervation embodiments of the Vessix system. The following summarizes the bench top experimentation and analysis supporting the selection of the medium enhanced rise temperature profile as an example embodiment.

The tests were carried out to determine which rise time algorithm would provide optimal levels of effectiveness and safety. Some previous rise time algorithms had simply gone up to the set temperature as fast as possible, and it was believed that this was not necessarily the best course of action in at least some circumstances. Efficacy was qualitatively assessed with three dimensionless parameters. The objective was to determine the algorithm that would produce the least amount of charring, denaturing, and dehydrating of the tissue at the treatment zone, based on visual inspection, while also providing good efficacy.

A water bath was brought up to 37° C. to simulate body temperature, and a liver sample was placed in the bath to simulate conditions in vivo. Good apposition of the device was verified by noting the impedance values of the electrode-tissue interface of each bipolar electrode pair in contact with tissue. A higher impedance (>500 Ohms) was used as the benchmark for good apposition.

After the temperature profiles of FIGS. 9 and 10 were run, the liver specimen was measured at each treatment site for the length and width of the lesion at the surface, the depth of penetration, and length and width of the lesion at a 2 mm depth. The analyst had no knowledge of which treatments had been done in which order so as to reduce reporting bias. Any observations of significant tissue damage were also recorded.

FIGS. 11 and 12 show in tabular form efficacy metrics that were created to relate depth of penetration to other efficacy measures. The first is depth of penetration divided by the square root of the area of the lesion at the surface. This metric relates the depth to the lesion damage on the surface to the area of the surface lesion in a non-dimensional form. A value of 100% means that the depth of penetration was equal to the average size of the surface lesion. The next metric is area at 2 mm divided by the area at the surface. This metric reveals how well the heat is penetrating the tissue. A value of 100% means that the areas at 2 mm deep and surface area are the same. The last metric is depth of penetration times the width of the lesion at 2 mm divided by the area at the surface. This number provides information about the general shape of the lesion, and whether the energy tends to propagate radially from the electrode or pierce the tissue. A value of 100% means that the cross sectional area of lesion size was equal to the size of the surface of the lesion.

After carefully reviewing all of the experimental data, it was decided that the medium enhanced rise profile was the best temperature rise algorithm to use for certain embodiments, although, again, other target temperature profiles may also be appropriately used in conjunction with the disclosed embodiments of the present disclosure.

d. Control Algorithm

Figure 13:
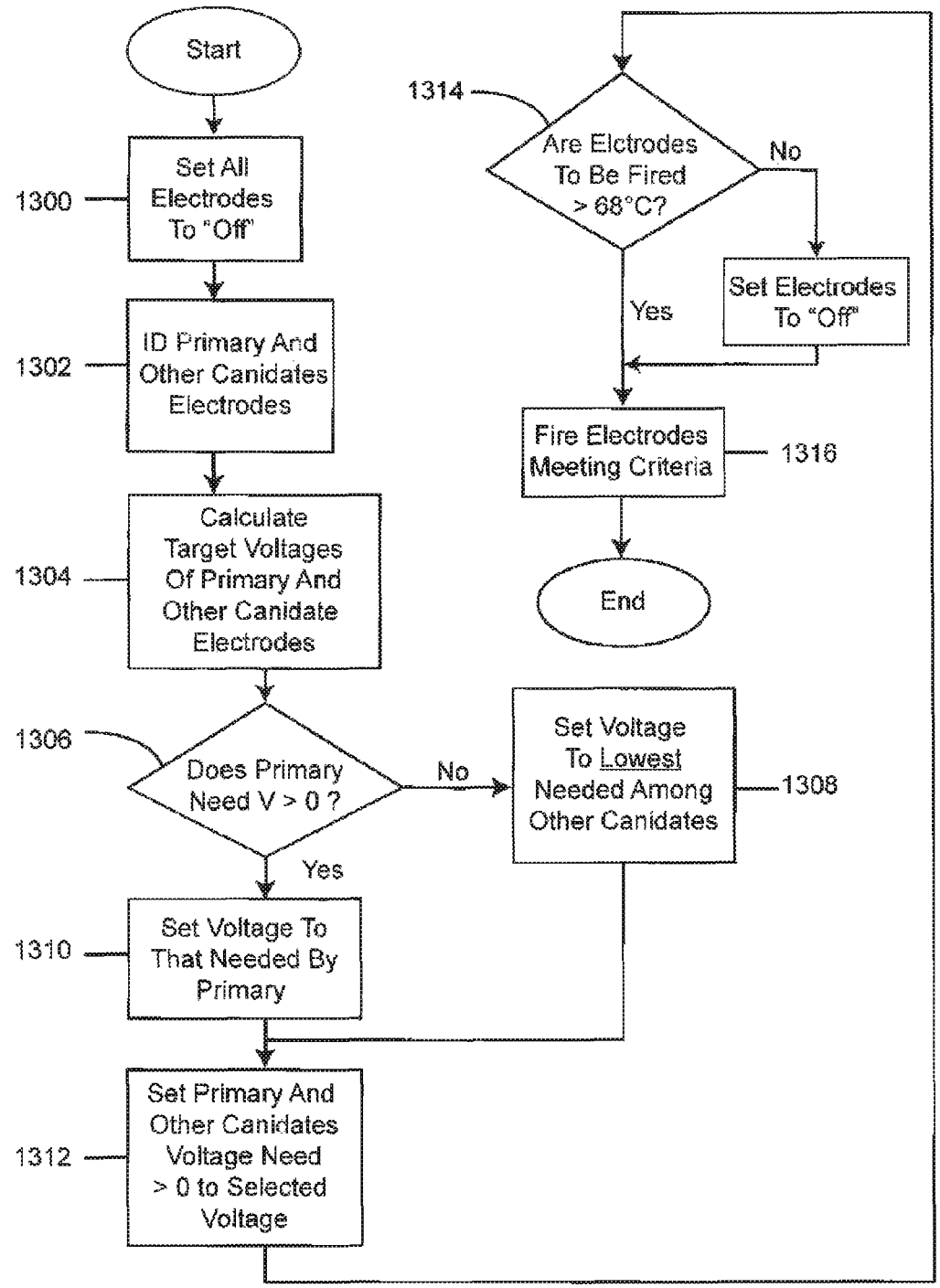
FIGS. 13 and 14 illustrate one embodiment of a control loop.
Figure 14:
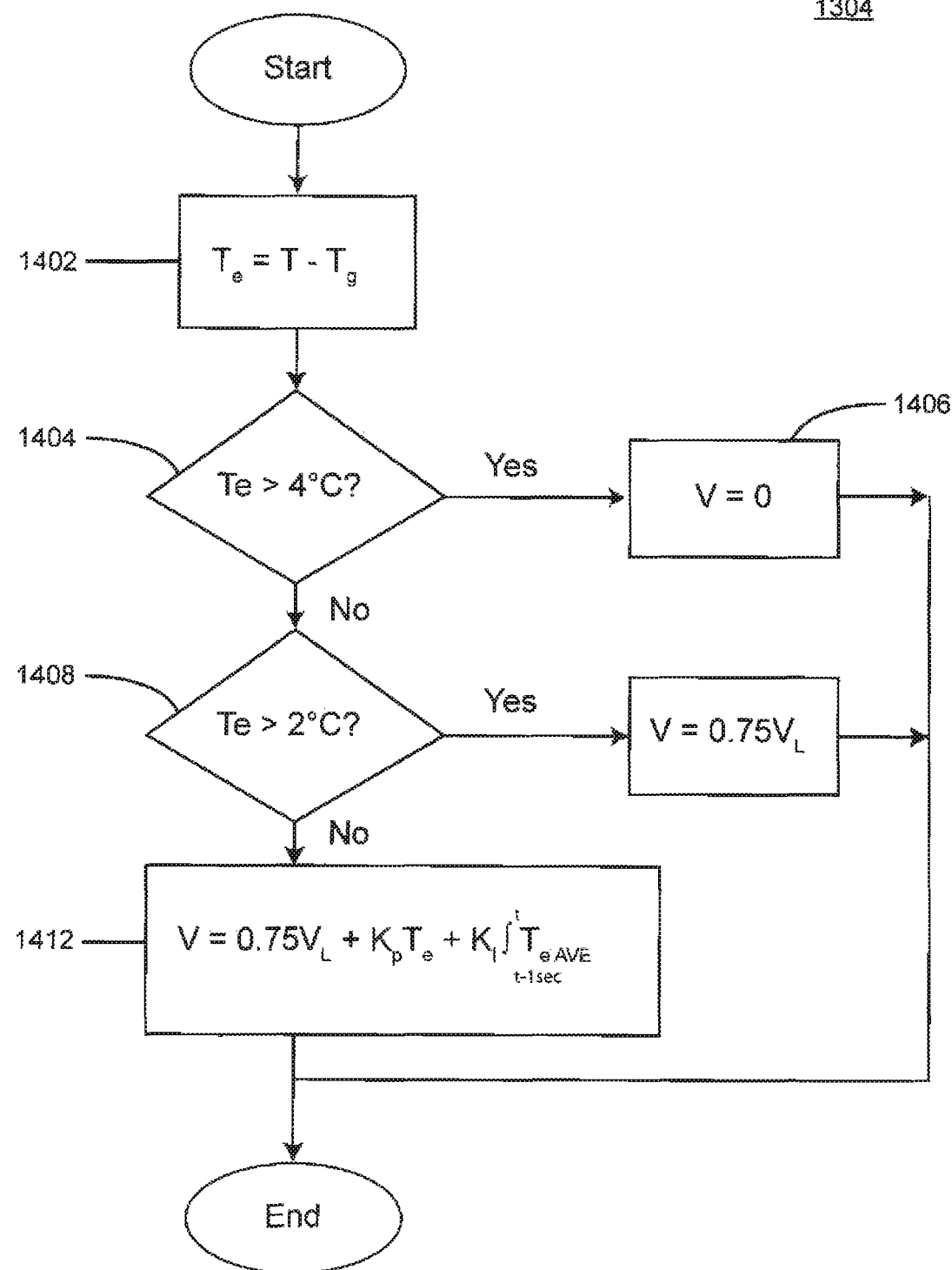

FIGS. 13 and 14 illustrate one embodiment of a method for controlling energy application of an electrosurgical device, such as those described above and shown in FIGS. 1-6, or other devices, based on a target temperature profile, such as those described above and shown in FIGS. 7-10, or other profiles. The control method may be executed using the processing functionality of the control unit 110 of FIG. 1 and/or control software, described in further detail above, or in other manners. In at least some instances, the control method provides for fine regulation of temperature or other treatment parameter(s) at the various treatment sites of the device, while utilizing a relatively simple and robust energy generator to simultaneously energize several of the electrodes or other delivery sites at a single output setting (e.g. voltage), which may minimize cost, size and complexity of the system. The control method may minimize deviation from target temperature or other treatment parameter(s), and hence minimize variation in demand on the energy generator (e.g. voltage demand) during any time slice of the treatment.

In some embodiments, it will be desirable to regulate the application of RF or other energy based on target temperature profiles such as those described above to provide for a gentle, controlled, heating that avoids application of high instantaneous power and, at a microscopic level, associated tissue searing or other damage, which could undesirably result in heat block or otherwise cause a net reduction in thermal conduction heat transfer at the device/tissue interface. In other words, by avoiding higher swings in temperature and the resultant heavier instantaneous application of energy to reestablish temperature near the target temperature, tissue integrity at the immediate interface location may be preserved. Tissue desiccation may result in a net loss of thermal conductivity, resulting in reduced effective transfer of gentle, therapeutic delivery of energy to target tissues beyond the electrode/tissue interface.

Those of skill in the art will appreciate that although the particular control method of FIGS. 13 and 14 is presented for purposes of illustration in the context of the particular electrosurgical devices already described above, that these control methods and similar methods could be beneficially applied to other electro-surgical devices.

In general, the control method embodiment of FIGS. 13 and 14 seeks to maintain the various treatment sites at a pre-defined target temperature, such as at one of the target temperature profiles of FIGS. 7-10. It does so in this embodiment primarily by regulating output voltage of the RF generator and determining which of the electrodes will by energized at a given time slice (e.g. by switching particular electrodes on or off for that cycle).

The output setting of the generator and switching of the electrodes may be determined by a feedback loop that takes into account measured temperature as well as previous desired output settings. During a particular treatment cycle (e.g. a 25 millisecond slice of the treatment), each of the electrodes may be identified for one of three states: off, energized, or measuring. In some embodiments, electrodes will only be in energized and/or measuring states (an electrode that is energized may also be measuring) if they meet certain criteria, with the default electrode state being off. Electrodes that have been identified as energized or measuring electrodes may have voltage applied or be detecting temperature signals for a portion of the cycle, or for the entire cycle.

Figure 15:
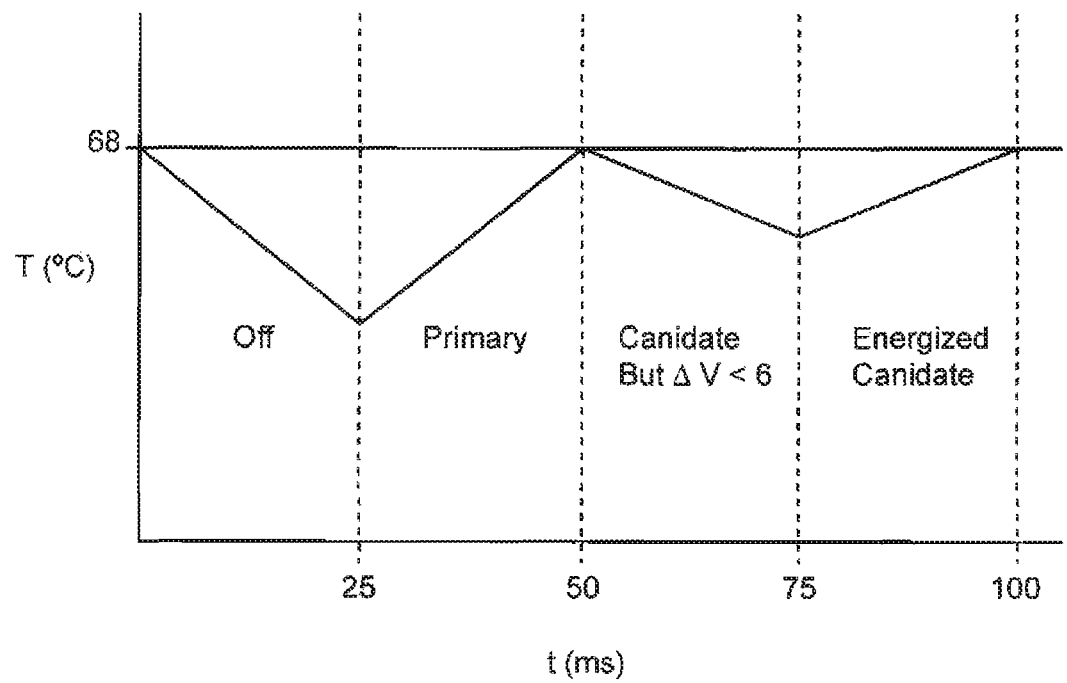
FIG. 15 shows one non-limiting example of a change in temperature over time for an electrode.
Figure 16:
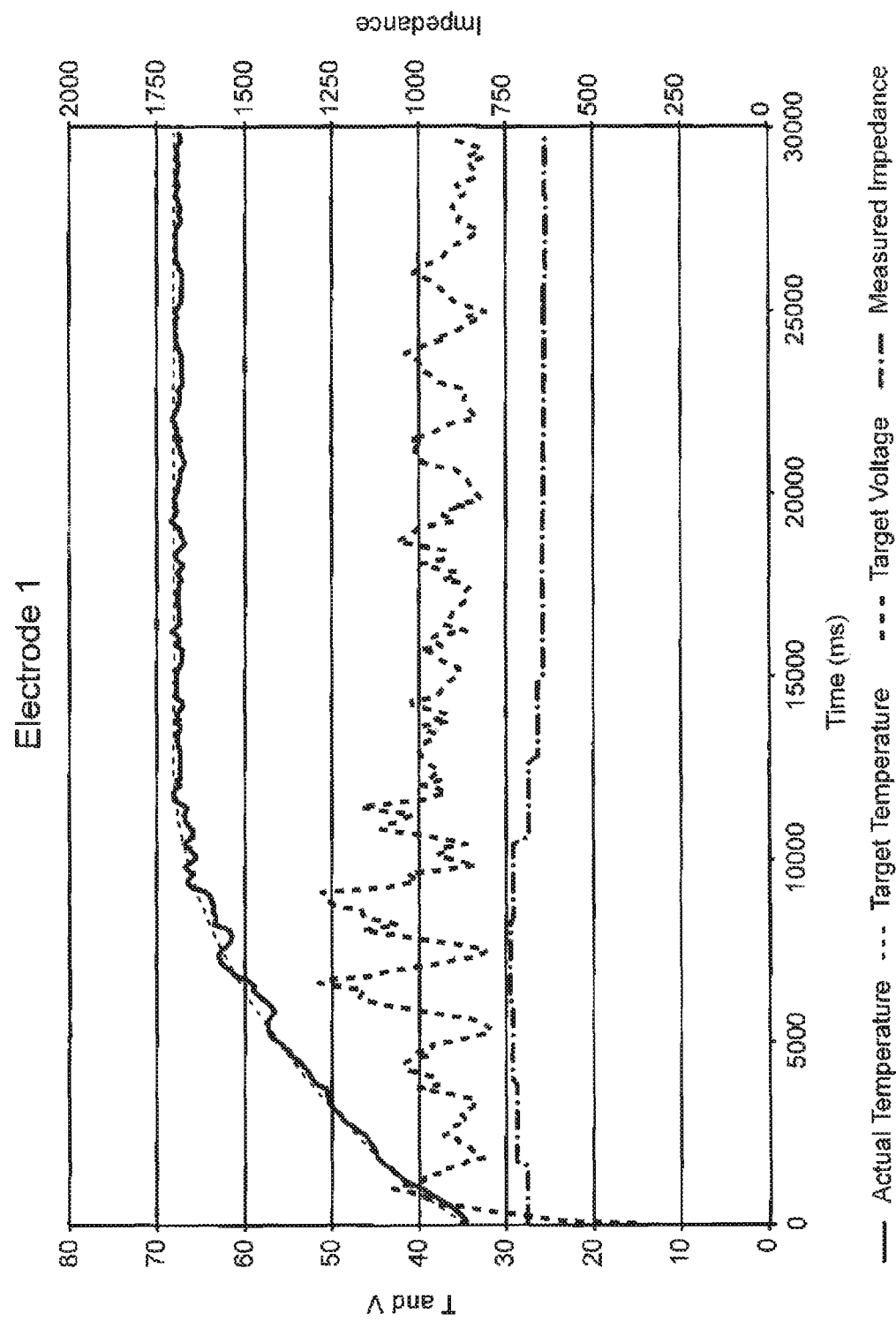
FIGS. 16-23 shows one non-limiting example of various attributes associated with eight electrodes during a treatment.
Figure 17:
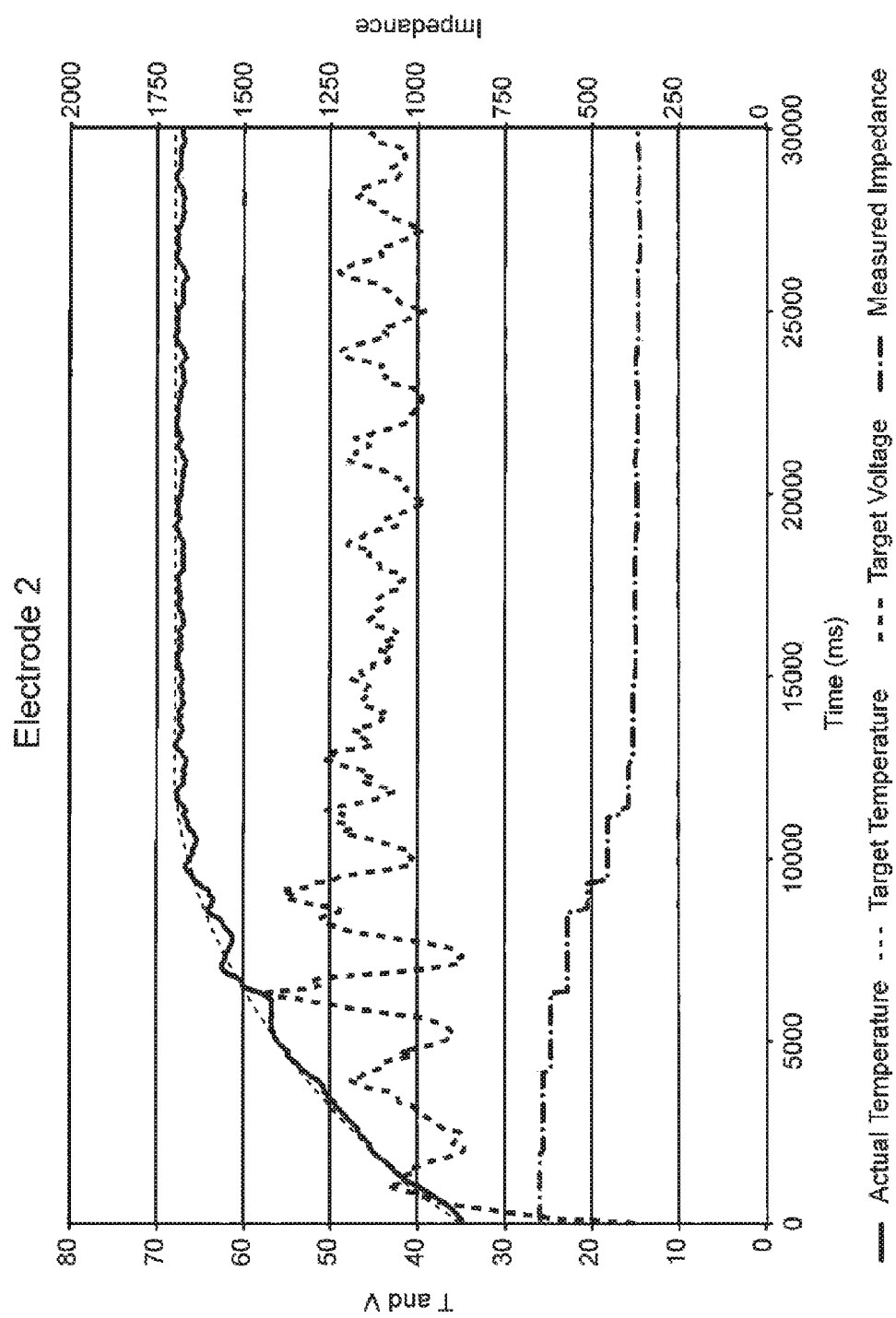
Figure 18:
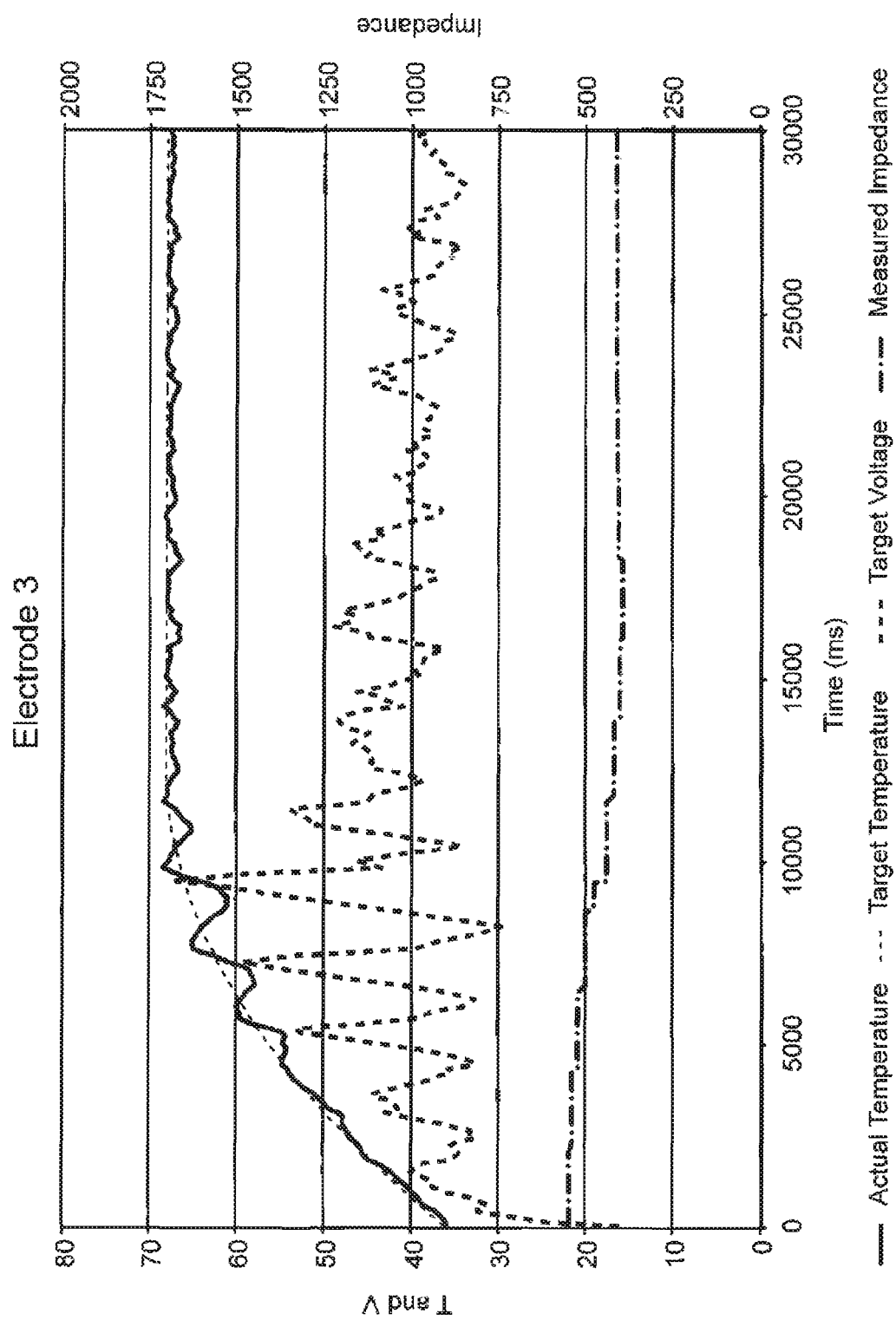
Figure 19:
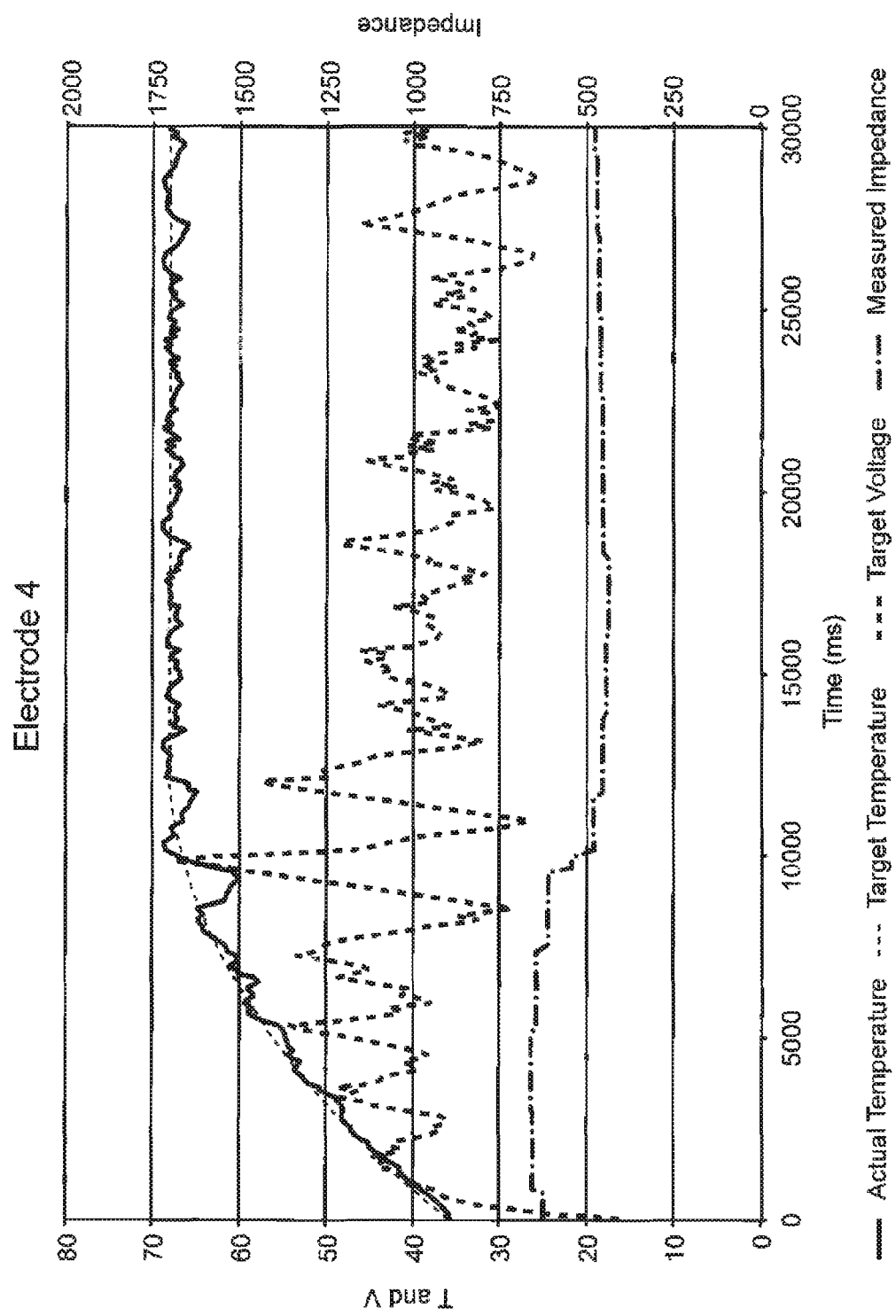
Figure 20:
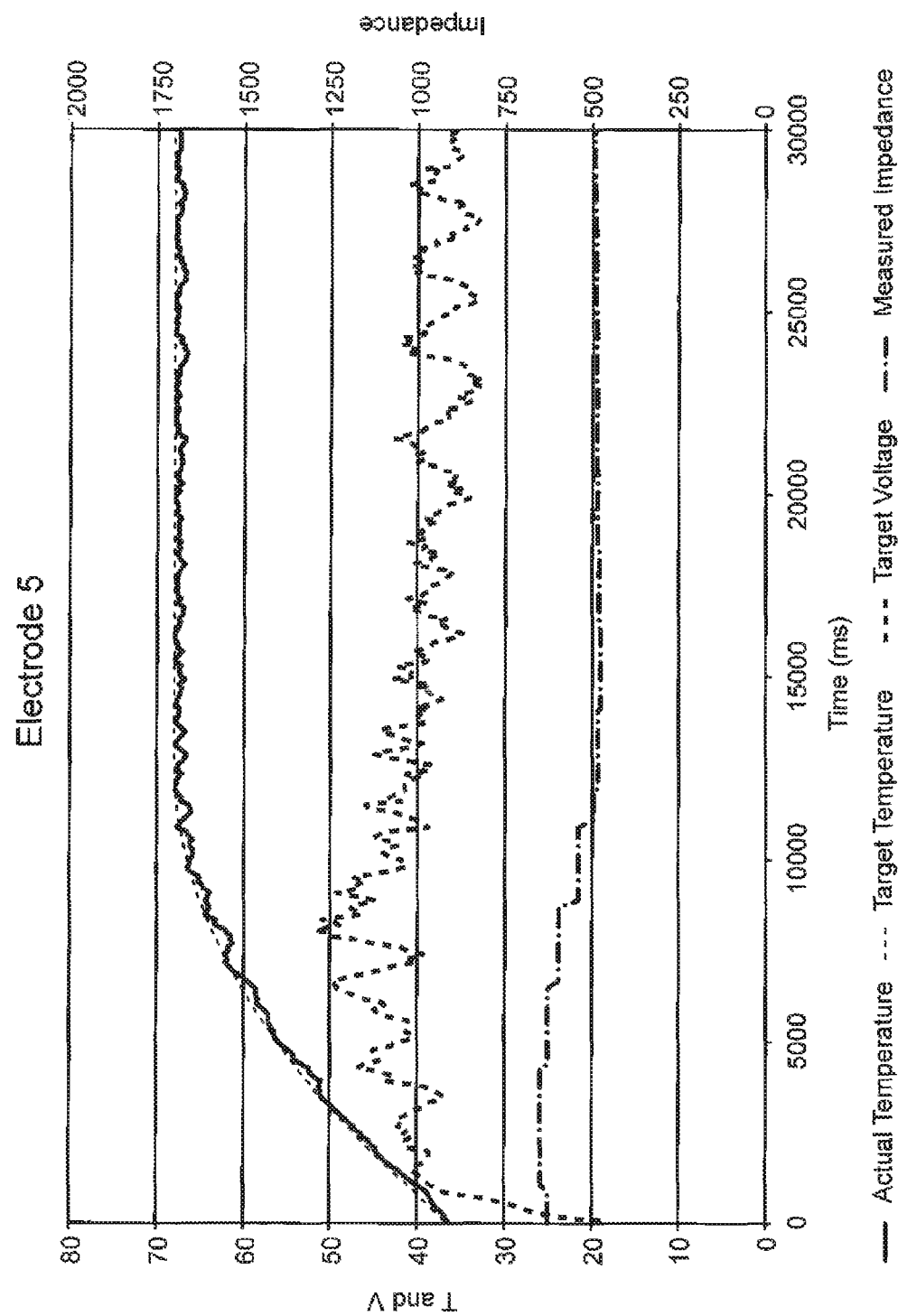
Figure 21:
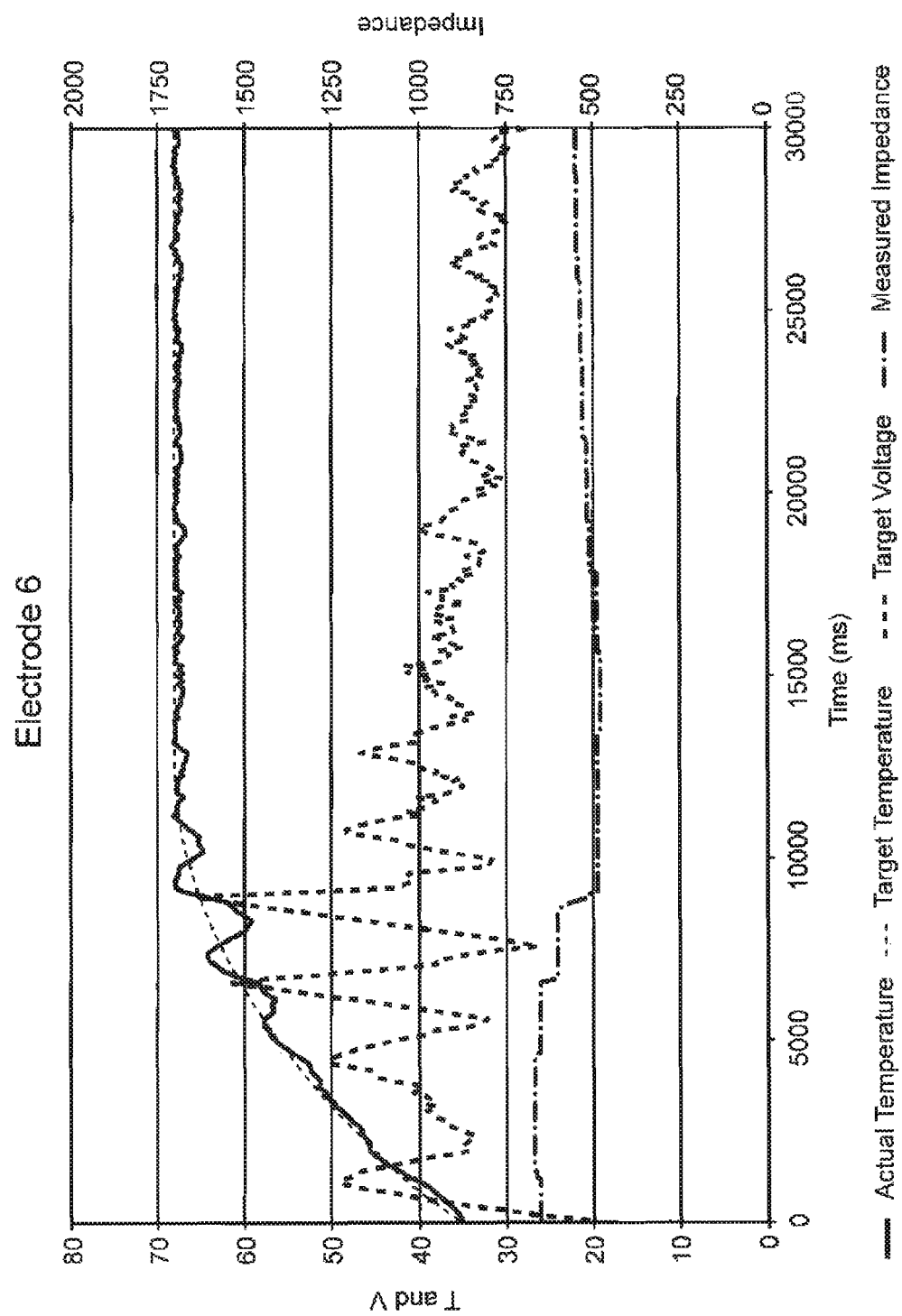
Figure 22:
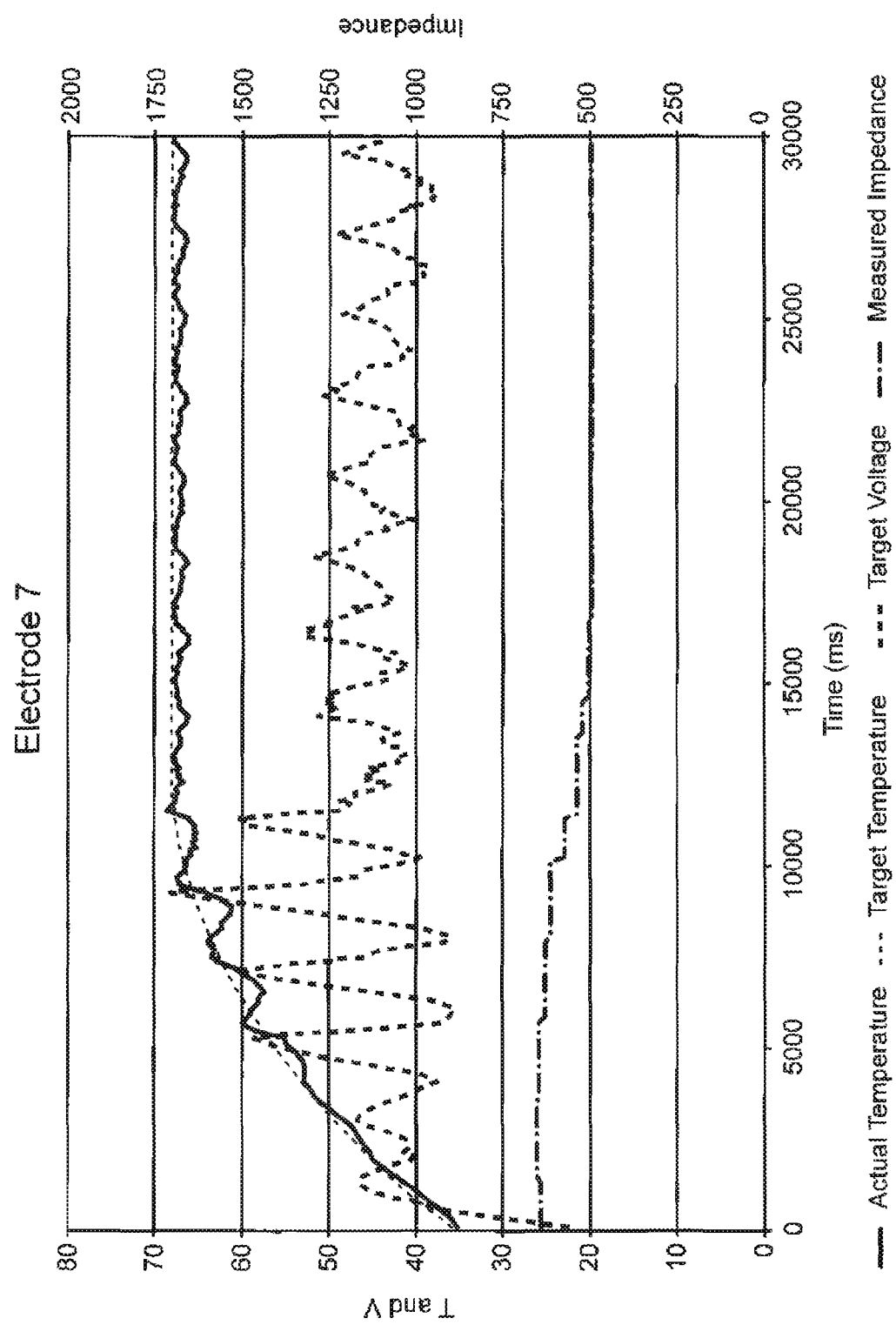
Figure 23:
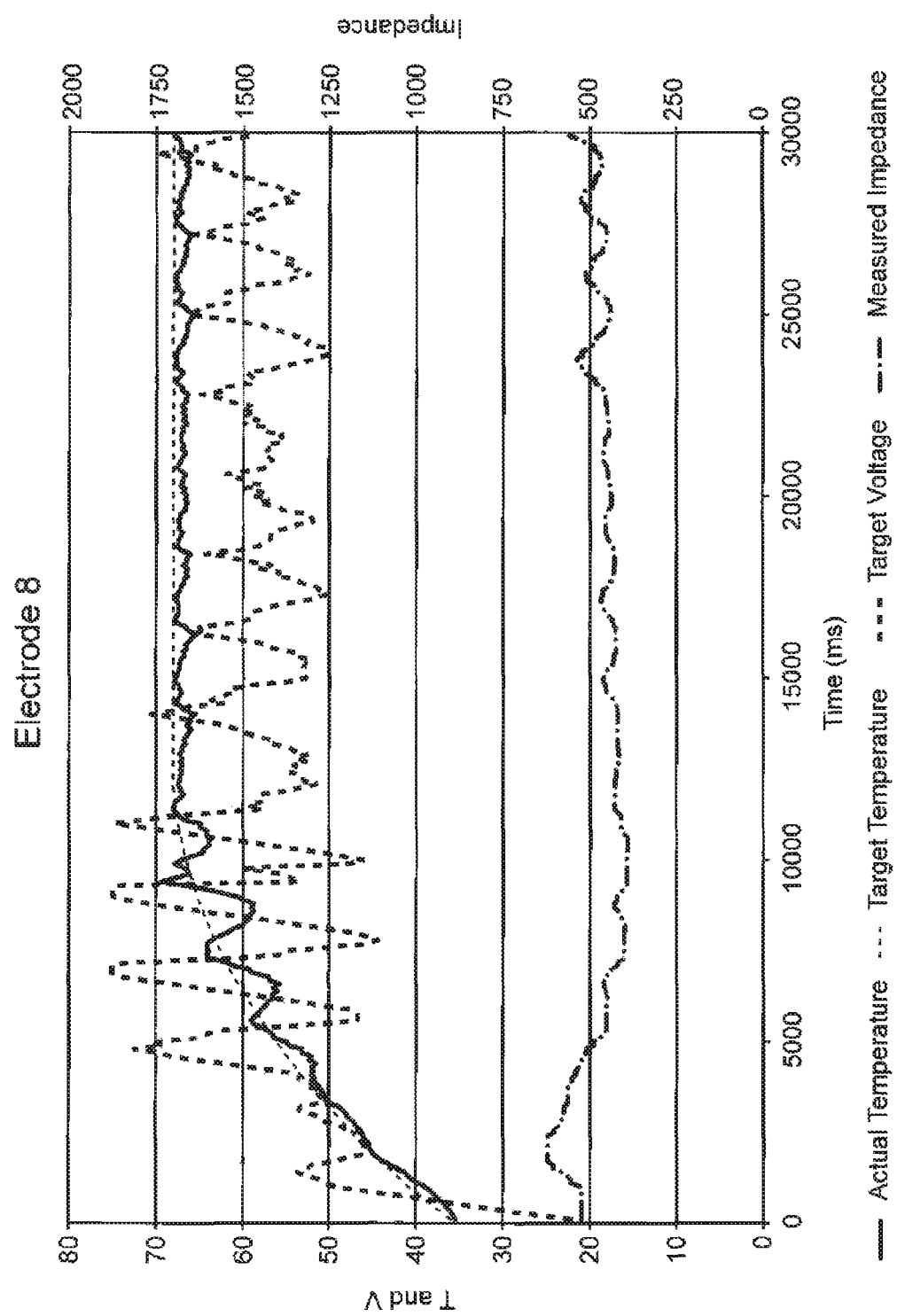

The control loop embodiment of FIGS. 13 and 14 is designed to keep as many candidate electrodes as possible as close to target temperature as possible while minimizing variations in temperature and hence minimizing variations in voltage demand from treatment cycle to treatment cycle. FIG. 15 shows an exemplar time/temperature plot over four treatment cycles for an electrode illustrating how one embodiment of a control algorithm maintains the target temperature.

The control loop embodiment of FIGS. 13 and 14 will now be described in detail.

As indicated at step 1300, each electrode is initially set to off. At step 1302, one of the electrodes is designated as a primary electrode for that treatment cycle. As discussed in further detail below, during the treatment, the primary electrode designated will vary from treatment cycle to treatment cycle (e.g. cycle through all of the available electrodes). The determination of which electrode will be designated as the primary electrode may be done by accessing a look-up table or using any other suitable functionality for identifying a primary electrode and varying the choice of primary electrode from treatment cycle to treatment cycle.

At step 1302, additional electrodes may also be designated as candidate electrodes for energization and/or measuring during that treatment cycle. The additional electrodes designated may be candidates by virtue of being in a certain relationship or lacking a certain relationship relative to the designated primary electrode for that treatment cycle.

For instance, in some bipolar electrode embodiments, some of the electrodes on the electro-surgical device may be arranged in a manner such that there may be a potential for current leakage between the primary electrode and those other electrodes if both the primary electrode and those additional electrodes are energized simultaneously in a treatment cycle, which may undesirably cause interference with the temperature measurement by the associated heat sensing device, imprecision in the amount of energy delivered at each electrode, or other undesirable consequences. For instance, in the embodiment illustrated in FIG. 1C, if electrode pad 150c is designated as a primary electrode, electrode pads 150d and 170d, which have negative poles immediately adjacent or proximate the positive pole of electrode pad 150c, may be considered to be not candidates for measuring and/or energization for that particular treatment cycle, since they are leakage-inducingly proximate to the designated primary electrode. Additionally, in this embodiment, electrode pad 150b, which has a positive pole immediately adjacent or proximate the negative pole of electrode pad 150c, may be considered to not be a candidate, since it is also leakage-inducingly proximate to the designated primary electrode. Furthermore, in this particular embodiment, electrode pad 170b would also be considered a non-candidate because it is on the same flex structure as the leakage-inducingly proximate electrode pad 150b. Finally, in this particular embodiment, electrode pads 150a and 170a would be considered candidates because they are adjacent non-candidates.

As another non-limiting example, in some monopolar electrode embodiments, the candidate electrodes are the monopolar electrodes that have similar measured or estimated electrical circuit properties to one or more measured or estimated properties of the electrical circuit associated with the primary electrode. In other words, in some monopolar systems, it may be desirable to only simultaneously energize monopolar electrodes that define substantially similar electrical circuits to the electrical circuit defined by the primary monopolar electrode (e.g. the circuit defined by the monopolar electrode, the common electrode, and a pathway through the patient's tissue). In some instances, this may facilitate uniformity in current flow during energization. In other embodiments, a pre-defined table or other listing or association will determine which electrodes are candidate electrodes based on the current primary electrode.

In at least some embodiments, switches associated with non-candidates will be opened to isolate the non-candidates from the rest of the system's circuitry. This switching, in at least some embodiments, could also or alternatively be used to otherwise maximize the number of available electrode pairs available for energization provided that a common ground between pairs is not affected by the switching off.

In other embodiments, the electro-surgical device may be configured to avoid the potential for leakage or otherwise take such leakage into account, and, accordingly, all the electrodes of the device may be candidates for energization and/or measuring during a treatment cycle.

In some embodiments, the assignment of an electrode as either the primary electrode, candidate, or non-candidate may be determined by a sequence matrix or look up table in an array that identifies the status of each of the electrodes and an order for the designation of primary electrodes. In one non-limiting embodiment, the primary electrode designation cycles circumferentially through the proximate electrodes and then circumferentially through the distal electrodes (e.g. in FIG. 1C, the sequence may be 170a, b, c, d, 150a, b, c, d). However, any pattern or other methodology could be used including ones that optimize distance between the next in sequence, the nearness of next in sequence, or the evenness of distribution.

In some embodiments, additional conditions may result in a particular electrode being set to off for a particular treatment cycle and/or for the remainder of the treatment. For instance, as discussed below, during the course of treatment, as much as 4° C. temperature overshoot may be allowed (e.g., even if such overshoot results in the electrode not being energized, it will not necessarily be set to off and still available for measuring); however, in at least some embodiments, if eight consecutive treatment cycles measure temperature overshoot for a particular electrode, that electrode will be set to off for the remainder of the treatment, with the treatment otherwise continuing and without otherwise changing the control loop process discussed below.

At step 1304, target voltages for each of the primary and other candidate electrodes are determined. In this particular embodiment, a target voltage for a particular electrode may be determined based on a temperature error associated with the treatment site of that electrode as well as the last target voltage calculated (although not necessarily applied) for that electrode. Temperature error may be calculated by measuring the current temperature at the treatment site (e.g. utilizing the heat sensing device associated with the electrode proximate that treatment site) and determining the difference between the measured temperature and the target temperature for that instant of time in the treatment.

Those of skill in the art will appreciate that while this particular embodiment is described as using voltage as a control variable, that power could be used as an alternative to voltage for the control variable, based on, for instance, a known relationship between power and voltage (i.e. power equaling voltage times current or impedance).

FIG. 14 illustrates one embodiment of a sub-routine for determining a target voltage for an electrode. At 1402, a temperature error from target ($T_e$) is calculated by subtracting the target temperature at that time ($T_g$) from the actual temperature ($T$) (e.g. as measured by a thermistor associated with that electrode). At 1404, it is determined whether the temperature error calculated at 1402 is greater than 4° C. (i.e. if the target temperature is 68° C., determining if the temperature as measured by the thermistor is above 72° C.). If the temperature error is greater than 4° C., the sub-routine assigns that electrode a target voltage of zero for that treatment cycle at 1406. If the temperature error is not greater than 4° C., the subroutine proceeds to 1408 and determines whether the temperature error is greater than 2° C. If the temperature error is greater than 2° C., at 1410, the sub-routine assigns that electrode a target voltage of 75% (or another percentage) of the last assigned target voltage for that electrode. If the temperature error is not greater than 2° C., at 1412, the sub-routine may assign a target voltage for that electrode based on the equation:

$$V = K_L V_L + K_P T_e + K_I \int_{t-n\,sec}^{t} T_{e\,AVE}$$

where:
V is the target voltage;
$T_e$ is a temperature error from target;
$V_L$ is the last assigned electrode voltage;
$K_L$, $K_P$, and $K_I$ are constants; and
n is a time value ranging from 0 to t seconds.

In some embodiments, including the embodiment of FIG. 14, the equation used may be:

$$V = 0.75 V_L + K_p T_e + K_I \int_{t-1\text{sec}}^{t} T_{eAVE}$$

where:
V is the target voltage;
$T_e$ is the temperature error from target;
$V_L$ is the last assigned electrode voltage;
$K_P$ is a constant from proportionate control; and
$K_I$ is a constant from integral control.

In some embodiments, it may be beneficial to use only the last assigned electrode voltage for determining a target voltage, rather than utilizing averages of voltages or voltages from earlier treatment cycles, as, in some cases, use of earlier voltages may be a source for computational error in embodiments that focus on fine control of the target temperature.

Returning to FIG. 13, once target voltages are determined for the primary electrode and other candidate electrodes, at step 1306, it is determined whether the target voltage for the primary electrode is greater than zero. If not, at 1308, the output voltage of the RF generator is set for that treatment cycle to the lowest target voltage determined at 1304 for the other candidate electrodes. If the target voltage determined at 1304 for the primary electrode is greater than zero, at 1310, the output voltage of the RF generator is set for that treatment cycle to the target voltage of the primary electrode.

At step 1312, the primary and other candidate electrodes with a target voltage greater than zero are identified as electrodes to be energized. In alternative embodiments, candidate electrodes other than the primary will only be energized if the target voltages determined for those electrodes is 6V greater than the set voltage.

In still other embodiments, candidate electrodes other than the primary will only be energized if the target voltages determined for these electrodes are 1, 5 or 10V greater than the set voltage.

At step 1314, it is determined whether the electrodes to be energized are currently at temperatures greater than 68° C. Those electrodes that are at temperatures greater than 68° C. are switched off or otherwise prevented from being energized in that treatment cycle, and those electrodes otherwise meeting the above criteria are energized at the set voltage at step 1316. Subsequently, another treatment cycle begins, and the control loop of FIG. 13 is repeated until the treatment is complete. In some embodiments, each treatment cycle will be non-overlapping with the previous and next cycles (e.g. the steps of FIG. 13 will be completely performed before the next cycle's steps begin), although, in other embodiments, the cycles may be overlapping at least to some extent.

FIGS. 16-23 are charts of temperature (target and actual) and target voltage over time for a treatment employing a Vessix System for renal denervation that utilizes the control loop of FIG. 13 to regulate actual temperature at the device's eight electrodes to the target temperature profile. It should be understood that the target voltage charted in these Figures is not the same as the actual voltage applied to the electrodes, since, as described above, the target voltage for only one of the electrodes is used to set the actual voltage applied in each treatment cycle. As shown in FIGS. 16-23, the control loop of FIG. 13 functions to precisely maintain the actual temperature at each electrode of the device at the target temperature. As also shown in FIGS. 16-23, measured impedance may decrease in some instances over the course of the treatment (particularly at the beginning of the treatment), reflecting increased mobility of the ions in the tissue in response to the high frequency RF energy.

Figure 26:
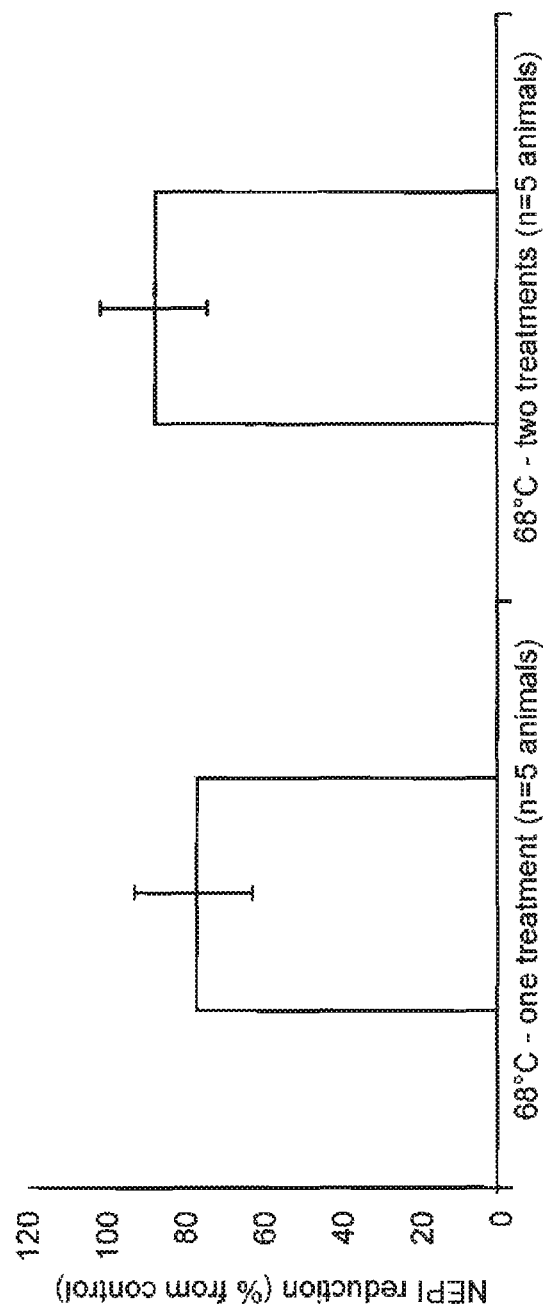
Figure 27:
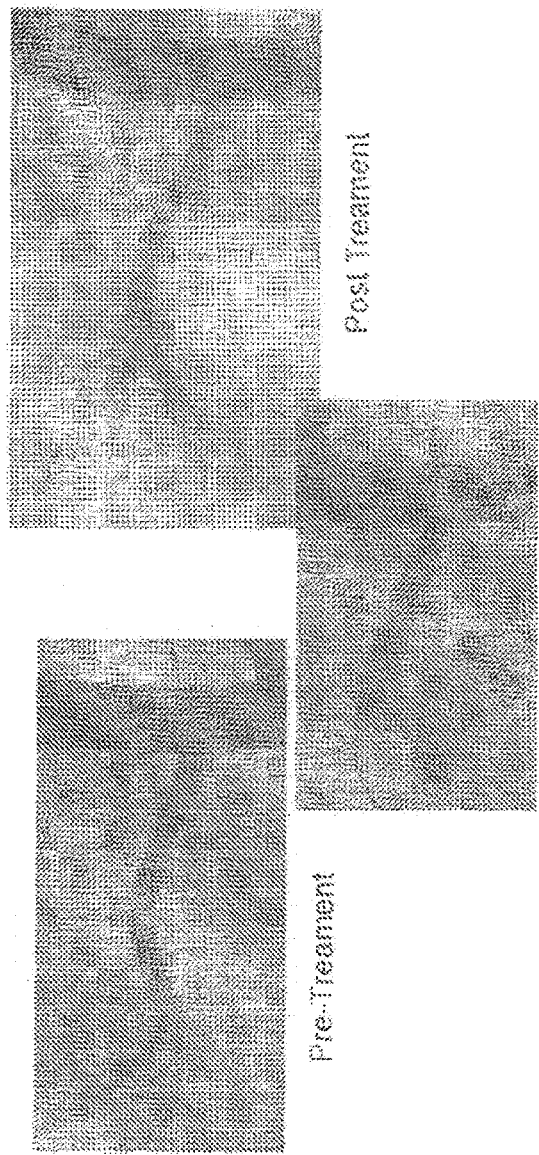
Figure 28:
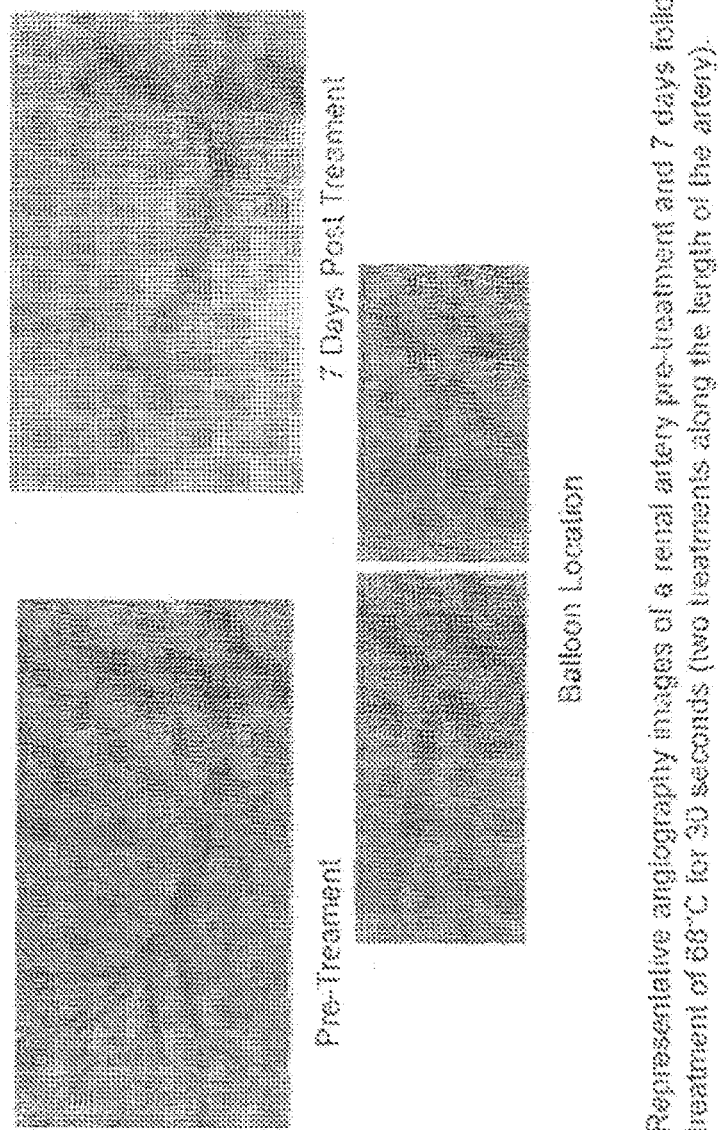
Figure 29:
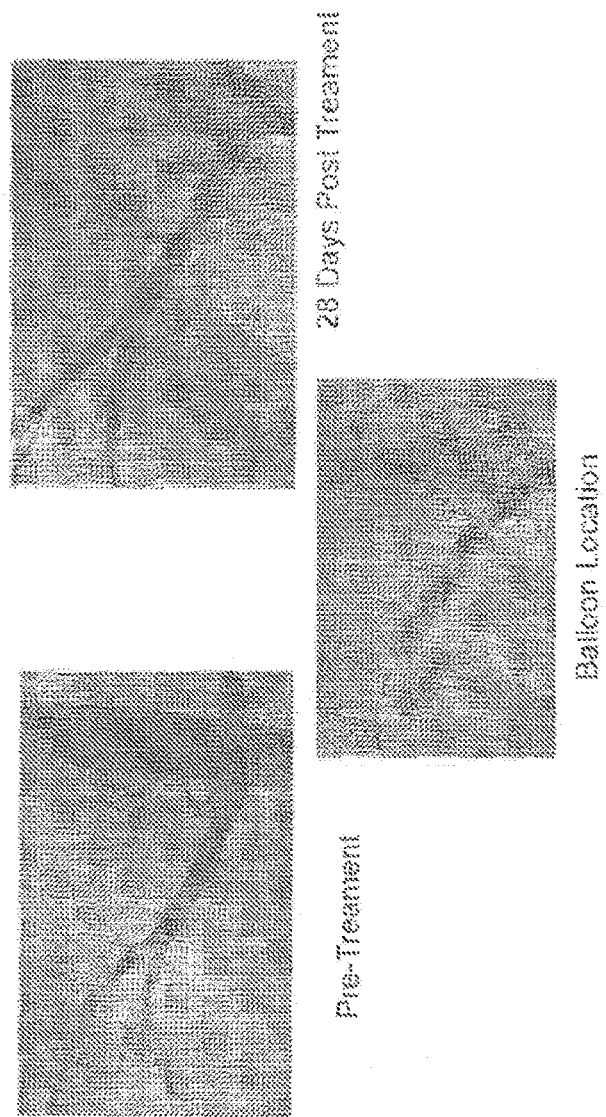
Figure 30:
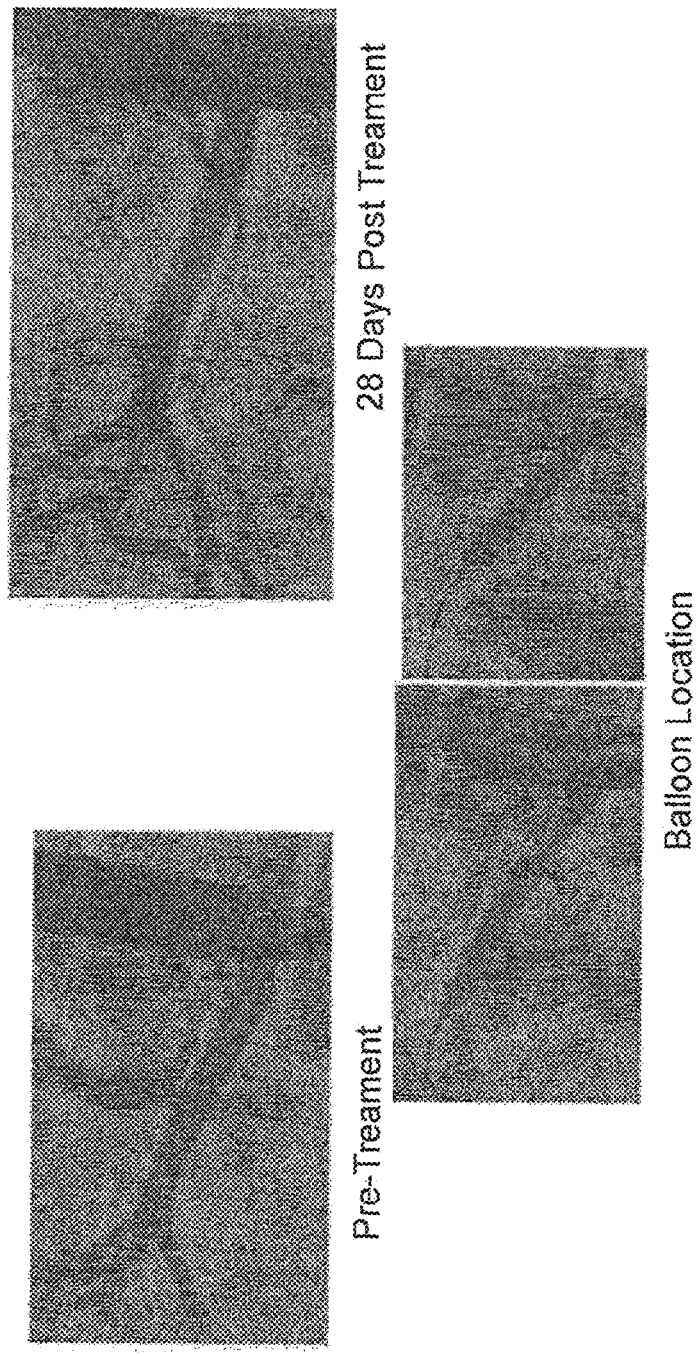

It has been experimentally determined that an example embodiment of the temperature control method described above, when employed as part of the Vessix System for Renal Denervation, provides effective reduction of norepinephrine (NEPI) concentration. In one experiment, efficacy and safety of the Vessix System for Renal Denervation was assessed in healthy juvenile Yorkshire swine at 7 and 28 days post-treatment, including an assessment of kidney NEPI concentration levels at 7 days post-treatment. FIG. 25 is a table summarizing the study design for this particular experiment. Efficacy of groups 1 and 2 was measured as percent reduction of NEPI level in the treated arteries vs. untreated contralateral control kidney in each animal at 7 days. FIG. 26 shows percent NEPI reduction of both groups (as means+/−SD). There were no significant changes in body weight, body condition score or clinical pathology parameters in any animal over the course of the study. Overall, the average baseline vessel diameters were similar amongst groups across all time points. Luminal gain or loss was calculated (average pre-necropsy–average baseline diameter) and exhibited similar luminal gains for treated vessels when compared to vessels of the animals that were not treated. Representative angiography images of the renal artery pre-treatment, 7 and 28 days post RF treatment are shown in FIGS. 27-30. No perforation, dissection, thrombus nor emboli were detected acutely or chronically via angiography analysis.

e. Nerve Signal Stimulation and Monitoring

In at least some of the embodiments described above, or in alternative embodiments, renal-denervation treatment methods and systems may provide for stimulation of nerve signals and monitoring for nerve signal response in the tissue proximate the treated renal artery. In some instances, this electrogram of neural activity may provide an assessment of the denervation treatment's efficacy and/or provide feedback for regulating the treatment. In at least some embodiments, such an electrogram provides for an assessment of whether neural activity is present and/or has shifted (e.g. decreased) relative to a measured baseline, and does not involve mapping or quantifying the presence of neural tissue proximate the renal artery.

In one embodiment, the same electrode assemblies used to deliver the denervation treatment, such as the bi-polar electrode pairs on the distal and proximal electrode pads 150a-d and 170a-d shown in FIG. 1C, may also be configured for stimulation of nerve signals and monitoring for nerve signal responses. For instance, one of the proximal bipolar electrode pairs on one of proximal electrode pads 150a-d may be used to stimulate a nerve signal and one of the distal bipolar electrode pairs on one of distal electrode pads 170a-d may be used to monitor for a nerve signal response. Alternatively, a distal bipolar electrode may be used for stimulation and a proximal bipolar electrode may be used for monitoring. In these or other embodiments, stimulation and sensing may be performed by axially or circumferentially adjacent electrode pairs.

Electrodes 222 having the size, spacing, other geometries and other characteristics as described above in the context of FIG. 2A may be sufficient for stimulation and monitoring of nerve signals, although, in alternative embodiments, the electrodes may be further reduced in size and/or other characteristics may modified to provide higher signal resolution. Other modifications to the systems and devices described herein may also be made to minimize interference with the stimulation and (particularly) monitoring of nerve signals. For instance, in some embodiments, the layout of the system's circuitry (such as the RF generator's internal circuitry) and/or the pairing, twisting, and other characteristics of the wiring associated with the catheter/flex circuitry may be optimized to reduce the inherent capacitance of the circuitry to provide for reduced electromagnetic flux.

Figure 42:
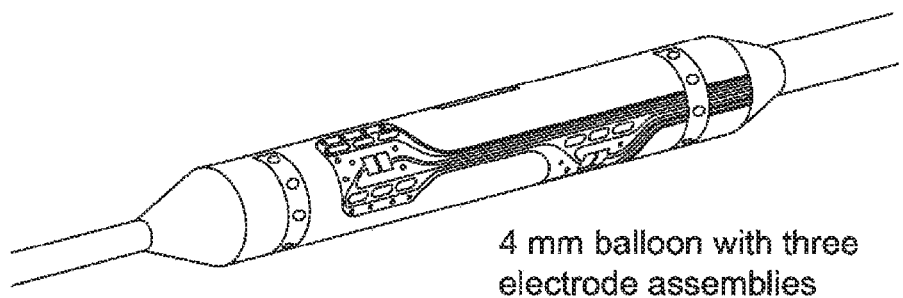
FIGS. 42 and 43 schematically illustrate expandable device(s) of a catheter that include electrodes for stimulating and measuring nerve signals.
Figure 43:
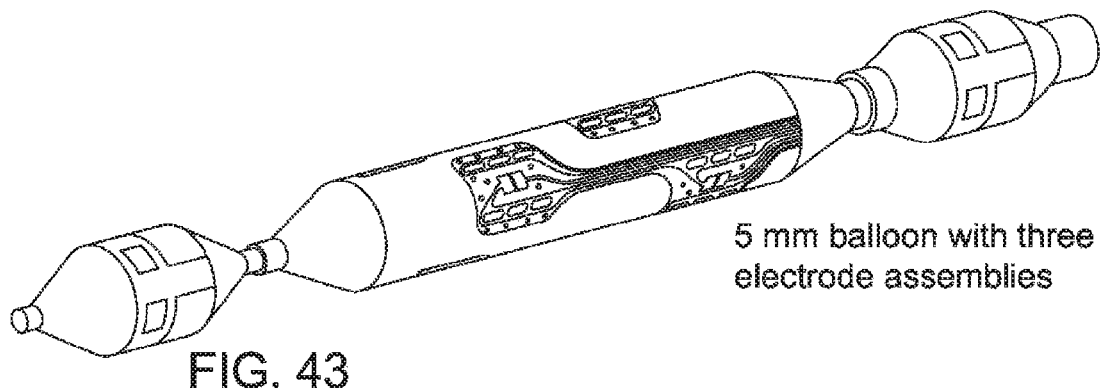

In alternative embodiments, the electrodes used to stimulate and/or monitor for nerve signals may be different from the electrodes used to deliver the energy treatment. The stimulation/monitoring electrodes may have positions, geometries, and other characteristics optimized for stimulation/monitoring and the energy delivery electrodes may have positions, geometries and other characteristics optimized for delivering the energy treatment. FIG. 42 shows an example of a catheter including electrodes for delivering an energy treatment (similar to the electrodes shown in FIG. 10) and separate electrodes (in the form, here, of circumferential ring electrodes on distal and proximal ends of the expandable device) for stimulating and monitoring for nerve signals. FIG. 43 shows an example of a catheter including separate proximal and distal expandable devices carrying ring electrodes for stimulating and monitoring for nerve signals. The electrodes of FIGS. 42 and 43 may each be a bipolar electrode, a monopolar electrode, or may constitute a bipolar electrode between the proximal and distal electrode rings. As shown in FIG. 24D the schematic representation of electrodes may be shown on a user interface to identify electrode regions that are available to be energized, and may further include indication of sufficient tissue apposition by the measurement of impedance. Because a user interface may show electrode configurations in a schematic form, it should be understood that the schematic image should not be limiting to the types of electrode configurations present on the expandable structure. Electrodes may be any one or more of rings, bipolar pairs, point electrodes, axially elongate electrodes, and the like.

In monopolar embodiments, the electrodes serve as the positive pole for stimulating and sensing during treatment, while a separate negative pole is used as a ground. The negative pole may be located on the expandable structure, at one or more points on the catheter body, or external to the patient in the form of a grounding pad. In monopolar configurations, signal processing and filtering (as further described below) are desirable options because of the relatively large difference in magnitudes between energy delivery and nerve response detection.

The RF generator and other circuitry of the control unit 110 shown and described for FIG. 1A may be used to generate the nerve stimulation signal and monitor for the response, although, in other embodiments, a separate device may be associated with the system for generating nerve stimulation and/or monitoring response.

In one embodiment, the nerve stimulation may be a voltage in the range of about 0.1V to about 5V, or about 0.5V, applied by the first electrode for a period of about 1 second or less, or about 0.5 milliseconds, followed by a pulse width modulation, which may shock a nerve tissue into propagating a nerve signal. The pulse signal may be of any form with a square wave being one example form because the rapid on/off nature of the wave form efficiently stimulates a nerve response with no ramp to or from peak voltage.

Neural activity may be assessed by measuring one or more of amplitude of the nerve signal in response to the stimulation, speed of the nerve signal in response to the stimulation, and/or fractionated amplitude of the nerve signal. Here, a fractionated amplitude refers to a net reduction and change to the nerve conduction signal as compared to a pre-treatment baseline. A pre-treatment signal would be expected to have a relatively larger amplitude and smoother transition of slope while a signal from a nerve having received at least some treatment would be expected to have a relatively lower amplitude and a less smooth, sudden, or broken transition in slope indicative of interrupted nerve conduction due to treatment. These measurements can be determined by measuring a change in voltage at the second electrode and/or a measured time between the stimulation and the response, and, in at least some embodiments, may utilize high and/or low pass filtering to differentiate the nerve signal from background noise.

Currently, interventional energy delivery therapies such as renal denervation are performed based on anatomical landmarks. In the example of renal denervation, it is known that a majority of nerves are located along the length of renal arteries. Post treatment assessment is based on secondary effects such as NEPI and blood pressure reductions, which are not typically immediate indicators and are not indicative of nerve viability.

In the current state of the art there is no means available to directly assess functional behavior of renal nerves in real-time during a renal denervation procedure. A solution to this problem is the use of alternating current or direct current to deliver sub-threshold or low stimulation signals in the vicinity of renal nerves within renal arteries to access their activity pre and post renal denervation treatment.

High resolution rapid nerve viability measurements may be accomplished via multiple localized electrodes such as those shown in FIGS. 1B and 1C, however, it should be noted that embodiments are not limited to bipolar flex circuit electrodes on balloons. Any electrode configuration (monopolar or bipolar) suitable to be mounted to a catheter-based expandable structure may be employed; ring electrodes, linear or spiral electrodes, point electrodes, and the like, may be mounted to baskets, balloons, or any other such type of structure used in catheter systems.

The measurement technique employs electric stimulation from at least one electrode over the path of a nerve to evoke the generation of an action potential that spreads along the excited nerve fibers. That action potential is then recorded on another point. This technique may be used to determine the adequacy of the conduction of the nerve impulse as it courses down a nerve, thereby detecting signs of nerve injury. The distance between electrodes and the time it takes for electrical impulses to travel between electrodes are used to calculate the speed of impulse transmission (nerve conduction velocity). A decreased speed of transmission indicates nerve damage.

Figure 44:
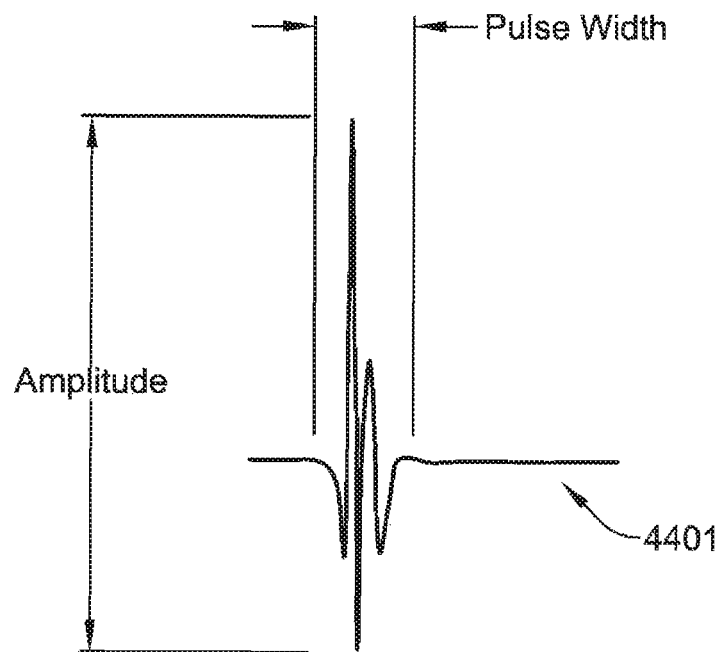
FIGS. 44 and 45 respectively illustrate a nerve response signal pre-treatment and after receiving at least some treatment.
Figure 45:
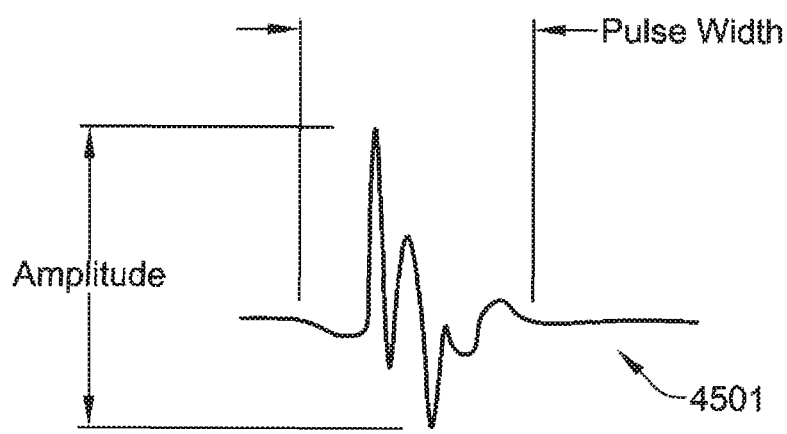

Velocity, amplitude, as well as shape of the response following electrical stimulation of renal nerves will be measured via multiple electrodes on the balloon catheter. Abnormal findings include conduction slowing, conduction blockage, lack of responses, and/or low amplitude responses Referring to FIGS. 44 and 45, electrical signal morphology is indicative of a change in nerve conduction as evidenced by the change in the degree of fractionation combined with slow conduction. FIG. 44 shows a representative nerve signal 4401 in the pre-treatment or baseline condition. FIG. 45 shows a representative nerve signal 4501 after having received at least some energy treatment. When comparing signal 4401 to signal 4501, it is evident that the amplitude of the nerve signal has been reduced while the pulse width has been increased. It is also evident that the slopes and changes in slopes of the signal 4501 are much less smooth than the slopes and changes in slopes of the signal 4401. This is illustrative of how a nerve responds to the energy treatment of the subject disclosure; as energy is delivered the nerve conductive properties are reduced or eliminated thereby causing the nerve signals to be reduced, less continuous, and slower in velocity.

Nerve signal measurement may be optimized using signal filtering such that the influence of cardiac electrical signals, stimulation signals, and system noise are filtered out of the nerve sensing circuit so as to optimize the accuracy and sensitivity of the circuit. Signal filtering may be accomplished through means such as band-pass filters. For example, a low-pass filter in the range of about 1 Hz to about 500 Hz, with an example value of 100 Hz and a high-pass filter in the range of about 1 kHz to about 10 kHz, with an example value of 5 kHz may be employed to establish the frequency band of signals to be sensed and measured by the circuit. Measurements are then used as feedback applied to the energy control algorithm used to regulate the delivery of therapeutic energy.

In a monopolar embodiment sensing is from a broader field of tissue because energy flows from the one or more positive poles of electrodes to the negative pole or poles of a common grounding path. Applying this concept to the embodiment of FIGS. 1B and 1C, an example polarity would be to use an external patch (not shown) as the positive pole while the electrode assemblies 140a-d serve as the negative poles of a common grounding circuit used for nerve signal measurement. In this seemingly backward application of energy for the purposes of sensing, the electrode assemblies 140a-d are more proximate to the nerve tissue of interest and hence may provide improved sensing accuracy by serving as negative poles for sensing. During the energy delivery mode of treatment, the polarities of the external patch and electrode assemblies 140a-d may be switched such that the electrode assemblies 140a-d are the positive poles and the external patch is the negative pole for grounding.

In a bipolar embodiment, sensing is from a localized field of tissue because the positive and negative poles of electrode assemblies 140a-d are immediately adjacent, and hence, the tissue volume sensed is much more localized than in a monopolar configuration. The close proximity of electrode poles in a bipolar arrangement may be desirable because the proximity of poles allows for an inherently lower quantity of energy delivery to energize tissue and an inherently higher degree of measurement resolution because of the smaller tissue volume between poles. Additionally, the electrode assembly 140a-d configurations provide a proximal/distal linear spacing that allows for the sensing and measuring the linear travel of a nerve signal along a path as has been described herein.

Nerve signal stimulation and measurement may occur before, during, and/or after the energy treatment. In one embodiment, neural activity is assessed prior to treatment to establish a baseline level of neural activity and is then reassessed after the treatment to determine whether a threshold level of change in neural activity has resulted. Any one or more of percentage reduction in nerve signal amplitude, degree of fractionation of signal slope, increase in duration of nerve signal pulse, and increase in time between nerve signal pulses may be used to measure a tissue response indicating that denervation in the target tissue has occurred or is in the process of occurring. In other words, total disruption of nerve activity may be a delayed response to the denervation treatment, although some decrease in nerve activity may occur during or just after the denervation treatment sufficient to indicate the effectiveness of the treatment. In alternative embodiments, an effective denervation may be characterized as one in which no nerve signal is detected in response to a pre-determined stimulation.

Nerve signal assessment may also or alternatively be conducted during the energy treatment. For instance, the control algorithm shown in FIG. 13 may be modified to allow time scale measurements of stimulated nerve activity (such measurements being on the order of any of milliseconds, microseconds, nanoseconds, picoseconds, etc.) prior to or after each electrode firing cycle. These intra-cycle measurements may be compared to a pre-treatment baseline, to measurements from earlier cycles, or to other standards.

In some embodiments, regardless of whether the nerve activity assessment is conducted pre and post treatment, periodically between each treatment cycle, or periodically after a certain number of treatment cycles, data from the neural activity assessments may be used to establish or adjust parameters for the denervation treatment. For instance, in the embodiment illustrated by FIGS. 13 and 14, while the set voltage for each cycle may be a function of previous voltage applied and measured and averaged temperature errors, total time at the treatment temperature may be a function of measured neural activity, or a function of deviation of measured neural activity from an earlier measured or pre-set baseline. One or more of measured amplitude of the nerve signal, speed of the nerve signal, and/or fractionated amplitude may be accounted for in such an algorithm. Thus, if a significant decrease in neural activity is measured early in the denervation treatment, the total treatment time may be shortened. Conversely, if the nerve signal assessments are not measuring a decrease in neural activity, the total treatment time may be lengthened. Of course, feedback from the nerve signal assessment(s) may be used to vary additional or alternative parameters of the denervation treatment.

Figure 13A:
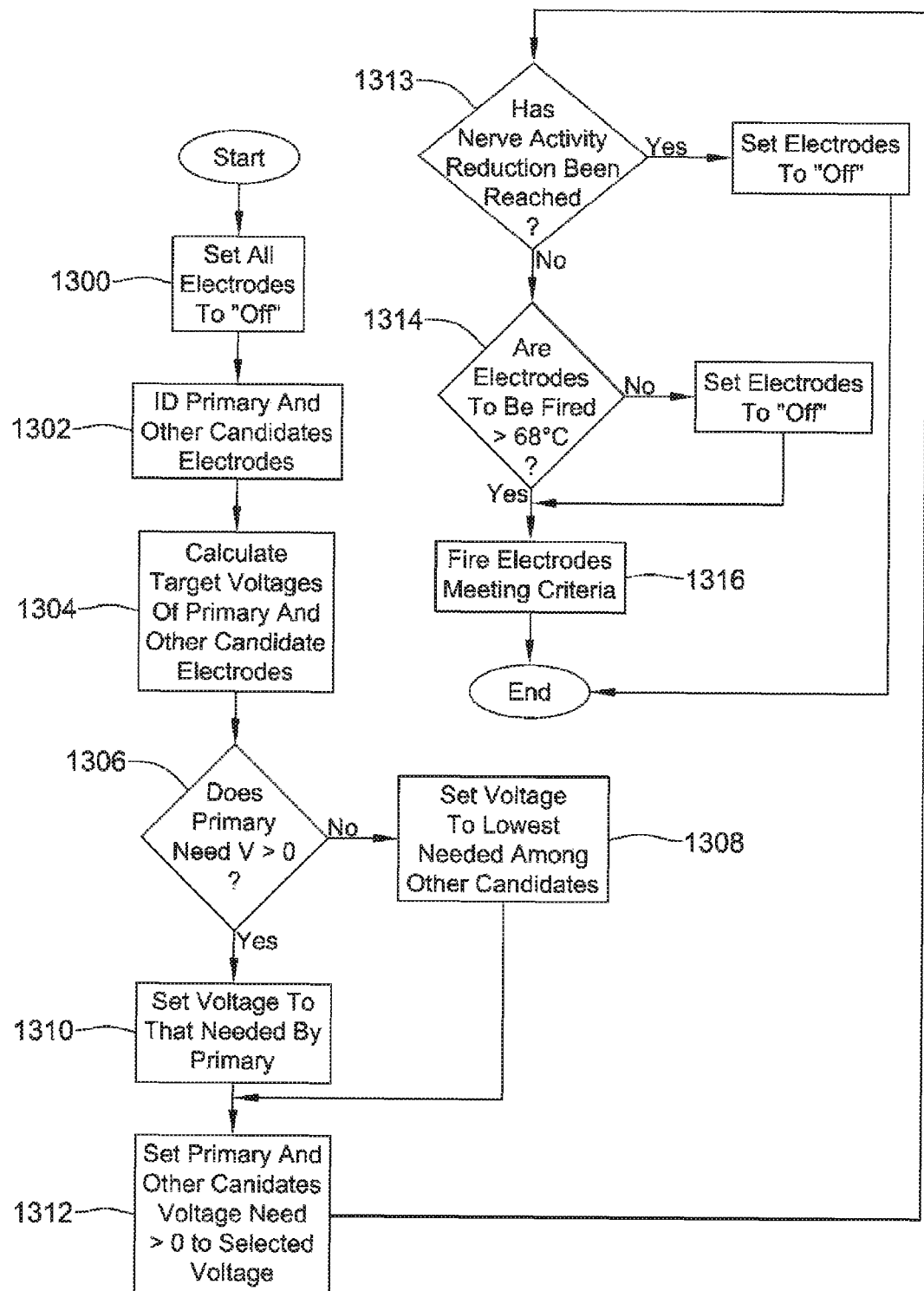
FIG. 13A illustrates another embodiment of a control loop.

Measuring of nerve signals may be directly integrated into the energy delivery and control methods described herein. As candidate electrodes are selected and energized in accordance with the control algorithm, the additional function of nerve signal measuring may be integrated into the control algorithm such that the additional control factor of nerve response increases the precision with which energy is delivered and a therapeutic response is achieved while avoiding the delivery of excess energy in order to preserve pre-treatment issue cellular state to the maximum degree possible. As shown in FIG. 13A, an additional control loop step 1313 may be used to evaluate whether the nerve signal reduction threshold has been met. If the nerve signal reduction threshold is not met, the control loop then advances to loop step 1314 to determine whether a candidate electrode has reached a temperature threshold. If at loop step 1313 a nerve is determined to have reached the signal reduction threshold, then the electrode may be deselected as a candidate electrode to be energized.

Treatment of Small/Branched Vessels and Other Passageways

The systems and devices described herein may be advantageously used in situations where other energy-based treatment systems and devices would not be suitable. For instance, embodiments of the systems and devices described herein may be used in vessels and other passageways that are too small for treatment using other catheter-based energy treatment systems. In some instances, the systems and devices described herein may be used in renal arteries or other vessels having diameters of less than 4 mm and/or lengths of less than 20 mm. Other factors, such as vessel tortuosity and proximity of the treatment site to regions that should not receive treatment, may be contra-indications for or otherwise not suitable for treatment using earlier devices but not for at least some embodiments of the presently described systems and devices.

Figure 46:
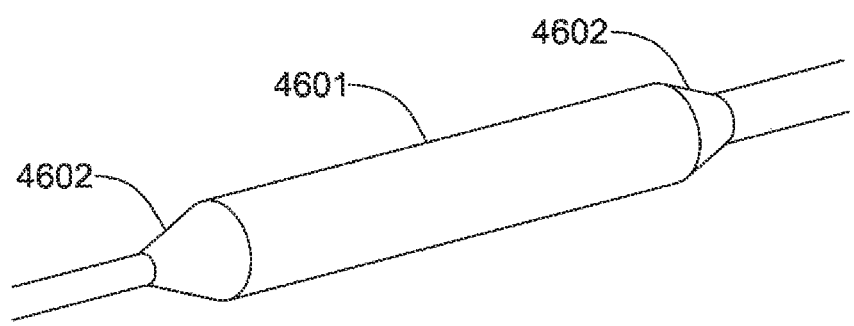
FIG. 46 illustrates an embodiment of an expandable balloon.

FIGS. 1D and E show 4 and 5 mm balloons with three electrode assemblies each. The particular geometries of these electrode assemblies and other characteristics described in preceding sections, however, facilitate their use on smaller diameter balloons, such as 1, 2 or 3 mm balloons or intermediate sizes thereof. In some instances (such as in some 1 mm embodiments), the balloon may not include a guidewire lumen. FIG. 46 shows one embodiment of a balloon with the main body 4601 being made of Kapton® a flexible polyimide film available from DuPont™, with the shoulders 4602 being made of a standard balloon material. In some instances, the Kapton® body of the balloon of FIG.

46 may be used to eliminate the need for a separate layer of the flexible circuit assemblies used on the balloon, such as to eliminate the base layer 202 shown in FIG. 2B, thereby reducing the profile of the flexible circuit assembly.

Other features of the systems and devices described above may also facilitate their use in vessels that are relatively small. For instance, delivering an energy treatment to a small diameter vessel may require particularly fine control over the amount of energy delivered and/or the temperature increase caused by the treatment. As such, the particular electrode energy delivery geometries, control algorithms, and other features described above may make the present systems and devices particularly suitable in such situations.

Figure 47:
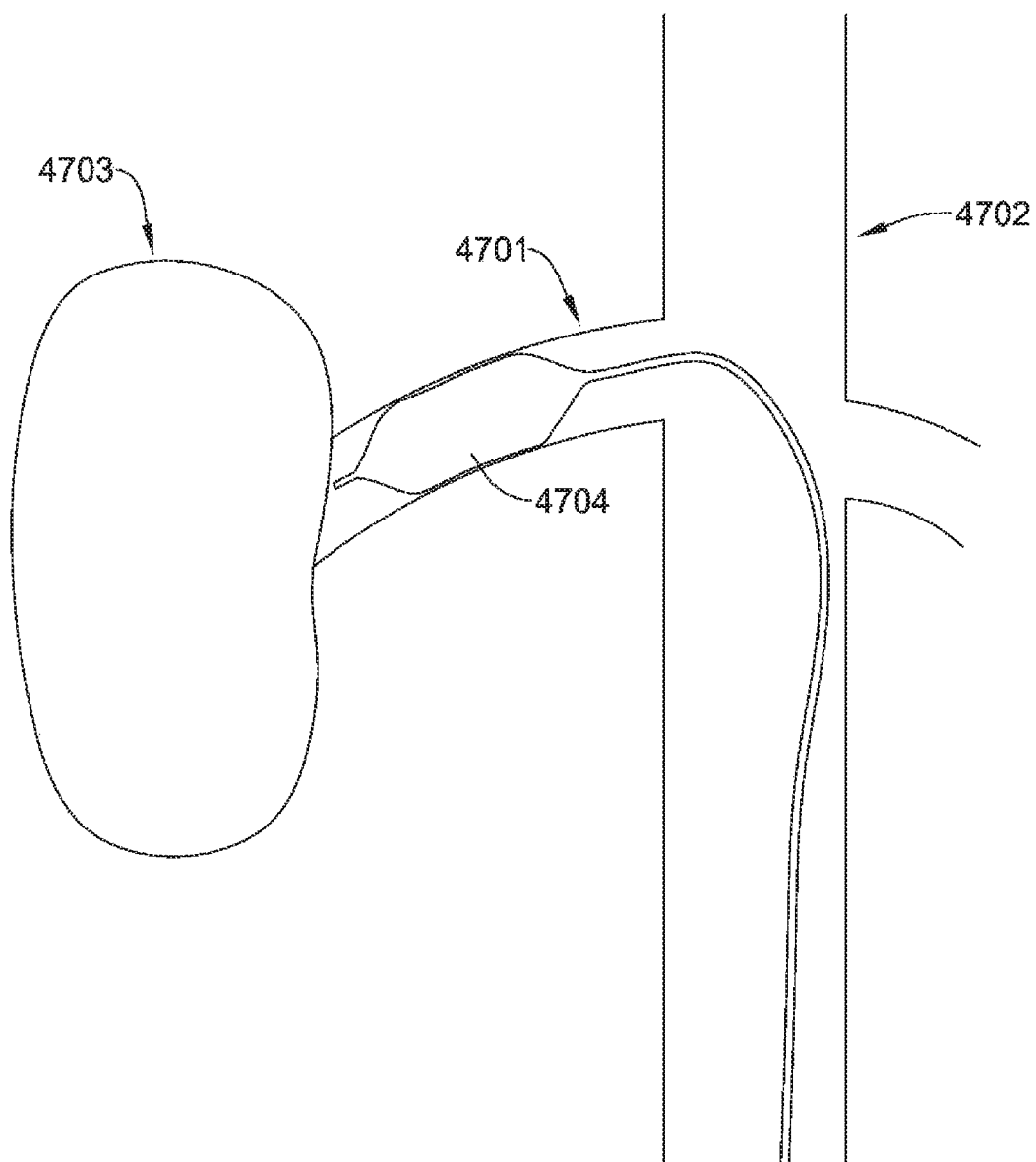
FIGS. 47-50B illustrate embodiments of methods of renal denervation treatments.

FIG. 47 schematically shows a typical primary renal artery 4701 branching from the aorta 4702 to the kidney 4703. An embodiment of the present disclosure is shown where the balloon and electrode assembly 4704 of the catheter is expanded and positioned for treatment of tissue. An energy dose is applied and the balloon is subsequently deflated and removed or repositioned.

Figure 48:
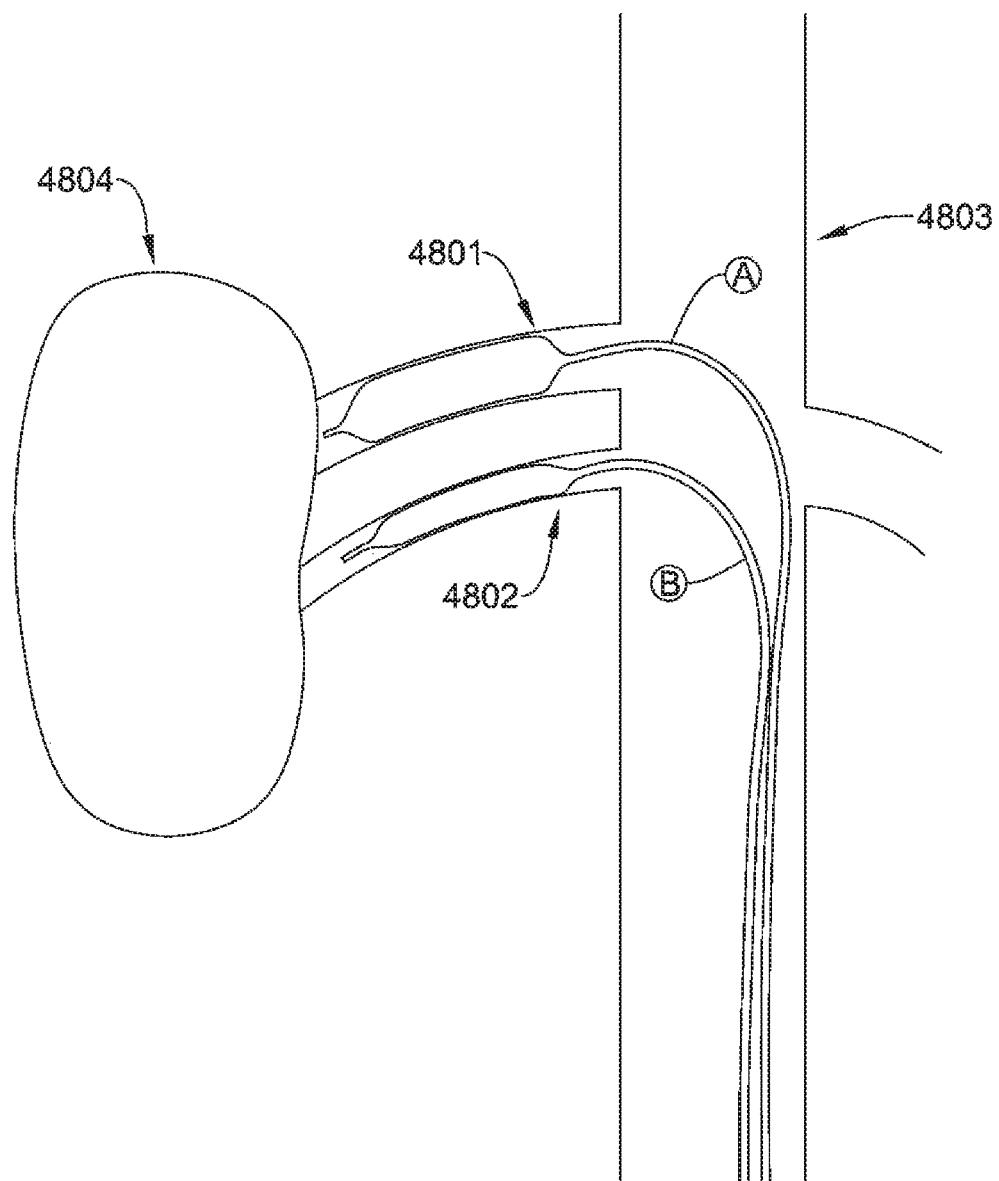

FIG. 48 schematically shows a primary 4801 and an accessory renal artery 4802 branching from the aorta 4803 with both extending to the kidney 4804. Accessory arteries may range in size from about 1 mm in diameter to about 5 mm in diameter. The renal arteries of FIG. 48 should be understood to be a simple schematic representation of what may vary from subject-to-subject in vivo. For instance, the arteries may vary in diameter, length, tortuosity, location, and number. Furthermore, these variations may be with respect to each artery as well as with respect to each subject. FIG. 48 shows a first balloon catheter A positioned for treatment in a smaller accessory artery and a second balloon catheter B positioned for treatment in a larger primary renal artery.

In practice, it may be possible that catheter A and catheter B are one in the same if the two arteries are sufficiently close in diameter to allow for complete balloon expansion and contact with the tissue of the arterial lumens. It may be further possible that catheter A and catheter B may be repositioned along the length of the respective arteries depending on the treatable length of each artery. It may also be further possible that the primary and accessory arteries may be treated simultaneously should a physician so desire.

To applicant's knowledge, prior to the present disclosure, the treatment of accessory renal arteries has not been possible because of technological limitations caused by overheating of small arteries, space constraints when operating in luminal areas with smaller cross sections, and the difficulty of navigating tortuous pathways. Because the embodiments of the present disclosure use expandable, catheter-based structures, flexible circuit electrodes on balloons, the limitations of "one size fits all" devices are obviated. Balloon and electrode assemblies of the present disclosure are incrementally sized and arranged to facilitate the precisely controlled thermal energy dose for an incremental range of luminal diameters. In other words, the balloon and electrode assembly is incrementally sized and arranged for optimized operation in a correspondingly sized lumen. The number of electrodes is chosen to avoid overheating of tissues. The balloon-based expandable structure is able to navigate to a location at a smaller, unexpanded diameter with flexibility. The large surface contact of an expanded balloon allows for uniformity in tissue contact while avoiding the bending and/or tight space constraints of single point probes or other such similar designs.

Accessory renal arteries are present in 25-30% of human patients; however these patients have been excluded from previous renal denervation studies. Within the REDUCE-HTN Clinical Study (the full contents of Vessix Vascular clinical study protocol CR012-020 being incorporated herein by reference) a subset of four subjects underwent successful treatment of primary and, at least, one accessory renal artery using the Vessix Renal Denervation System (Vessix Vascular, Inc.; Laguna Hills, Calif.) that includes a 0.014 inch over-the-wire percutaneous balloon catheter with up to 8 radiopaque gold electrodes mounted on the balloon surface in a longitudinally and circumferentially offset pattern. In an exemplary embodiment, a catheter is connected to a proprietary automated low-power RF bipolar generator that delivers a temperature-controlled therapeutic dose of RF energy at about 68° C. for about 30 seconds. The mean baseline office-based blood pressure (OBP) of this cohort was 189/93 mmHg. In addition to an average of 10.5 denervations of each main renal artery, this cohort was treated with an average of 8 denervations per accessory renal artery.

In this study, for the four subjects, no peri-procedural complications were reported and immediate post-procedure angiography indicated no renal artery spasm or any other deleterious effects. These four subjects demonstrated improvement at two weeks post-procedure with a mean reduction in OBP of −32/−16 mmHg (190/97 to 167/91; 175/92 to 129/70; 192/94 to 179/91; 183/87 to 138/55).

Figure 49:
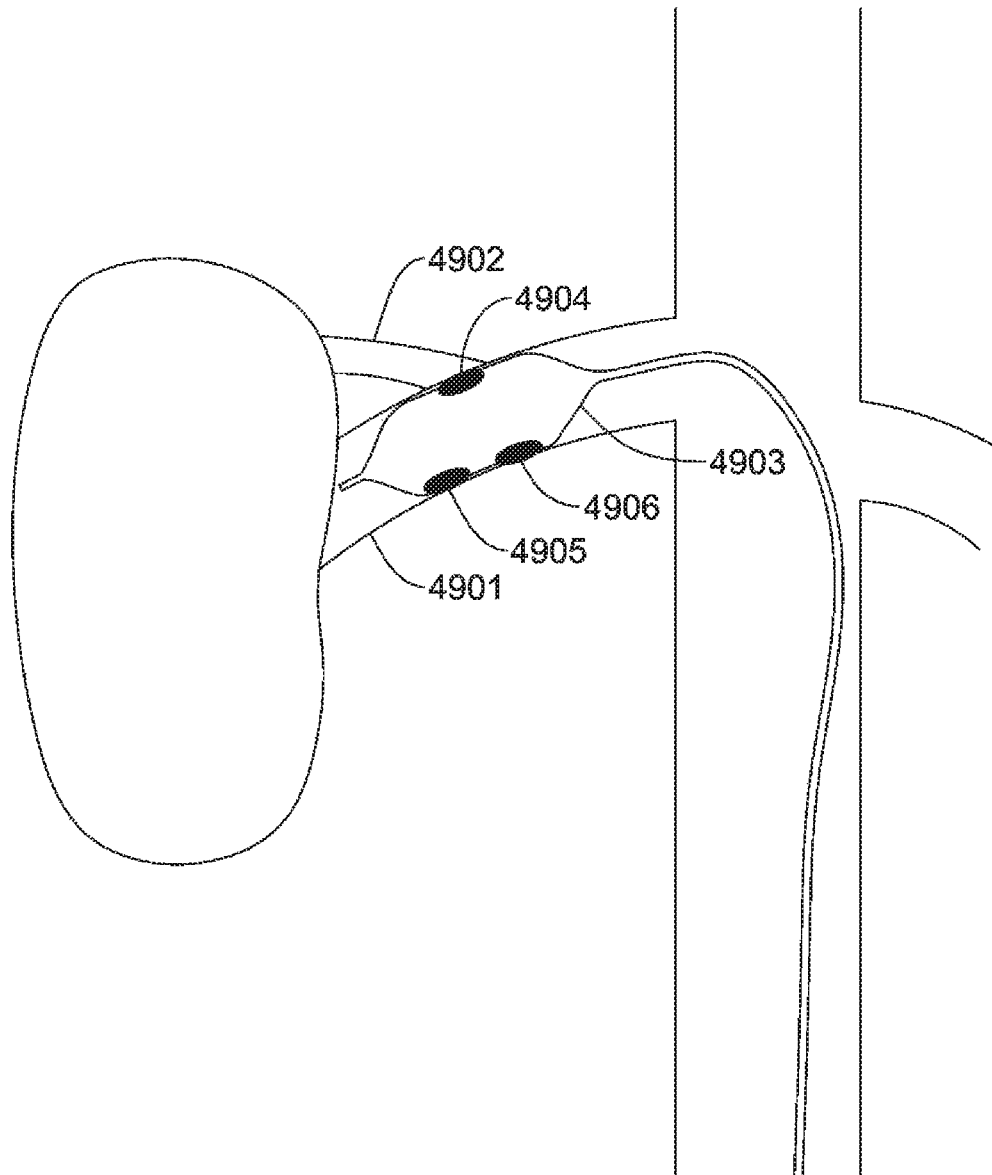

FIGS. 49 and 50 schematically illustrate non-limiting examples of renal denervation treatments where energy delivery is selectively delivered using a subset of the electrodes of an electrode assembly. FIG. 49 schematically illustrates a renal artery 4901 that includes a branch 4902. In this instance, the balloon and electrode assembly 4903 is positioned in the renal artery such that one of the electrodes 4904 is proximate an ostium joining the branch to the renal artery, and thus is not in apposition with a vessel wall. As described above in some embodiments, systems and methods in accordance with the present disclosure may be configured to selectively energize the electrodes or a subset of electrodes in apposition with the vessel wall (e.g. electrodes 4905 and 4906 in FIG. 49) while not energizing the electrodes or a subset of electrodes that are not in apposition with a vessel wall (e.g. electrode 4904). Those of skill in the art will appreciate that, in addition to the example of FIG. 49, a variety of other factors could result in less than complete apposition between the electrode assembly and vessel wall, including, without limitation, vessel tortuosity, changes in vessel diameter, presence or absence of buildup on the vessel wall, etc.

Figure 50A:
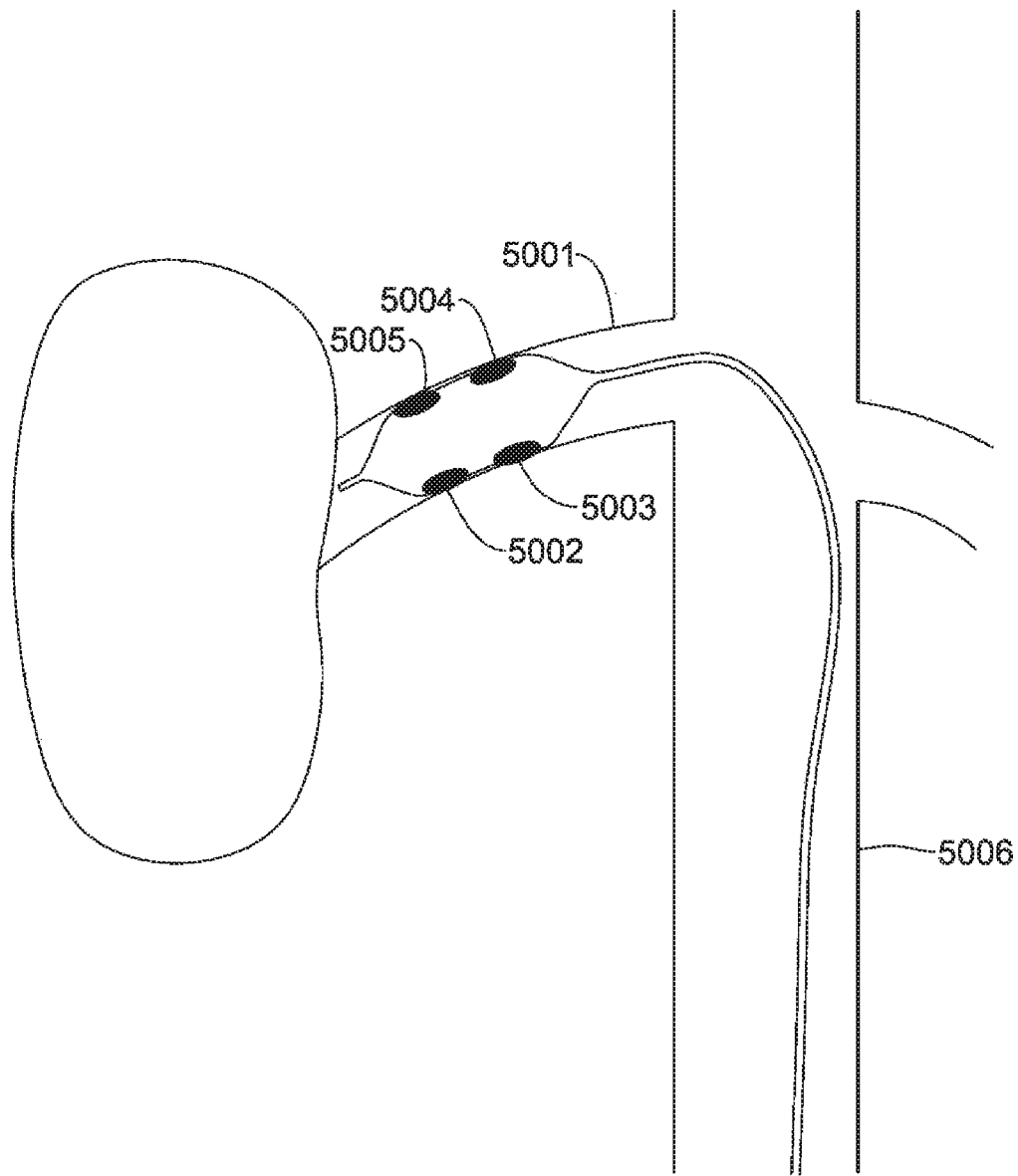
Figure 50B:
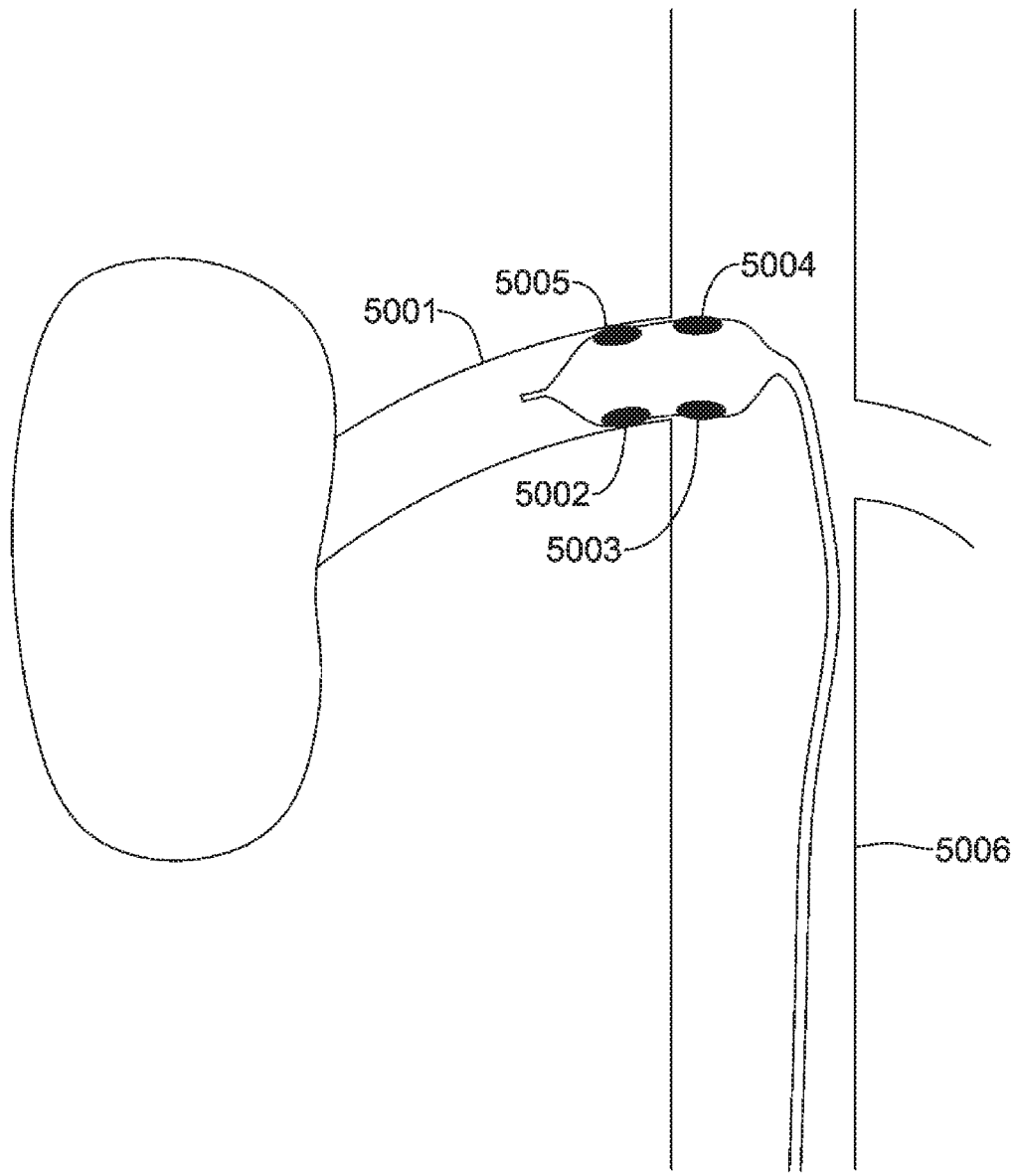

FIGS. 50A and B schematically illustrate a non-limiting example of a renal denervation treatment where an energy treatment is performed with the electrode assembly and balloon at two positions in a renal artery 5001. In FIG. 50A, the balloon is positioned such that all of the electrodes 5002-5005 are in the renal artery 5001 and are potential candidates for energization. In FIG. 50B, after an energy treatment has been performed at the position shown in FIG. 50A, the balloon and electrode assembly has been withdrawn such that a portion of it remains in the renal artery 5001 and a portion of it is in the aorta 5006. In the positioning shown in FIG. 50B, certain embodiments of systems and methods of the present disclosure will be configured to select only electrodes 5002 and 5005 (and any other electrodes positioned within renal artery 5001 and/or in apposition with a wall of the renal artery 5001) as potential candidates for energization, with electrodes in the aorta 5006 identified as non-candidates for energization. As illustrated by FIGS. 50A and B, certain embodiments of the present disclosure may facilitate delivering energy to tissues at or proximate the ostium joining the aorta 5006 to the renal artery 5001, which may, in at least some patients, be an area of relatively high concentration of nerve tissues.

While the exemplary embodiments have been described in some detail, by way of example and for clarity of understanding, those of skill in the art will recognize that a variety of modifications, adaptations, and changes may be employed.

What is claimed is:

1. A method for treating a patient having high blood pressure, the method comprising:
   (a) advancing a medical device through a blood vessel to a position within a renal artery, the medical device comprising:
      (i) a catheter;
      (ii) an expandable balloon coupled to the catheter and including an outer surface; and
      (iii) at least one flexible circuit mounted on the outer surface of the expandable balloon, including: (1) a first insulating layer, (2) at least one heat sensing device positioned at least partially within the first insulating layer, (3) a conductive layer above the first insulating layer, at least a portion of which is electrically coupled to the heat sensing device, (4) a second insulating layer above the conductive layer, and (5) at least one electrode associated with the conductive layer;
   (b) expanding the balloon in a renal artery of the patient;
   (c) driving energy through the at least one electrode so as to therapeutically alter at least one nerve proximate the renal artery so that the high blood pressure of the patient is mitigated.

2. The method of claim 1, wherein the at least one electrode of the flexible circuit includes at least one pair of bipolar electrodes and the heat sensing device is positioned between the pair of electrodes.

3. The method of claim 1, wherein the at least one electrode is positioned above the second insulating layer and is coupled to the conductive layer through the second insulating layer.

4. The method of claim 1, further comprising the step of using the heat sensing device to measure a temperature representative of both the at least one electrode and a wall of the renal artery.

5. The method of claim 1, wherein the first insulating layer and second insulating layer each comprise a flexible polymer.

6. The method of claim 1, wherein the balloon has an outer diameter of less than 4 mm when in an expanded configuration.

7. The method of claim 1, wherein the balloon is non-compliant and is configured to be fully inflated at an inflation pressure of 10 atmospheres or less.

8. A method for treating a patient, the method comprising:
   (a) advancing a device through a blood vessel to a position within a renal artery, the device comprising:
      (i) an expandable balloon including an outer surface; and
      (ii) at least one flexible circuit mounted on the outer surface, including: (1) a first insulating layer, (2) at least one heat sensing device positioned at least partially within the first insulating layer, (3) a conductive layer above the first insulating layer, at least a portion of which is electrically coupled to the heat sensing device, (4) a second insulating layer above the conductive layer, and (5) at least one pair of bipolar electrodes associated with the conductive layer;
   (b) expanding the balloon in a renal artery of the patient;
   (c) driving energy through the at least one electrode so as to therapeutically alter at least one nerve proximate the renal artery so that a heart condition of the patient is mitigated.

9. The method of claim 8, wherein the at least one pair of bipolar electrodes comprises a plurality of active electrodes and a plurality of ground electrodes.

10. The method of claim 9, wherein the plurality of active electrodes are arranged along a first longitudinal axis and the plurality of ground electrodes are arranged along a second longitudinal axis that is offset from and approximately parallel to the first longitudinal axis.

11. The method of claim 8, wherein the device further comprises a control unit coupled to the at least one pair of bipolar electrodes, and the driving energy step includes delivering radiofrequency (RF) energy to the electrodes.

12. The method of claim 11, wherein the control unit delivers RF energy to energize the electrodes so that a heat treatment zone is defined adjacent to each of the at least one pair of electrodes.

13. The method of claim 11, wherein the electrodes are energized with radiofrequency (RF) energy through the control unit in treatment cycles in a range of 10 seconds to 1 minute.

14. The method of claim 13, wherein energizing the electrodes in the range of 10 seconds to 1 minute includes heating the nerve proximate the renal artery to a temperature in a range of 55-75° C.

15. The method of claim 11, wherein the control unit energizes the electrodes with approximately 0.25-5 Watts average power.

16. A method for treating a patient, the method comprising:
   (a) advancing a device to a position within a lumen of the patient's body, the medical device comprising:
      (i) a catheter;
      (ii) an expandable member coupled to the catheter and including an outer surface; and
      (iii) at least one flexible circuit mounted on the outer surface of the expandable member, including: (1) a first insulating layer, (2) at least one heat sensing device having a first pole and second pole, the heat sensing device positioned at least partially within the first insulating layer, (3) a conductive layer above the first insulating layer, the conductive layer having a first trace connected to the first pole, a second trace connected to the second pole, and a third trace, (4) a second insulating layer above the conductive layer having one or more first openings over the first trace and one or more second openings over the third trace, (5) one or more first electrodes above the second insulating layer conductively coupled to the first trace via the first openings, and (6) one or more second electrodes above the second insulating layer conductively coupled to the third trace via the second openings;
   (b) expanding the expandable member in the lumen of the patient;
   (c) driving energy through the first and second electrodes so as to therapeutically alter at least one nerve proximate the lumen so that a condition of the patient is mitigated.

17. The method of claim 16, wherein the expandable member is a balloon.

18. The method of claim 16, wherein the first and second openings each comprise a plurality of openings and the first and second electrodes each comprise a plurality of electrodes.

19. The method of claim 16, wherein the lumen is a renal artery of the patient.

20. The method of claim 16, wherein the condition of the patient mitigated is a heart condition.

* * * * *